(12) United States Patent
Ross et al.

(10) Patent No.: US 9,572,964 B2
(45) Date of Patent: *Feb. 21, 2017

(54) IMPLANTATION TOOLS, TOOL ASSEMBLIES, KITS AND METHODS

(71) Applicant: SINOPSYS SURGICAL, INC., Boulder, CO (US)

(72) Inventors: Harry Ross, Boulder, CO (US); Brian James Willoughby, Denver, CO (US); Christopher Lee Oliver, Lakewood, CO (US); Donald F. Schomer, Fountain Hills, AZ (US); William W. Cimino, Louisville, CO (US)

(73) Assignee: SINAPSYS SURGICAL, INC., Boulder, CO (US)

( * ) Notice: Subject to any disclaimer, the term of this patent is extended or adjusted under 35 U.S.C. 154(b) by 268 days.

This patent is subject to a terminal disclaimer.

(21) Appl. No.: 14/391,577

(22) PCT Filed: Mar. 28, 2013

(86) PCT No.: PCT/US2013/034475
§ 371 (c)(1),
(2) Date: Oct. 9, 2014

(87) PCT Pub. No.: WO2013/154843
PCT Pub. Date: Oct. 17, 2013

(65) Prior Publication Data
US 2015/0065941 A1 Mar. 5, 2015

Related U.S. Application Data

(60) Provisional application No. 61/623,022, filed on Apr. 11, 2012.

(51) Int. Cl.
*A61M 27/00* (2006.01)
*A61F 9/00* (2006.01)
(Continued)

(52) U.S. Cl.
CPC ........ *A61M 27/002* (2013.01); *A61B 17/3468* (2013.01); *A61F 9/00772* (2013.01); *A61M 29/00* (2013.01); *A61M 2210/0681* (2013.01)

(58) Field of Classification Search
CPC ................ A61M 27/002; A61M 29/00; A61M 2210/0681; A61B 17/3468; A61F 9/00772
See application file for complete search history.

(56) References Cited

U.S. PATENT DOCUMENTS

| 3,726,284 A | 4/1973 | Parker |
| 3,948,272 A | 4/1976 | Guibor |

(Continued)

FOREIGN PATENT DOCUMENTS

| CN | 1735436 A | 2/2006 |
| CN | 201135547 Y | 10/2008 |

(Continued)

OTHER PUBLICATIONS

Bagdonaite, Laura, M.D. et al. "Twelve-Year Experience of Lester Jones Tubes—Results and Comparison of 3 Different Tube Types", Opthalmic Plastic Reconstructive Surgery (2015) vol. 31, No. 5., pp. 352-356.

(Continued)

*Primary Examiner* — Tatyana Zalukaeva
*Assistant Examiner* — Benjamin Klein
(74) *Attorney, Agent, or Firm* — Marsh Fischmann & Breyfogle LLP; Ross E. Breyfogle

(57) ABSTRACT

An implant device to provide an artificial fluid path in fluid communication with the lacrimal apparatus is implanted through a fistula opening into the lacrimal apparatus using a working member disposed through the implant device and a break-away sheath. Implantation kits and tool assemblies including the working member, implant device and break-away sheath facilitate implantation of the implant device.

20 Claims, 42 Drawing Sheets

(51) Int. Cl.
　　　*A61F 9/007*　　　(2006.01)
　　　*A61B 17/34*　　　(2006.01)
　　　*A61M 29/00*　　　(2006.01)

(56) References Cited

U.S. PATENT DOCUMENTS

| | | | |
|---|---|---|---|
| 4,915,684 A | 4/1990 | MacKeen et al. | |
| 4,921,485 A | 5/1990 | Griffiths | |
| 5,169,386 A | 12/1992 | Becker et al. | |
| 5,345,948 A | 9/1994 | O'Donnell, Jr. | |
| 6,041,785 A * | 3/2000 | Webb | A61B 17/12022 128/887 |
| 6,083,188 A | 7/2000 | Becker | |
| 6,629,533 B1 | 10/2003 | Webb et al. | |
| 6,878,165 B2 | 4/2005 | Makino | |
| 6,966,888 B2 | 11/2005 | Cullen et al. | |
| 7,156,821 B2 | 1/2007 | Dohlman | |
| 7,169,163 B2 | 1/2007 | Becker | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| D590,935 S | 4/2009 | Becker | |
| 7,547,323 B2 | 6/2009 | Lavigne | |
| 7,559,925 B2 | 7/2009 | Goldfarb et al. | |
| 7,641,644 B2 | 1/2010 | Chang et al. | |
| 7,645,272 B2 | 1/2010 | Chang et al. | |
| 7,654,997 B2 | 2/2010 | Makower et al. | |
| 7,713,255 B2 | 5/2010 | Eaton et al. | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,758,534 B2 | 7/2010 | Pearson | |
| 7,771,409 B2 | 8/2010 | Chang et al. | |
| 7,785,315 B1 | 8/2010 | Muni et al. | |
| 7,803,150 B2 | 9/2010 | Chang et al. | |
| 7,846,124 B2 | 12/2010 | Becker | |
| 9,022,967 B2 | 5/2015 | Oliver et al. | |
| 2002/0032444 A1 | 3/2002 | Mische | |
| 2002/0107579 A1 | 8/2002 | Makino | |
| 2004/0068286 A1* | 4/2004 | Mendius | A61B 17/12099 606/191 |
| 2004/0077989 A1 | 4/2004 | Goode et al. | |
| 2004/0116958 A1 | 6/2004 | Gopferich et al. | |
| 2004/0204704 A1* | 10/2004 | Tamplenizza | A61B 18/24 606/16 |
| 2004/0254516 A1 | 12/2004 | Murray et al. | |
| 2005/0197614 A1 | 9/2005 | Pritchard et al. | |
| 2005/0240143 A1 | 10/2005 | Dohlman | |
| 2005/0245906 A1 | 11/2005 | Makower et al. | |
| 2005/0273033 A1 | 12/2005 | Grahn et al. | |
| 2006/0063973 A1 | 3/2006 | Makower et al. | |
| 2006/0142736 A1 | 6/2006 | Hissink et al. | |
| 2006/0251575 A1 | 11/2006 | Morgenstern | |
| 2006/0276738 A1* | 12/2006 | Becker | A61F 9/00772 604/8 |
| 2007/0005120 A1 | 1/2007 | Villacampa et al. | |
| 2007/0112291 A1 | 5/2007 | Borgesen | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0255263 A1* | 11/2007 | Sugimoto | A61F 9/00772 606/1 |
| 2007/0269487 A1 | 11/2007 | De Juan et al. | |
| 2007/0276314 A1* | 11/2007 | Becker | A61F 9/00772 604/8 |
| 2007/0282305 A1 | 12/2007 | Goldfarb et al. | |
| 2007/0293726 A1 | 12/2007 | Goldfarb et al. | |
| 2007/0293727 A1 | 12/2007 | Goldfarb et al. | |
| 2008/0082037 A1 | 4/2008 | Pearson | |
| 2008/0097154 A1 | 4/2008 | Makower et al. | |
| 2008/0097354 A1 | 4/2008 | Lavigne | |
| 2008/0097514 A1 | 4/2008 | Chang et al. | |
| 2008/0103361 A1 | 5/2008 | Makower et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0125805 A1 | 5/2008 | Mische | |
| 2008/0132938 A1 | 6/2008 | Chang et al. | |
| 2008/0154237 A1* | 6/2008 | Chang | A61B 17/24 604/514 |
| 2008/0154250 A1 | 6/2008 | Makower et al. | |
| 2008/0195041 A1 | 8/2008 | Goldfarb et al. | |
| 2008/0228085 A1 | 9/2008 | Jenkins et al. | |
| 2008/0234720 A1 | 9/2008 | Chang et al. | |
| 2008/0275483 A1 | 11/2008 | Makower et al. | |
| 2008/0281156 A1 | 11/2008 | Makower et al. | |
| 2008/0287908 A1 | 11/2008 | Muni et al. | |
| 2008/0306428 A1 | 12/2008 | Becker | |
| 2008/0319424 A1 | 12/2008 | Muni et al. | |
| 2009/0005763 A1 | 1/2009 | Makower et al. | |
| 2009/0028923 A1 | 1/2009 | Muni et al. | |
| 2009/0030274 A1 | 1/2009 | Goldfarb et al. | |
| 2009/0036818 A1 | 2/2009 | Grahn et al. | |
| 2009/0099626 A1 | 4/2009 | de Juan, Jr. et al. | |
| 2009/0104248 A1* | 4/2009 | Rapacki | A61F 9/0017 424/427 |
| 2009/0105749 A1* | 4/2009 | de Juan | A61B 17/3468 606/206 |
| 2009/0177163 A1* | 7/2009 | King | A61M 25/0668 604/167.03 |
| 2009/0187098 A1 | 7/2009 | Makower et al. | |
| 2009/0198216 A1 | 8/2009 | Muni et al. | |
| 2009/0204142 A1 | 8/2009 | Becker | |
| 2009/0221988 A1 | 9/2009 | Ressemann et al. | |
| 2009/0240112 A1 | 9/2009 | Goldfarb et al. | |
| 2009/0240237 A1 | 9/2009 | Goldfarb et al. | |
| 2009/0275882 A1 | 11/2009 | Lavigne | |
| 2009/0275903 A1 | 11/2009 | Lavigne | |
| 2009/0281621 A1 | 11/2009 | Becker | |
| 2009/0312745 A1 | 12/2009 | Goldfarb et al. | |
| 2010/0034870 A1 | 2/2010 | Sim et al. | |
| 2010/0042046 A1 | 2/2010 | Chang et al. | |
| 2010/0076269 A1 | 3/2010 | Makower et al. | |
| 2010/0099946 A1 | 4/2010 | Jenkins et al. | |
| 2010/0100181 A1 | 4/2010 | Makower et al. | |
| 2010/0106255 A1 | 4/2010 | Dubin | |
| 2010/0114066 A1 | 5/2010 | Makower et al. | |
| 2010/0121308 A1 | 5/2010 | Muni et al. | |
| 2010/0174138 A1 | 7/2010 | Chang et al. | |
| 2010/0174308 A1 | 7/2010 | Chang et al. | |
| 2010/0198247 A1 | 8/2010 | Chang et al. | |
| 2010/0210901 A1 | 8/2010 | Makower et al. | |
| 2010/0268245 A1 | 10/2010 | Chang et al. | |
| 2010/0274204 A1 | 10/2010 | Rapacki et al. | |
| 2010/0274259 A1 | 10/2010 | Yaron et al. | |
| 2010/0298862 A1 | 11/2010 | Chang et al. | |
| 2010/0317969 A1 | 12/2010 | Becker | |
| 2011/0004057 A1 | 1/2011 | Goldfarb et al. | |
| 2011/0060214 A1 | 3/2011 | Makower | |
| 2011/0105989 A1 | 5/2011 | Becker | |
| 2011/0112512 A1 | 5/2011 | Muni et al. | |
| 2011/0224680 A1 | 9/2011 | Barker | |
| 2011/0276131 A1 | 11/2011 | De Juan, Jr. et al. | |
| 2012/0089071 A1 | 4/2012 | Oliver et al. | |
| 2012/0245539 A1 | 9/2012 | Zarins et al. | |
| 2013/0030545 A1 | 1/2013 | Gross et al. | |
| 2013/0231693 A1 | 9/2013 | Edgren et al. | |
| 2013/0274647 A1 | 10/2013 | Oliver et al. | |
| 2014/0012309 A1 | 1/2014 | Keith et al. | |

FOREIGN PATENT DOCUMENTS

| | | |
|---|---|---|
| EP | 0631793 A1 | 1/1995 |
| EP | 1110577 A1 | 12/2001 |
| FR | 2813522 A1 | 3/2002 |
| WO | 2009035562 A2 | 3/2009 |
| WO | 2009145755 A1 | 12/2009 |

(56) References Cited

FOREIGN PATENT DOCUMENTS

| WO | 2010096822 A2 | 8/2010 |
| WO | 2010111528 A2 | 9/2010 |
| WO | 2011066479 A1 | 6/2011 |

OTHER PUBLICATIONS

Sadeghi, Nader, M.D. et al. Transnasal Endoscopic Medial Maxillectomy for Inverting Papilloma. Laryngoscope (2003) 113:749-753.
Dictionary Definition for 'inject'. hllps:l/www.google.com/search?q=inject&sourceid=ie7&rls=com.microsoft:en-us:IE-Address&ie=&oe=&gws_rd=ssl.
Mangan, BG et al. Bilateral Nasolacrimal Duct Atresia in a Cria. Veterinary Opthalmology (2008) 11, 1, 49-54.
Giuliano, EA et al. Dacryocystomaxillorhinostomy for Chronic Dacryocystitis in a Dog. Veterinary Opthalmology (2006) 9, 2, 89-94.
Wilson, DG et al. Surgical Reconstruction of the Nasolacrimal System in the Horse. Equine Veterinary Science (1991) vol. II, No. 4, pp. 232-234.
Steinmetz, A et al. Surgical Removal of a Dermoid Cyst From the Bony Part of Thenasolacrimal Duct in a Scottish Highland Cadle Heifer. Veterinary Opthalmology (2009) 12, 4, 259-262.
Mcilnay, TR et al. Use of Canaliculorhinostomy for Repair of Nasolacrimal Duct Obstruction in a Horse. JAVMA (2001) vol. 218, No. 8. Scientific Reports: Clinical Report. 1323-1324.
Gionfriddo Jr. The nasolacrimal system. In: Textbook of Small Animal Surgery 3rd edition. 2003, Slatter OM ed. Saunders, Philadelphia PA, pp. 1356-1358.

\* cited by examiner

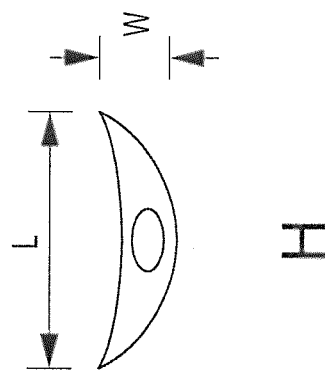
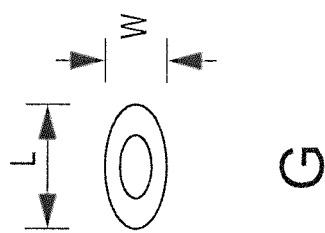
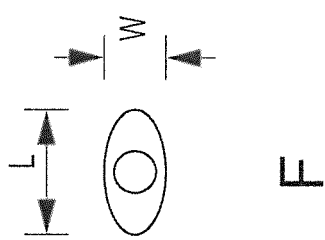
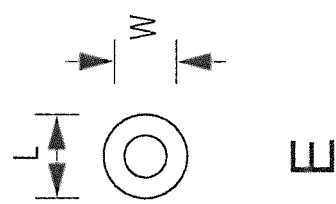
FIG.11

IMPLANTATION TOOLS, TOOL ASSEMBLIES, KITS AND METHODS

CROSS-REFERENCE TO RELATED APPLICATIONS

This application claims a benefit of priority to U.S. provisional patent application No. 61/623,022 entitled "IMPLANTATION TOOL, TOOL ASSEMBLIES, KITS AND METHODS" filed Apr. 11, 2012.

This application incorporates by reference each and every portion of the following: international patent application no. PCT/US2011/055456 entitled "IMPLANT DEVICE, TOOL, AND METHODS RELATING TO TREATMENT OF PARANASAL SINUSES" filed Oct. 7, 2011; U.S. nonprovisional patent application Ser. No. 13/225,213 entitled "IMPLANT DEVICE, TOOL, AND METHODS RELATING TO TREATMENT OF PARANASAL SINUSES" filed Sep. 2, 2011; U.S. provisional patent application No. 61/528,058 entitled "IMPLANT DEVICE, TOOL, AND METHODS RELATING TO TREATMENT OF PARANASAL SINUSES" filed Aug. 26, 2011; and U.S. provisional patent application No. 61/404,716 entitled "METHODS AND TOOLS FOR TREATMENT AND PREVENTION OF SINUSITIS" filed Oct. 8, 2010.

FIELD OF THE INVENTION

The invention relates to treatment of conditions of the paranasal sinuses, including with respect to implant devices, surgical tools and methods.

BACKGROUND OF THE INVENTION

In the United States alone, 35 million people a year are treated for sinus infections, or sinusitis, and 7 million of those will suffer from chronic sinusitis and will have minimal response to prescription drug therapies. Current surgical interventions may be expected to, at best, offer only moderate symptomatic improvement but no cure.

Current drug therapies include oral administration as pills and nasal topical administration, neither of which is conducive to delivering adequate concentration of medication to the involved paranasal sinus. In addition to medication, frequent sinus irrigation can be helpful in flushing out debris, irritants and obstructing viscous fluids, but patients are generally not able to adequately perform this procedure at home.

For patients with particularly severe symptoms, surgical drainage may be the only additional option. An early surgical procedure was the Caldwell-Luc procedure, which involves creating a permanent fistula from the base of the paranasal sinus into the oral cavity above the front upper incisors. More recently, other surgical access points to the paranasal sinuses have been attempted. A variety of endoscopic techniques have been developed that access the paranasal sinuses through the nose, including functional endoscopic sinus surgery (FESS) and balloon sinuplasty. All attempt to increase drainage, but utilize different routes or tools. None of these surgical approaches has achieved widespread success, and millions of chronic sinusitis patients continue to suffer long-term disability and discomfort.

SUMMARY OF INVENTION

A first aspect of the invention involves a method for implanting an implant device to provide an artificial fluid path in fluid communication with the lacrimal apparatus. An implantation tool assembly may be positioned in an implantation position relative to a fistula having a proximal end opening into the lacrimal apparatus. The implantation tool assembly comprises an implantation tool, an implant device and a sheath tool. The implantation tool includes a proximal end and a distal end, and comprises:
  a working member extending longitudinally in a direction from the proximal end toward the distal end of the implantation tool assembly; and
  a hand-manipulable handle connected with the working member and hand graspable proximal of the working member to hand manipulate the implantation tool.
The implant device comprises:
  a proximal end and a distal end at opposite longitudinal ends of the implant device;
  a first internal passage extending between the proximal end and the distal end of the implant device and having a first end open at the proximal end of the implant device and a second end open at the distal end of the implant device;
  wherein, the implant device is configured to be implanted with the proximal end disposed in the lacrimal apparatus; and
  wherein, the implant device is slidably mounted on the working member with the working member disposed through the first internal passage and with the proximal end of the implant device disposed toward the handle and the distal end of the implant device disposed toward the distal end of the implantation tool.
The sheath tool has a proximal end and a distal end, and comprises:
  a break-away sheath and a second internal passage extending longitudinally through the break-away sheath in a direction from the proximal end toward the distal end of the sheath tool;
  wherein, at least a portion of the working member distal to the implant device is slidably disposed in the second internal passage;
When the implantation tool assembly is in the implantation position:
  at least a portion of the break-away sheath and at least a portion of the working member disposed within the second internal passage are disposed in the fistula; and
  at least a portion of the implant device is disposed proximal of the fistula.
After positioning the implantation tool assembly in the implantation position, the break-away sheath may be removed from the working member while maintaining disposed in the fistula at least a portion of the working member distal of the implant device. After removing the break-away sheath, the implant device may be positioned with at least a portion of the implant device disposed in the fistula while maintaining at least a portion of the working member disposed in the fistula. After positioning the implant device, the working member may be removed from the first internal passage to disengage the implantation tool from the implant device and to leave the implant device in an implanted position with at least a portion of the implant device disposed in the fistula and with the proximal end of the implant device disposed in the lacrimal apparatus.

A second aspect of the invention involves an implantation kit with components for implantation of an implant device to provide an artificial fluid path in fluid communication with the lacrimal apparatus. The implantation kit comprises an implant device, implantation tool and sheath tool. The implant device comprises:

a proximal end and a distal end at opposite longitudinal ends of the implant device;

a first internal passage extending between the proximal end and the distal end of the implant device and having a first end open at the proximal end of the implant device and a second end open at the distal end of the implant device;

a longitudinal length between the proximal end and the distal end of the implant device in a range of from 2 millimeters to 50 millimeters;

a width of the first internal passage transverse to the length in a range of from 0.25 millimeter to 5 millimeters; and wherein, the implant device is configured to be implanted with the proximal end disposed in the lacrimal apparatus.

The implantation tool has a proximal end and a distal end, and comprises:

a working member extending longitudinally in a direction from the proximal end toward the distal end of the implantation tool; and a hand-manipulable handle connected with the working member and hand graspable proximal of the working member to hand manipulate the implantation tool;

wherein, the working member is configured to be slidably inserted through the first internal passage of the implant device to mount the implant device on the working member with the proximal end of the implant device disposed toward the handle and the distal end of the implant device disposed toward the distal end of the implantation tool.

The sheath tool has a proximal end and a distal end, and comprises:

a break-away sheath and a second internal passage extending longitudinally through the break-away sheath in a direction from the proximal end toward the distal end of the sheath tool;

wherein, the sheath tool is configured to slidably receive at least a portion of the working member in the second internal passage; and wherein, the sheath tool is configured for break-away removal of the break-away sheath from the working member of the implantation tool when a portion of the working member of the implantation tool is disposed in the second internal passage.

In a third aspect, the invention involves an implantation tool assembly for implantation of an implant device to provide an artificial fluid path in fluid communication with the lacrimal apparatus. The implantation tool assembly comprises an implant device, implantation tool and sheath tool. The implant device comprises:

a proximal end and a distal end at opposite longitudinal ends of the implant device;

a first internal passage extending between the proximal end and the distal end of the implant device and having a first end open at the proximal end of the implant device and a second end open at the distal end of the implant device;

a longitudinal length between the proximal end and the distal end of the implant device in a range of from 2 millimeters to 50 millimeters;

a width of the first internal passage transverse to the length in a range of from 0.25 millimeter to 5 millimeters; and wherein, the implant device is configured to be implanted with the proximal end disposed in the lacrimal apparatus.

The implantation tool has a proximal end and a distal end, and comprises:

a working member extending longitudinally in a direction from the proximal end toward the distal end of the implantation tool assembly; and a hand-manipulable handle connected with the working member and hand graspable proximal of the working member to hand manipulate the implantation tool;

wherein, the working member is disposed through the first internal passage of the implant device with the proximal end of the implant device disposed toward the handle and the distal end of the implant device disposed toward the distal end of the implantation tool.

The sheath tool has a proximal end and a distal end, and comprises:

a break-away sheath and a second internal passage extending longitudinally through the break-away sheath in a direction from the proximal end toward the distal end of the sheath tool;

wherein, the sheath tool is configured to slidably receive at least a portion of the working member in the second internal passage, and at least a portion of the working member of the implantation tool is disposed in the second internal passage in the break-away sheath; and wherein, the sheath tool is configured for break-away removal of the break-away sheath from the working member of the implantation tool to remove the break-away sheath from the at least a portion of the member of the implantation tool disposed in the second internal passage in the break-away sheath.

A number of feature refinements and additional features are applicable to the first aspect, the second aspect and the third aspect of the invention. These feature refinements and additional features may be used individually or in any combination within the subject matter of these different aspects. As such, each of the following features may be, but are not required to be, used within any other feature or combination of features of the first aspect, second aspect or third aspect of the invention.

Some possible additional features and feature refinements applicable to a method of the first aspect are now summarized.

Prior to the positioning the implantation tool assembly in the implantation position the method may include forming the fistula, comprising piercing tissue adjacent the lacrimal apparatus with the working member. The working member may be a solid member with a pointed distal tip. The working member may be a hollow member, and during the forming of a fistula, a solid insert member may be disposed through the hollow working member and may be slidably removable from a proximal end of the hollow working member. During forming of a fistula the working member may be disposed through the second internal passage of the break-away sheath with a distal end of the working member located distal of the distal end of the sheath tool, Forming a fistula may comprise advancing the working member and break-away sheath through the tissue, followed by retracting the working member from the fistula, such as by slidably removing the working member from the second internal passage of the break-away sheath while leaving at least a portion of the break-away sheath disposed in the fistula. During the forming of a fistula, a hollow dilator member may or may not be disposed through the second internal passage annularly located between working member and the break-away sheath. Before positioning the implantation tool assembly in the implantation position, such a dilator member, if present, may be removed from the second internal passage. Forming a fistula may comprise forming an initial fistula to the width of the working member and then dilating the initial fistula to the width of the break-way sheath and dilating the initial fistula, such as by advancing the break-away sheath through the initial fistula. Between forming such an initial fistula and dilating the initial fistula, contrast media may be injected through the initial fistula and imaged to confirm the location of the initial fistula.

The method may comprise maintaining at least a portion of the break-away sheath disposed in the fistula following such retracting until the step of removing the break-away sheath from the working member. Contrast media may be injected through the fistula and imaged to confirm the location of the fistula prior to the removing the break-away sheath.

In some method embodiments, during forming of a fistula the implant device may be mounted on the working member with at least a portion of the implant device located proximal of the break-away sheath. In some other method embodiments, the implant device may not be mounted on the working member during forming of a fistula. The method may comprise after forming a fistula and before the positioning the implantation tool assembly in an implantation position, retracting the working member from the fistula and slidably mounting the implant device on the working member. Positioning the implantation tool assembly in an implantation position may comprise, after the slidably mounting the implant device on the working member, with the implant device mounted on the working member inserting into the fistula at least a portion of the working member that is distal of the mounted implant device.

The fistula for implantation of the implant device may have a distal end opening into a paranasal sinus selected from the group consisting of a maxillary sinus, a frontal sinus and an ethmoid sinus. In some preferred implementations, such a paranasal sinus may be an ethmoid sinus. The implanted position the distal end of the implant device may be located in a paranasal sinus. The fistula may have a distal end opening into the nasal cavity. The fistula may have a proximal end opening in the lacrimal apparatus within the orbit or in the nasolacrimal duct. In the implanted position the implant device may be located in the nasal cavity. A treatment formulation may be injected through the fistula into a paranasal sinus prior to the removing the working member from the first internal passage.

Some possible additional features and feature refinements applicable to an implantation kit of the he tool assemblies of the second aspect are now summarized.

The implantation tool and the sheath tool may be assemblable in a first tool assembly useful for forming a fistula having a proximal end opening into the lacrimal apparatus. The implantation tool, the implantation device and the sheath tool may be assemblable in a second tool assembly configuration useful for implanting the implant device in a fistula having a proximal end opening into the lacrimal apparatus.

The first tool assembly configuration may include the implant device mounted on the working member or be in the absence of the implant device mounted on the working member. In the first tool assembly configuration the working member may be inserted through the second internal passage of the beak-away sheath with the proximal end of the sheath tool disposed toward the handle of the implantation tool and with a distal portion of the working member exposed distal of a distal end of the break-away sheath. The first tool assembly may comprise the implant device mounted on the working member with at least a portion of the implant device being proximal of the break-away sheath.

The second tool assembly configuration may include the working member inserted through the first internal passage of the implantation device with the proximal end of the implantation device disposed toward the handle of the implantation tool and may include the working member inserted through at least a portion of the second internal passage with the proximal end of the sheath tool disposed toward the handle of the working member, and at least a portion of the implant device may be disposed proximal of the break-away sheath.

The implementation kit may comprise a dilator tool including a hollow dilator member. The hollow dilator tool may be assemblable with the implantation tool and the sheath tool in the first tool assembly configuration with at least a portion of the hollow dilator member disposed annularly between the working member and the break-away sheath and with at least a distal portion of the working member being exposed distal of a distal end of the hollow dilator member. In the first tool assembly configuration, the implantation tool and the dilator tool may be slidably disengageable from the proximal end of the sheath tool, whereby after the first tool assembly configuration is used to form the fistula, the implantation tool and the dilator tool are retractable to disengage from the sheath tool to leave the sheath tool disposed with at least a portion of the break-away sheath within the fistula. In the first tool assembly configuration, the distal end of the dilator member may be disposed distal of the distal end of the sheath tool and proximal of the distal end of the implantation tool. The first tool assembly may be in the absence of a hollow member annularly disposed between working member and the break-away sheath. The second tool assembly may be in the absence of the dilator tool.

The working member may be a hollow member, and the implantation kit may comprise a solid insert member configured to be slidably disposed through at least a portion of the hollow working member. The solid insert member may be configured to be disposed through the hollow working member with a distal end of the solid insert member and a distal end of the hollow working member forming a piercing tip for piercing tissue to form a fistula. The working member may be a solid member.

Some possible additional features and feature refinements applicable to an implantation tool assembly of the third aspect of the invention are now summarized.

The working member may be a hollow member, and the tool assembly may comprise a solid insert member disposed through at least a portion of the hollow working member. A distal portion of the hollow working member and a distal portion of the solid insert member may form a piercing tip at a distal end of tool assembly. At least a portion of the implant device mounted on the working member may be located proximal of the break-away sheath. At least a distal portion of the working member may be exposed distal of the break-away sheath. The tool assembly may or may not comprise a hollow dilator member annularly disposed between the working member and the break-away sheath.

Some possible additional features and feature refinements applicable to the subject matter of any of the first aspect, second aspect or third aspect of the invention are now summarized.

The lacrimal apparatus may be the lacrimal apparatus within the orbit or within the nasolacrimal duct.

The working member may have a distal end that is at the distal end of the implantation tool. The working member may extend from a distal end of the handle to the distal end of the implantation tool. The working member may have a longitudinal length in a range having a lower limit of 50, 60, 70 or 80 millimeters and an upper limit of 250 millimeters, 225, 200, 175, 160 or 150 millimeters. The working member may have a longitudinal length at least as long as the combined longitudinal lengths of the implant device and the sheath tool. The working member may be a solid member with a piercing tip. The working member may be a hollow member configured for receipt of a solid member insert therethrough. The working member may have an exterior width within a range having a lower limit of 0.5, 0.6, 0.7 or 0.8 millimeter and an upper limit of 1.5, 1.3, 1.2 or 1 millimeter. The working member may comprise a 18 to 22 gauge needle. Working member may comprise a 20 gauge needle. The working member may have a maximum outer diameter that is smaller than a minimum diameter of the first internal passage of the implant device by no more than 0.25 millimeter. The working member may have a longitudinal length that is larger than a longitudinal length of either the implant device or the break-away sheath.

The sheath tool may have a longitudinal length that is greater than a longitudinal length of the implant device. A longitudinal length of the sheath tool may be in a range having a lower limit of 25, 30 or 40 millimeters and an upper limit of 120, 100, 80 or 65 millimeters. A longitudinal length of the break-away sheath may be in a range having a lower limit of 20, 25 or 30 millimeters and an upper limit of 100, 75 or 60 millimeters. The implant device may have a longitudinal length in a range of from 10 to 25 millimeters.

The break-away sheath may be made of a polymer composition. The polymer composition comprises polytetrafluoroethylene (PTFE). The polymer composition may comprise a polymer selected from the group consisting of polyethylene, polypropylene, polycarbonate and acrylonitrile butadiene styrene polymer. The break-away sheath may be at least a part of a molded piece, which may be an injection molded piece. The exterior of the break-away sheath may taper to a narrower exterior width adjacent the distal end of the sheath tool. The second internal passage of the sheath tool may have a minimum width in a range having a lower limit of 0.7, 0.8 or 1 millimeter and an upper limit of 3, 2.5 or 2 millimeters. The second internal passage of the sheath tool may have a minimum width of no more than 0.1 millimeter, no more than 0.2 millimeter, no more than 0.25 millimeter or no more than 0.3 millimeter larger than a maximum exterior width of a portion of the working member configured to pass through the second internal passage and to exit the second internal passage at a distal end of the break-away sheath. The sheath tool may comprise tab portions adjacent the proximal end of the sheath tool for manually manipulating the sheath tool and/or for exerting a force to commence break-away removal of the break-away sheath.

The implant device may comprise a conduit extending from adjacent the proximal end to adjacent the distal end of the implant device and configured for being disposed through a fistula when the implant device is implanted with a proximal end disposed in the lacrimal apparatus. The conduit may have an exterior width transverse to the length of the implant device, and the break-away sheath may have a maximum exterior width that is at least as large as a maximum exterior width of the conduit of the implant device. The maximum exterior width of the break-away sheath may be at least 0.1, 0.2, 0.25 or 0.5 millimeter larger than the maximum exterior width of the conduit of the implant device. The maximum exterior width of the break-away sheath may be larger than the maximum exterior width of the conduit of the implant device by no more than 2 millimeters, no more than 1 millimeter or no more than 0.75 millimeter. The maximum exterior width of the conduit of the implant device may be in a range having a lower limit of 1.5 millimeters or 2 millimeters and an upper limit of 3 millimeters, 2.75 millimeters or 2.5 millimeters.

Some other possible additional features and feature refinements applicable to the implant device in relation to any of the first aspect, second aspect or third aspect of the invention are now summarized.

The implant device may have a conduit that extends from adjacent the proximal end to adjacent the distal end. The first internal passage of the implant device may extend between the proximal end and the distal end, and including through the conduit. The first internal passage may have a first end open at the proximal end of the implant device and a second end open at the distal end of the implant device. The implant device may include a length longitudinally along the device between the proximal end and the distal end that is in a range of from 2 millimeters to 50 millimeters. A width of the first internal passage transverse to the length may be in a range of from 0.25 millimeter to 5 millimeters. The implant device may be configured to be implanted to fluidly connect the lacrimal apparatus to the paranasal sinus through the fistula so that when the implant device is implanted: the proximal end is disposed with the first end of the first internal passage opening in the lacrimal apparatus; the distal end is disposed in the paranasal sinus with the second end of the first internal passage opening in the paranasal sinus; and the conduit is disposed through the fistula.

The implant device may have a conduit configured so that an exterior of the conduit comprises an anchoring surface feature which assists to anchor the implant device when the device is implanted. The anchoring surface feature includes protrusion areas and recess areas. The implant device may be configured so that when implanted the conduit is disposed through the fistula with at least a portion of the recess areas disposed within the fistula and with at least a portion of the protrusion areas disposed in the fistula and engaging tissue exposed within the fistula to anchor the implant device. The structural and mechanical characteristics of protrusion occurrences in the protrusion areas may affect anchoring performance of the protrusion areas. The height of the protrusion areas relative to the recess areas may affect anchoring effectiveness when the implant device is implanted. A larger height may provide greater anchor effectiveness, but also may involve a larger overall width of the implant device that must be inserted into the fistula. The protrusion areas may have a height relative to the recess areas of at least 0.1 millimeter, at least 0.2 millimeter, at least 0.25 millimeter or at least 0.3 millimeter. The protrusions areas may have a height relative to the recess areas of no greater than 2 millimeters, no greater than 1.5 millimeter, no greater than 1 millimeter, no greater than 0.75 millimeter, no greater than 0.5 millimeter or no greater than 0.4 millimeter. The height may be of particular protrusion occurrences relative to adjacent areas of recesses. Protrusion occurrences are also referred to herein as anchor protrusions. Such anchor protrusions may be configured to flexibly deform when the conduit is inserted through the fistula for implantation, for example to flexibly deform in a direction opposite the direction of insertion when the anchor protrusions contact tissue disposed in the fistula during insertion. After insertion, the anchor protrusions may over time return to their original shape and extend deeper into adjacent tissue to better anchor the implant device. The mechanical properties of the anchor protrusions may be influenced by materials of construction. Preferred materials of construction for the protrusion areas, and also for the portions of the implant device, are polymeric materials. The polymeric materials may preferably be medical grade materials. Some preferred polymeric materials are silicones and polyurethanes. For enhanced performance, the material of construction should have a rigidity that interacts positively with tissue in the vicinity of the fistula, for example to promote load sharing and good anchoring. One preferred material of construction is a polymeric material (e.g. silicone or polyurethane) having a durometer (Shore A) in a range having a lower limit of 50, 60, 70 or 80 and an upper limit of 100, 80, 70 or 60, provided that the upper limit must be larger than the lower limit. One preferred range is for a durometer (Shore A) of 60-100, with a range of 80-100 being even more preferred. For some implementations the polymeric material has a durometer (Shore A) of about 60, of about 80 or of about 100. Mechanical properties of the protrusion occurrences of the protrusion areas will also be affected by the geometry of the protrusion occurrences. The protrusion occurrences may have a width that tapers, or narrows, in a direction from a base toward a top of the protrusion occurrences, with the base being a portion of a protrusion occurrence disposed toward the first internal passage of the conduit and a top of the protrusion occurrence being the extremity of the protrusion occurrence away from the first internal passage of the conduit. The width may be transverse to the length of the conduit. The protrusion occurrences may have a width at the base that is no larger than 2 millimeters, no larger than 1.5 millimeters, no larger than 1.25 millimeters or no larger than 1 millimeter. One or more of the protrusion occurrences may have a width at the base that is at least 0.2 millimeter, at least 0.3 millimeter, at least 0.5 millimeter, at least 0.75 millimeter or at least 1 millimeter. The protrusion occurrences may have a width adjacent the top that is no larger than 0.75 times width at the base, no larger than 0.5 times the width at the base, or no larger than 0.25 times the width at the base. The protrusion occurrences may have a width midway between the base and the top that is no larger than 0.8 times the width of the base, no larger than 0.7 times the width of the base, no larger than 0.6 times the width of the base or no larger than 0.5 times the width at the base.

The protrusion areas may be provided by a single protrusion occurrence feature located to correspond with the interior of the fistula when the implant device is implanted. In more preferred implementations, the protrusion areas include multiple protrusion occurrences spaced on the exterior of the conduit. The protrusion occurrences may have a center-to-center spacing, in one or more directions, of at least 0.5 millimeter, at least 0.75 millimeter, at least 1 millimeter or at least 1.75 millimeters. The protrusion occurrences may have a center-to-center spacing of no greater than 2.5 millimeters, no greater than 2 millimeters or no greater than 1.75 millimeters. The protrusion occurrences may have a center-to-center spacing longitudinally along the conduit. The protrusion occurrences may have a center-to-center spacing that is at least 0.5 times the base width of the protrusion occurrences, or at least 1 times the base width of the protrusion occurrences or at least 2 times the base width of the protrusion occurrences. The protrusion occurrences may have a center-to-center spacing that is no more than 5 times a base width of the protrusion occurrences, no more than 3 times a base width of the protrusion occurrences or no more than 2 times a base width of the protrusion occurrences.

The protrusion areas may be located on a longitudinal portion of the conduit that includes at least a portion of the conduit that will be disposed within a fistula when the implant device is implanted. The protrusion areas may be on a longitudinal portion of the conduit that extends for at least 2 millimeters along the length of the implant device, that extends for at least 3 millimeters along the length of the implant device, that extends for at least 4 millimeters along the length of the implant device, that extends for at least 5 millimeters along the length of the implant device or that extends for at least 8 millimeters along the length of the implant device. A longitudinal portion of the conduit including the protrusion areas may be no longer than 20 millimeters, no longer than 15 millimeters or no longer than 10 millimeters. A longitudinal portion of the conduit including the protrusion areas may be disposed at least 2 millimeters from the proximal end of the device, at least 3 millimeters from the proximal end of the device, or at least 4 millimeters from the proximal end of the device. When the implant device has a head, a longitudinal portion of the conduit including the protrusions may be disposed at least 1 millimeter, at least 2 millimeters or at least 3 millimeters from the head. Providing significant distance between the head and commencement of the protrusion areas permits the head to better "float" on the surface of tissue, which may enhance patient comfort and device performance. The protrusion areas may be disposed along a longitudinal portion of the conduit with the protrusion areas covering no more than 35% of the area along that longitudinal portion of the conduit, no more than 25% of the area along that longitudinal portion of the conduit or not more than 20% of the area along that longitudinal portion of the conduit. Providing significant spacing between protrusion occurrences may permit better engagement of tissue by the anchoring surface feature.

The protrusion areas may comprise at least one circumferential ridge. By circumferential ridge is meant a ridge that extends around an entire circumference of the conduit. The protrusion area may comprise at least two, at least three or at least five circumferential ridges. The protrusion areas may comprise a spiral ridge. Such a spiral ridge may extend along a longitudinal portion of the conduit. The protrusion areas may comprise a knob or may comprise multiple knobs. The anchoring surface feature may comprise a textured surface, with the protrusion areas comprising protruding portions of the textured surface and the recess areas comprising recess portions of the textured surface.

The implant device may comprise a distal anchoring or retention feature that will be disposed in the paranasal sinus when implanted. Such a distal feature may include, for example, barbs or other features configured to be disposed distal of the fistula and in the paranasal sinus when the implant device is implanted and to provide a barrier to removal of the implant device from the fistula by withdrawal from the proximal end of the fistula. Such a feature may automatically deploy on insertion through the fistula. Such a distal feature may be used with or without use also of anchor protrusions to engage tissue within the fistula, and such a distal feature may extend peripherally beyond a peripheral extend of such anchor protrusions when the implant device also includes such anchor protrusions for engaging tissue within the fistula.

The length of the implant device may be selected within the general range stated above to provide sufficient conduit length for extending through the entire length of the fistula plus any extension distance desired in the lacrimal apparatus proximal to the fistula and in the paranasal sinus distal to the fistula. The length of the conduit may be in a range having a lower limit of 2 millimeters, 3 millimeters, 4 millimeters, 5 millimeters or 8 millimeters and an upper limit of 50 millimeters, 40 millimeters, 30 millimeters, 20 millimeters, 15 millimeters or 10 millimeters. One preferred range for some implementations when the fistula is between the orbit and the ethmoid sinus or the maxillary sinus is for the length of the implant device to be in a range of from 5 millimeters to 20 millimeters, with a range of from 8 millimeters to 15 millimeters being more preferred. By length of the implant device it is meant the dimension longitudinally along the device from the proximal end to the distal end, and may be along a longitudinal axis through the first internal passage. The length may be a straight line, for example when the first internal passage is straight, or the length may be curvilinear or some other shape, for example when the first internal passage is not linear. When a reference is made herein to transverse to the length, the reference is to a right angle to the longitudinal direction of the length at that point (e.g., right angle to a line of the length or to a line tangent to a curve of the length).

The implant device may advantageously be designed with a conduit of appropriate width dimensions to fit snuggly within a desired size of fistula. The implant device may have a first exterior width dimension defined by a maximum extent of the protrusion areas transverse to the length of the device, with the exterior width being within a range having a lower limit of 0.75 millimeter, 1 millimeter, 1.25 millimeters, 1.5 millimeters, 1.75 millimeters or 2 millimeters and an upper limit of 8 millimeters, 7 millimeters, 6 millimeters, 5 millimeters, 4 millimeters, 3 millimeters, 2 millimeters or 1.75 millimeters, provided of course that the upper limit must be larger than the lower limit. The conduit may have a second width dimension defined by the minimum extent of the recess areas transverse to the length of the device, and which second exterior width dimension will be smaller than the first exterior width dimension defined by the protrusion areas. The second exterior width dimension defined by the recess areas may be smaller than the exterior width dimension defined by the protrusion areas by an amount within a range having a lower limit of 0.2 millimeter, 0.25 millimeter, 0.35 millimeter or 0.5 millimeter and having an upper limit of 1.5 millimeters, 1 millimeter or 0.75 millimeter. The height of the protrusion areas may be one-half the difference between the first exterior width and the second exterior width. Either one of or each one of the first exterior width and the second exterior width may be the diameter of a circle.

The implant device may comprise a plurality of apertures through a wall of the conduit to provide fluid communication from outside of the conduit to the first internal passage in the conduit. The apertures may be located on a portion of the conduit designed to be distal to the fistula and located in a paranasal sinus when the implant device is implanted. Some or all of the apertures may be located along the length of the device at least 5 millimeters from the proximal end, at least 8 millimeters end from the proximal end or at least 10 millimeters from the proximal end. The width of such an aperture may be equal to or may be smaller than a width of the portion of the first internal passage into which the aperture opens.

The implant device may include a head adjacent to the conduit at the proximal end of the implant device. The implant device may be configured so that when the implant device is implanted, the head is disposed in the lacrimal apparatus, and preferably with the head located in the orbit. The head may beneficially keep the implant device from migrating through the fistula toward the paranasal sinus following implantation of the implant device. The head may comprise a flanged tissue engagement surface on a side of the head disposed toward the conduit and configured to engage tissue outside of and adjacent to the fistula when the implant device is implanted. The flanged tissue engagement surface may be a flat surface. The flanged tissue engagement surface may have non-flat surface features configured to improve seating of the surface against tissue, such as for example to inhibit rotation of the implant device within the fistula after implantation. The head may have a face surface opposite the flanged tissue engagement surface and also disposed away from the conduit and disposed away from tissue engaged by the flanged tissue engagement surface when the implant device is implanted. The face surface may be substantially flat. The face surface may be disposed at the proximal end of the implant device and the first internal passage may open at the face surface. The separation distance between the face surface and the flanged tissue engagement surface may be in a range having a lower limit of 0.25 millimeter, 0.5 millimeter or 0.75 millimeter and having an upper limit of 2 millimeters, 1.5 millimeters or 1 millimeter. Such separation distance need not be constant across the flanged tissue engagement surface and face surface. A maximum separation distance between the face surface and the flanged tissue engagement surface may be referred to as the depth of the head, and such depth may be in a range described above for the separation distance between the face surface and the flanged tissue engagement surface. The flanged tissue engagement surface need not be continuous and may be divided into multiple distinct surface portions. For example, the flanged tissue engagement surface may include a first flanged portion disposed to one side of the first internal passage and a second flanged surface portion disposed to a second side of the first internal passage that is opposite the first side. Each of the face surface and the flanged tissue engagement surface may have a length dimension that represents a maximum separation distance between points on an outer edge of the respective surface, and may each have a width dimension that is a maximum separation distance between points on the outer edge transverse to the length dimension. The length dimensions of the face surface and the flanged tissue engagement surface may be the same or may be different. The width dimensions of the face surface and the flanged tissue engagement surface may be the same or may be different. The face surface and the flanged tissue engagement surface may have corresponding outer edges. The length dimension of any or all of the face surface, the flanged tissue engagement surface and the head may be larger than a first exterior width of the conduit defined by an extent of the protrusion areas transverse to the length of the implant device, when the implant device includes an anchoring surface feature such as summarized above. The length dimension of any or all of the face surface, the tissue engagement surface and the head may be in a range having a lower limit of 1 millimeter, 2 millimeters, 3 millimeters, 4 millimeters or 5 millimeters and an upper limit of, 10 millimeters, 8 millimeters or 7 millimeters. The width dimension of any or all of the face surface, tissue engagement surface and the head may be in a range having a lower limit of 0.5 millimeter, 1 millimeter, 1.5 millimeters or 2 millimeters and an upper limit of 5 millimeters, 4 millimeters or 3 millimeters. The length dimension of any or all of the face surface, the flanged tissue engagement surface and the head may be at least 1 millimeter, at least 2 millimeters, at least 3 millimeters or at least 4 millimeters larger than such first exterior width of the conduit defined by an extent of the protrusion areas, when the implant device includes an anchoring surface feature such as summarized above. A ratio of the length of any of or all the face surface, the flanged tissue engagement surface and the head to such a first exterior width of the conduit may be at least 2. Such a ratio may be smaller than 4. The width of any or all of the face surface, the flanged tissue engagement surface and the head may be not larger than, or may be smaller than (e.g., by at least 0.1 mm or by at least 0.2 mm), such a first exterior width of the conduit defined by an extent of the protrusion areas, when the implant device includes an anchoring surface feature such as summarized above. A ratio of the length dimension to the width dimension for any or all of the face surface, the flanged tissue engagement surface and the head may be in a range having a lower limit of 1, 1.5, 2 or 2.5 and an upper limit of 5, 4, 3 or 2.5, provided of course that the upper limit must be larger than the lower limit. Having a larger length dimension to width dimension on the head is particularly preferred when the head will be located in the orbit between the lacrimal caruncle and the plica semilunaris, because the length dimension may advantageously align in a vertical direction next to the eyeball and will help provide sufficient flanged surface area to effectively anchor the implant device on the proximal end and impede conjunctival tissue from covering the opening into the first internal passage of the implant device, compensating for the narrower width. This is particularly advantageous when using polymeric materials of construction as described above.

The first internal passage through the implant device may have a substantially uniform shape along the entire length of the implant device, or may have a varying shape. The first internal passage may be substantially straight from the proximal end of the device to the distal end of the device. The first internal passage may have a cross-section available for flow (transverse to the length of the device) that is substantially uniform from the proximal end to the distal end of the implant device. The first internal passage may have a substantially circular cross-section. The first internal passage may have a substantially elliptical cross-section. The width of the conduit (maximum dimension across the cross-section of the first internal passage available for flow) may be in a range having a lower limit of 0.25 millimeter, 0.5 millimeter or 0.75 millimeter and 1 millimeter and an upper limit of 5 millimeters, or 4 millimeters or 3 millimeters, 2 millimeters or 1.5 millimeters.

The implant device may be configured for implantation with the conduit passing through a fistula between a location in a lacrimal apparatus within the orbit and a paranasal sinus selected from the group consisting of a frontal sinus, an ethmoid sinus, a maxillary sinus and a sphenoid sinus, with a frontal sinus, a maxillary sinus or an ethmoid sinus being preferred, with an ethmoid sinus or a maxillary sinus being more preferred, and with an ethmoid sinus being particularly preferred. The implant device may be configured for implantation with the conduit passing through a fistula between a location in the lacrimal apparatus within the nasolacrimal duct and a paranasal sinus selected from the group consisting of an ethmoid sinus and a maxillary sinus. The location within the nasolacrimal duct may be within the lacrimal sac.

The implant device is primarily configured for and described herein with primary reference to the implant device being implantable in a fistula that may be formed between the lacrimal apparatus and a paranasal sinus to provide a passage from the lacrimal apparatus to the paranasal sinus. The implant device is also implantable in a fistula that may be formed between the lacrimal apparatus (e.g., from the corner of medial portion of the orbit between the lacrimal caruncle and the plica semilunaris) and the nasal cavity, for example for enhanced drainage of lacrimal fluid, and such applications directed to the nasal cavity are within the scope of the different aspects of the invention.

BRIEF DESCRIPTION OF THE DRAWINGS

FIG. 11 is an illustration of various head configurations for an implant device.

DETAILED DESCRIPTION

Figure 1:
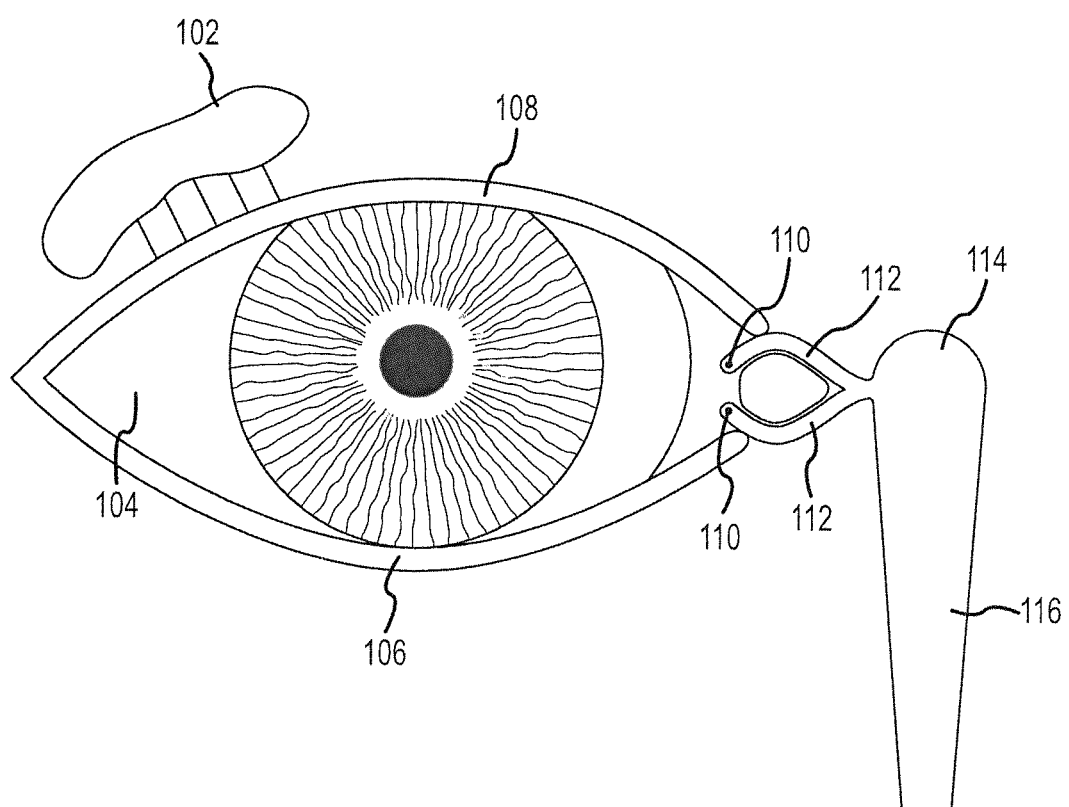
FIG. 1 is an illustration showing components of the lacrimal apparatus.

The terms "lacrimal apparatus" and "lacrimal system" are used interchangeably herein to refer to the collection of physiological components that accomplish the production and secretion of lacrimal fluid to lubricate the eyeball, containment of lacrimal fluid in a reservoir of lacrimal fluid in the orbit and drainage of lacrimal fluid from the orbit to the nasal cavity. The lacrimal apparatus includes the lacrimal glands, the tear drainage system and the reservoir of lacrimal fluid located between the lacrimal glands and the tear drainage system. The reservoir of lacrimal fluid includes the eyelid margins and the conjunctival sac (and including the pool of tears in the lower conjunctival cul-de-sac that is sometimes referred to as the lacrimal lake). The tear drainage system includes the puncta, canaliculi and nasolacrimal duct (including the so-called lacrimal sac located at the top of the nasolacrimal duct) through which excess tears drain to Hasner's valve and into the nasal cavity. FIG. 1 shows generally the lacrimal apparatus. Lacrimal fluid is produced and secreted from lacrimal glands 102 to lubricate the surface of the eyeball 104 disposed within the orbit. Lacrimal fluid forms a coating over the eyeball 104 and is generally contained within the conjunctival sac (the space between the lower eyelid 106, upper eyelid 108 and eyeball 104 that is lined by the conjunctiva). Excess lacrimal fluid is conducted to the vicinity of the medial canthus (medial corner of the eye) and drains through the lacrimal puncta 110 into the lacrimal canaliculi 112 and into the lacrimal sac 114 of the nasolacrimal duct 116. The lacrimal fluid then drains from the nasolacrimal duct 116 through Hasner's valve and into the nasal cavity.

Figure 2:
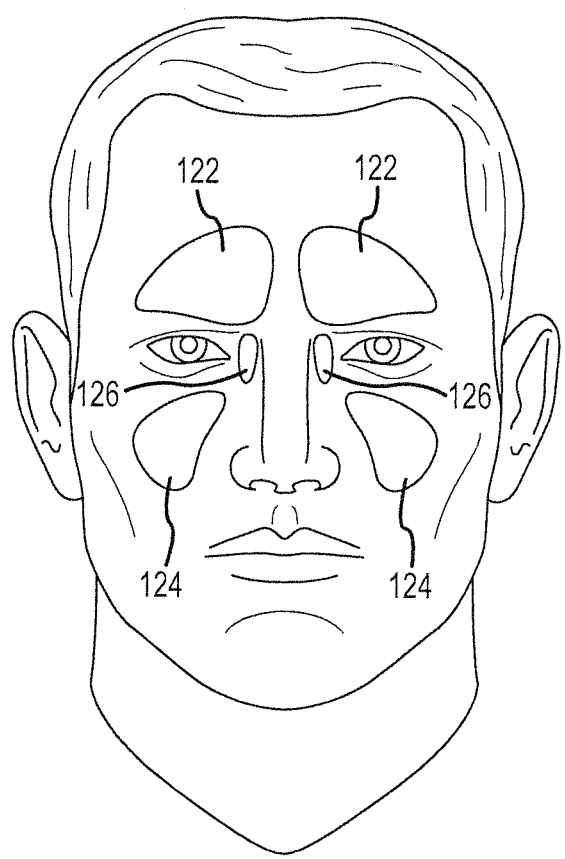
FIG. 2 is an illustration showing general locations of paranasal sinuses.
Figure 3:
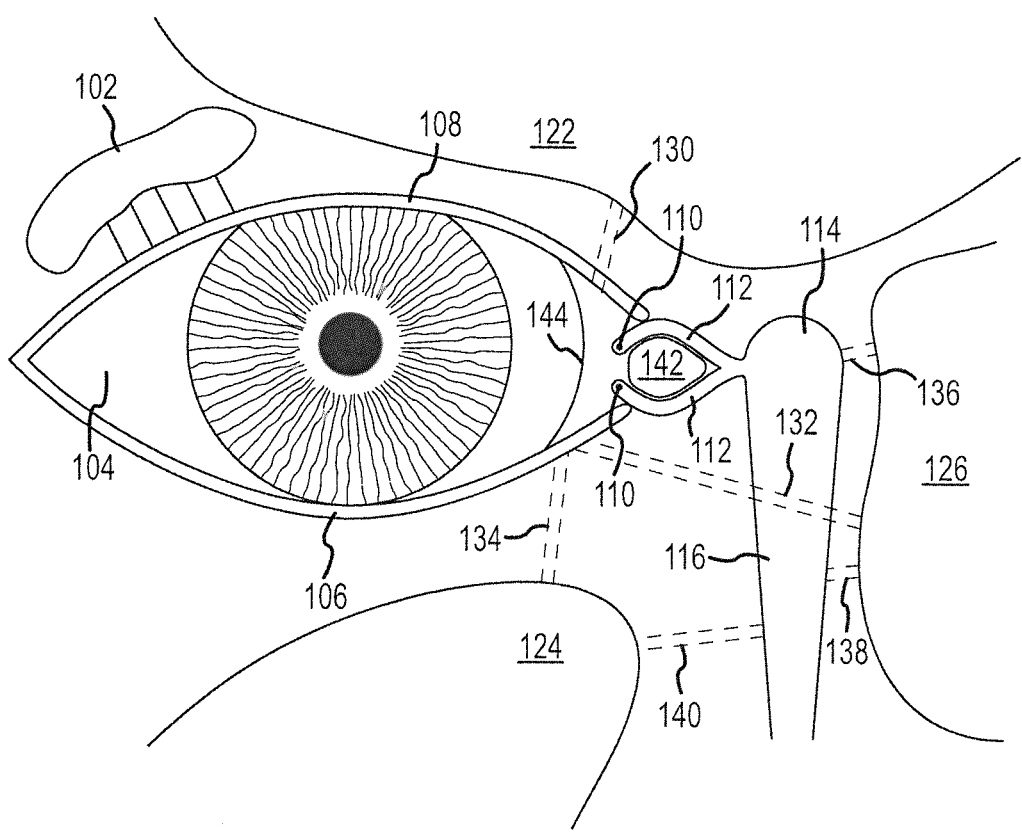
FIG. 3 is an illustration showing some example routes for fistulas between the lacrimal apparatus and the paranasal sinuses.
Figure 4:
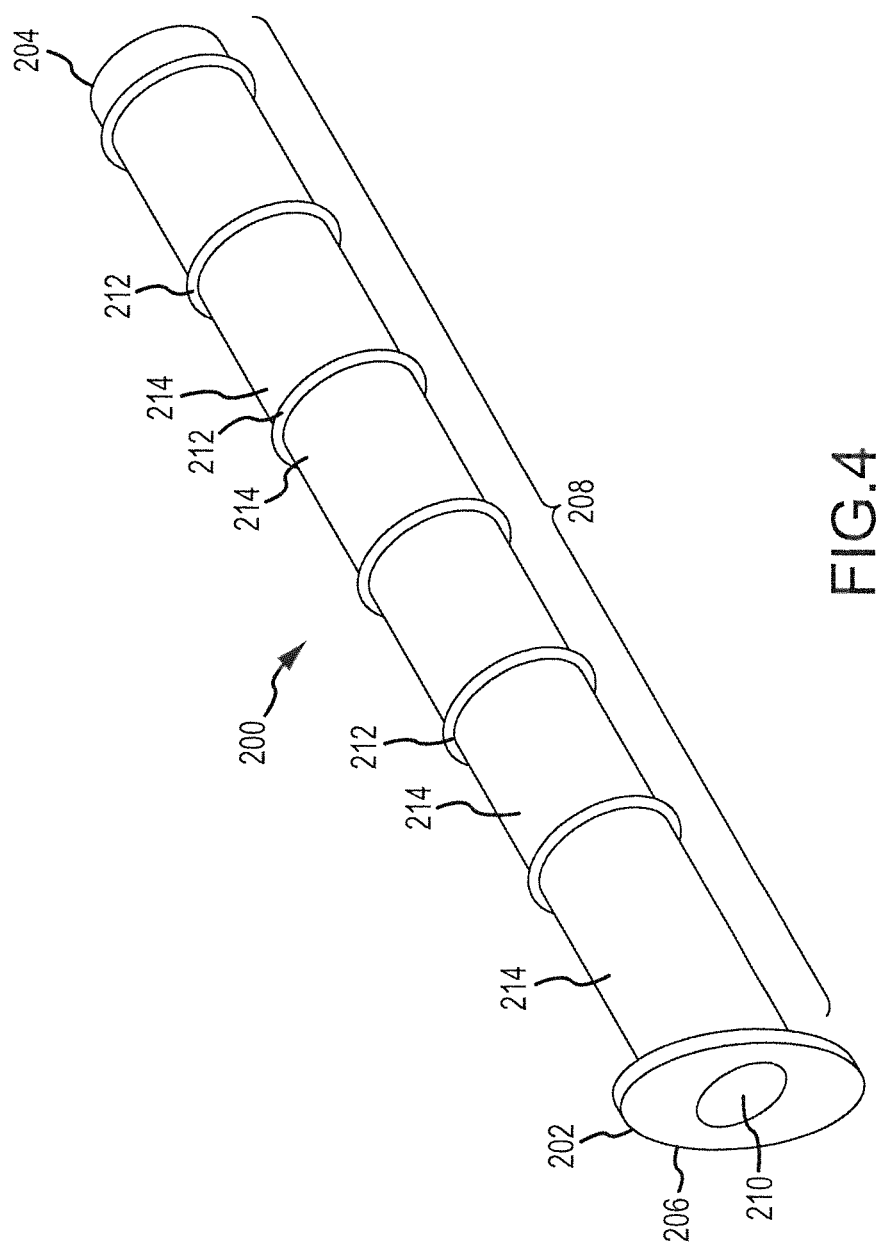
FIG. 4 is perspective view of one embodiment of an implant device.
Figure 5:
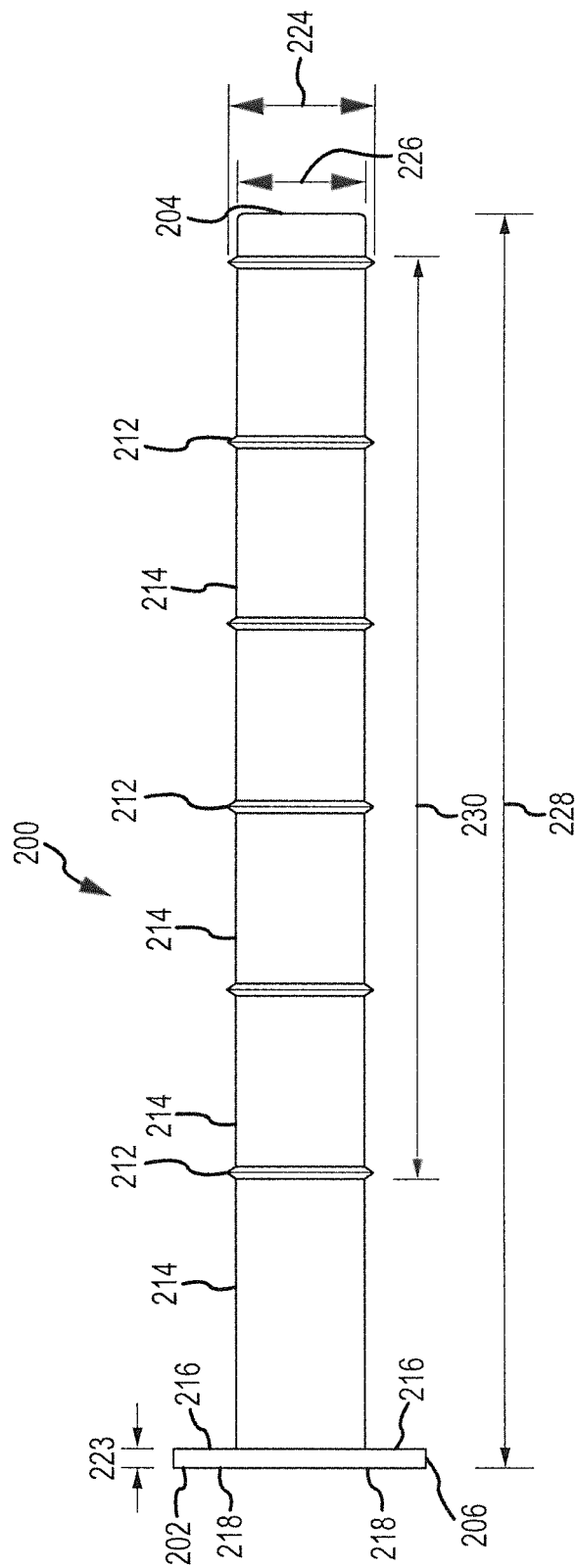
FIG. 5 is a side view of the same embodiment of an implant device as shown in FIG. 4.
Figure 6:
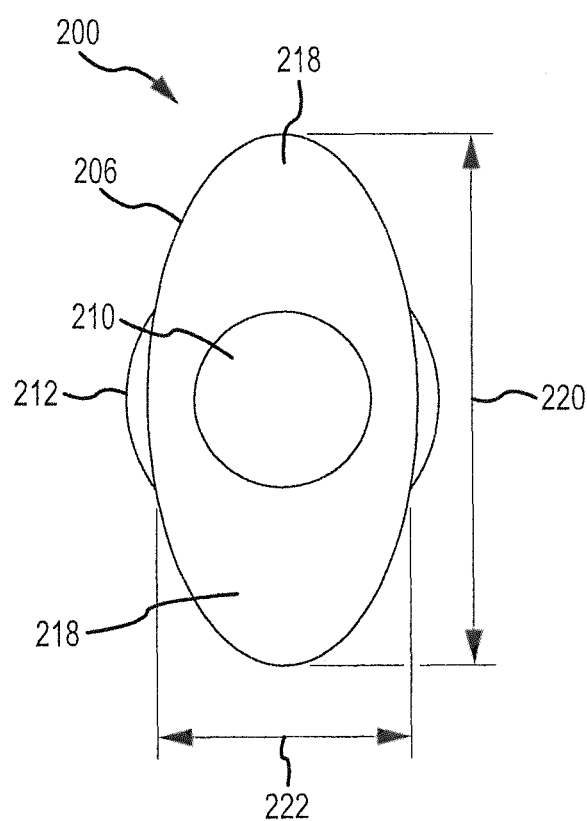
FIG. 6 is an end view of the same embodiment of an implant device as show in FIG. 4.
Figure 7:
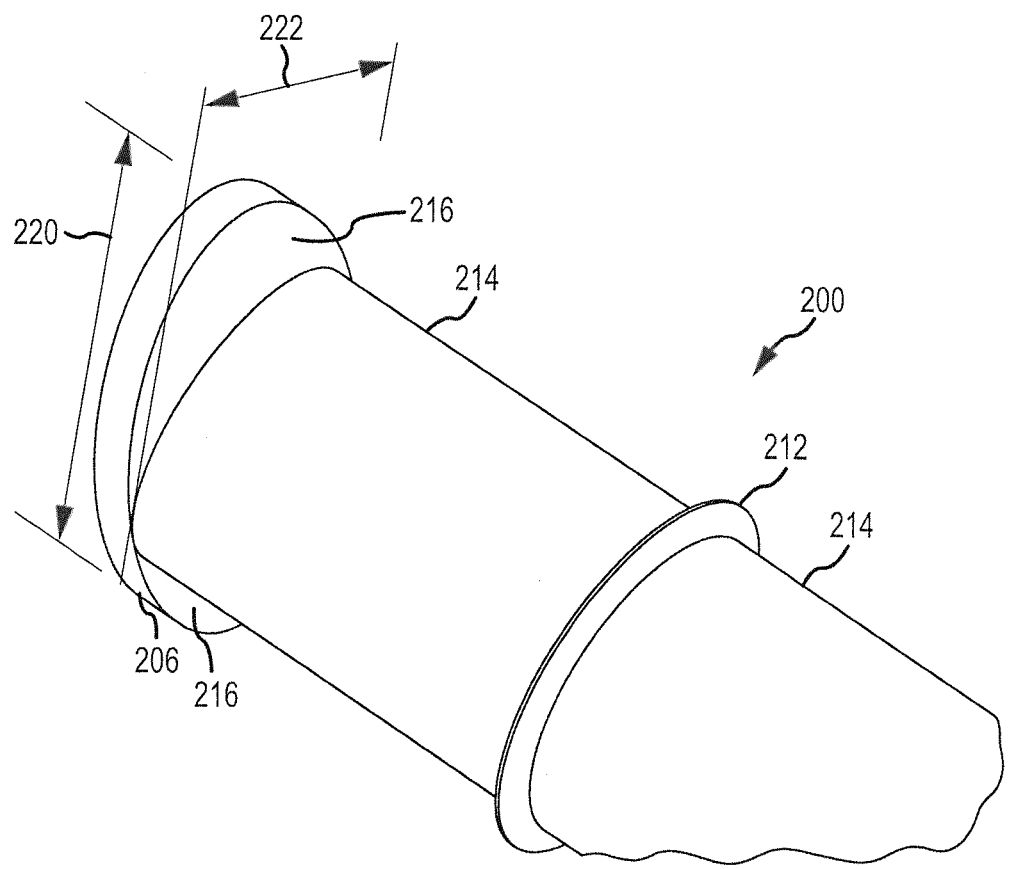
FIG. 7 is a partial perspective view of the same embodiment of an implant device as shown in FIG. 4.

As used herein, a fistula between the lacrimal apparatus and a paranasal sinus refers to an artificially-created passage that fluidly connects the lacrimal apparatus with the paranasal sinus. The paranasal sinuses include the frontal sinuses, maxillary sinuses, ethmoid sinuses and sphenoid sinuses, which are cavities contained within frontal, maxilla, ethmoid and sphenoid bones, respectively. The paranasal sinuses drain into the nasal cavity. FIG. 2 is a schematic of a human head showing generally the locations of the frontal sinuses 122, the maxillary sinuses 124 and the ethmoid sinuses 126. The sphenoid sinuses (not shown) are located generally behind the ethmoid sinuses 126. FIG. 3 shows generally some possible routes for a fistula between the lacrimal system and a paranasal sinus. Reference numerals indicate the same features as shown in FIGS. 1 and 2, except as noted. FIG. 3 shows the general proximity of the frontal sinus 122, maxillary sinus 124 and ethmoid sinus 126 relative to features of the lacrimal apparatus. Some example fistula routes are shown in FIG. 3 by dashed lines. A first example fistula route 130 is from the orbit to the frontal sinus. A second example fistula route 132 is from the orbit to the ethmoid sinus 126. A third example fistula route 134 is from the orbit to the maxillary sinus 124. A fourth example fistula route 136 is from the lacrimal sac 114 at the top of the nasolacrimal duct 116 to the ethmoid sinus 126. A fifth example fistula route 138 is from the nasolacrimal duct 116 at a location below the lacrimal sac 114 to the ethmoid sinus 126. A sixth example fistula route 140 is from the nasolacrimal duct 116 at a location below the lacrimal sac 114 to the maxillary sinus 124. The example fistula routes shown in FIG. 3 are for purposes of general illustration only and not show precise locations where a fistula might be formed to connect a part of the lacrimal apparatus with the corresponding paranasal sinus. Although not shown in FIG. 3, example fistula routes to the sphenoid sinus include from the orbit to the sphenoid sinus and from the nasolacrimal duct 116 to the sphenoid sinus. Forming a fistula to connect to the sphenoid sinuses is generally not as preferred as forming a fistula to connect to the ethmoid sinus, for example because it is generally more convenient and direct to connect with the ethmoid sinus. Also, forming a fistula to either the ethmoid sinus 126 or the maxillary sinus 124 is generally preferred to forming a fistula to the frontal sinus 122, with one reason being that a fistula between the lacrimal system and either the ethmoid sinus 126 or the maxillary sinus 124 may be formed in a way to obtain the benefit of gravity to assist drainage of lacrimal fluid from the lacrimal system into the corresponding paranasal sinus through the fistula. The frontal sinus is located generally above the orbit and will not benefit in the same way from gravity drainage of lacrimal fluid into the paranasal sinus. However, gravity drainage may beneficially assist drainage of fluid from the frontal sinus.

With continued reference to FIG. 3, the first, second and third example fistula routes 130, 132 and 134 are subconjuctival routes that penetrate the conjunctiva to directly connect the lacrimal fluid reservoir within the conjunctival sac to the corresponding paranasal sinus. A fistula along such a subconjunctival route may be surgically formed by a surgical tool piercing through the conjunctiva and the adjacent wall of the bone in which is disposed the corresponding paranasal sinus. For example, for the first example fistula route 130, the fistula would pass subconjunctivally from the orbit and through a wall of the frontal bone into the frontal sinus 122. For example, a fistula following second example fistula route 132 would pass subconjunctivally from the orbit and through a wall of the ethmoid bone into the ethmoid sinus 126. For example, a fistula following the third example fistula route 134 would pass subconjunctivally from the orbit through a wall of the maxilla bone into the maxillary sinus 124. Subconjuctival routes for a fistula such as those of the first, second and third example fistula routes 130, 132 and 134 are generally preferred as being formed at locations that are relatively easy to access. In a preferred implementation of the first, second and third example fistula routes 130, 132 and 134, the proximal end of the fistula opening into the orbit is located between the lacrimal caruncle 142 and the plica semilunaris 144, shown in FIG. 3.

Continuing with reference to FIG. 3, a fistula at the fourth, fifth or sixth example fistula routes 136, 138 and 140 will have a proximal end opening into a location within the nasolacrimal duct 116. Formation of a fistula in such a location requires insertion of a surgical tool into the lacrimal drainage system, such as through the puncta 110 and canaliculi 112 to access the nasolacrimal duct 116 or through the nose to access the nasolacrimal duct 116. For example, a fistula at the fourth example fistula route 136 may be formed by a piercing instrument (e.g., a trocar or trocar/cannula assembly) inserted into one of the puncta 110, through one of the canaliculi 112 and across the lacrimal sac 114 to pierce a hole at the location of the fourth example fistula route 136. As another example, a fistula may be formed at one of the fourth, fifth and sixth example fistula routes 136, 138 and 140 using a guide wire inserted into one of the puncta 110, through one of the canaliculi 112, into the lacrimal sac 114 and downward through the nasolacrimal duct 116. The guide wire may be used to engage a surgical tool and to guide the surgical tool from the nose through Hasner's valve (not shown) and to the appropriate location within the nasolacrimal duct 116 to permit performance of a surgical operation at that location to form the desired fistula.

FIGS. 4-7 show one embodiment of an implant device. As shown in FIGS. 4-7, an implant device 200 has a proximal end 202 and a distal end 204 located on opposite longitudinal ends of the implant device 200. The implant device 200 includes a head 206 at the proximal end 202 and a conduit 208 extending from the head 206 to the distal end 204. An internal passage 210 extends from the proximal end 202 to the distal end 204, passing through the head 206 and the conduit 208. The internal passage 210 opens at the proximal end 202 and the distal end 204, thereby providing a passage through the entire longitudinal length of the implant device 200. The internal passage 210 of the embodiment shown in FIG. 4 has a cylindrical shape with a uniform circular cross-section (transverse to the length of the implant device 200), and the width of the internal passage is equal to the diameter of the circle of the cross-section and is uniform along the length of the implant device 200. The length of the implant device 200 is the minimum distance longitudinally along the implant device 200 between the proximal end 202 and the distal end 204, and will typically be equal to the distance along an axis of the internal passage 210 from the proximal end 202 to the distal end 204. The implant device 200 includes multiple anchor protrusions 212 on an exterior of the conduit 208. In the embodiment shown in FIGS. 4-7, the anchor protrusions 212 are in the form of spaced circumferential ridges that each extends around the entire circumference of the conduit 208. Adjacent the circumferential ridges of the anchor protrusions 212 are areas of recess 214 on the exterior of the conduit 208.

With continued reference to FIGS. 4-7, when the implant device is implanted to fluidly connect the lacrimal apparatus to a paranasal sinus through a fistula, the head 206 is disposed in the lacrimal apparatus and the proximal end 202 is disposed in the paranasal sinus, and with at least a portion of the conduit 208 disposed through the fistula with at least one, and preferably more than one, of the anchor protrusions 212 engaging tissue within the fistula to anchor the implant device 200. When implanted in this manner, the internal passage 210 opens into the lacrimal apparatus at the proximal end 202 and into the paranasal sinus at the distal end 204. The head 206 has a flanged tissue engagement surface 216 on a side of the head 206 disposed toward the conduit 208, and which flanged tissue engagement surface 216 is advantageously configured to engage tissue adjacent the proximal end of fistula and to prevent the proximal end 202 of the implant device 200 from migrating into the fistula following implantation. On the side of the head 206 opposite the flanged tissue engagement surface 216 is a face surface 218 of the head 206, which face surface 218 is disposed away from tissue engaged by the flanged tissue engagement surface 216 when the implant device is implanted. The head 206 has a first dimension 220 and a second dimension 222 on both the flanged tissue engagement surface 216 and the face surface 218. The first dimension 220 is the length of the respective surface and the second dimension is the width of the respective surface. Such length and width dimensions may also be referred to as major and minor dimensions. The first dimension 220 of a surface 216 or 218 corresponds to the maximum separation distance between points on the outer edge of the surface, and the second dimension 222 of the surface 216 or 218 corresponds to the maximum separation distance between points on the outer edge of the surface that are on a line transverse to the first dimension. Conveniently, the face surface 218 and the flanged tissue engagement surface 216 may be made with corresponding outer edges, so that the opposing surfaces 216 and 218 have substantially equal length and width dimensions, although such is not required. The first dimension 220 and the second dimension 222 may be referred to generally as the length and width, respectively, of the head 206 when the surfaces 216 and 218 have corresponding shapes, as is the case for the embodiment shown in FIGS. 4-7. When the surfaces 216 and 218 do not have corresponding shapes, the length and width dimensions of the head will be different from one or more of the length and width dimensions of the surfaces 216 and 218. The head 206 has a depth dimension 223 between surfaces 216 and 218. The depth dimension 223 should preferably be kept to a small value so that the head 206 will have a low profile adjacent the proximal end of the fistula when the implant device 200 is implanted with the flanged tissue engagement surface engaging tissue adjacent the proximal end of the fistula.

With continued reference to FIGS. 4-7, the conduit 208 has a first exterior width 224 that is a maximum exterior width of the conduit 208 as defined by the maximum extents of the anchor protrusions 212 transverse to the length of the conduit 208. The conduit 208 has a second exterior width 226 that is a minimum exterior width of the conduit 208 defined between the most recessed portions of the areas of recess 214. In the embodiment shown in FIGS. 4-7, the height of the anchor protrusions 212 is equal to one-half the difference between the first exterior width 224 and the second exterior width 226 of the conduit 208. In the configuration of the head 206 shown in FIG. 4-7, the first dimension 220 of the head is larger than both the first exterior width 224 and the second exterior width 226 of the conduit 208, while the second dimension 222 of the head is approximately equal to the second exterior width 224 of the conduit 208.

With continued reference to FIGS. 4-7, the anchor protrusions 212 are in the form of circumferential ridges having a width that is at a maximum at the bottom of the ridges located adjacent the areas of recess 214, and which width tapers to a minimum at the top of the ridges 212 located away from the recess areas 214. Other configurations for anchor protrusions are possible, and all anchor protrusions on an implant device need not be of the same size, geometry or height. Likewise, areas of recess may have varying configurations, and not all recesses on an implant device need to be the same size or configuration. The implant device 200 has a length 228 including the depth 223 of the head 206 and the length of the conduit 208. The anchor protrusions 212 are on a longitudinal portion 230 of the conduit 208.

Figure 8:
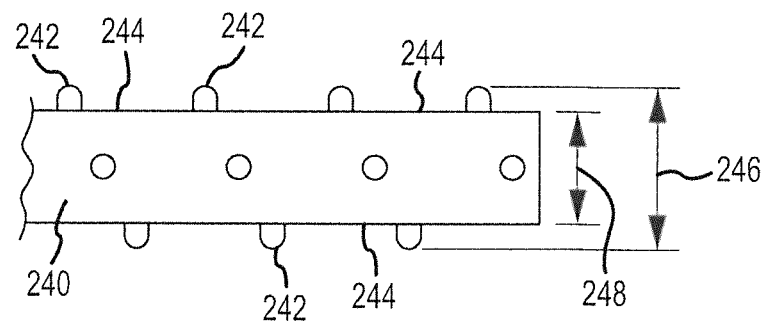
FIG. 8 is a partial side view of an embodiment of an implant device.
Figure 9:
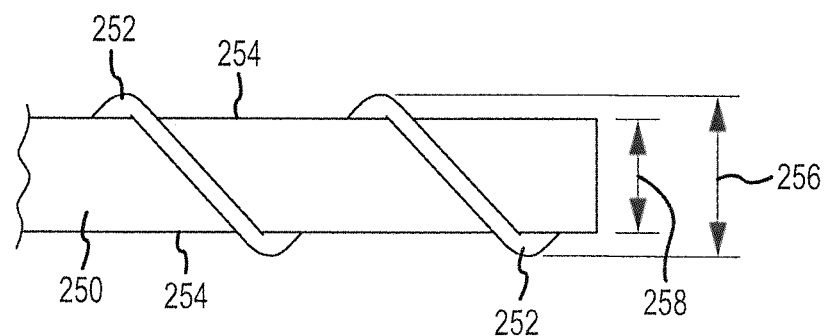
FIG. 9 is a partial side view of an embodiment of an implant device.

Referring now to FIG. 8, an alternative embodiment is shown of a conduit 240 of an implant device having anchor protrusions 242 in the form of knobs, or buttons, and areas of recess 244 adjacent the anchor protrusions 242. The conduit 240 has a first exterior width 246 defined by the anchor protrusions 242 and a smaller, second exterior width 248 defined by the areas of recess 244. An example of another configuration for anchor protrusions is shown in FIG. 9. As shown in FIG. 9, a conduit 250 of an implant device has anchor protrusions 252 and areas of recess 254 on the exterior surface of the conduit 250. The anchor protrusions 252 are in the form of a continuous spiral ridge extending along a portion of the longitudinal length of the conduit 250. The conduit 250 has a first exterior width 256 defined by the anchor protrusions 254 and a smaller, second exterior width 258 defined by the areas of recess 254. As with the embodiments shown in FIGS. 4-7, the conduit embodiment shown in FIGS. 8 and 9 include a height of the anchor protrusions that is equal to one half the difference between the larger and smaller outer diameters of the respective conduits. As will be appreciated from the embodiments of FIGS. 8 and 9, the first exterior width is determined as the width of an envelope volume that contains the anchor protrusions.

Figure 10:
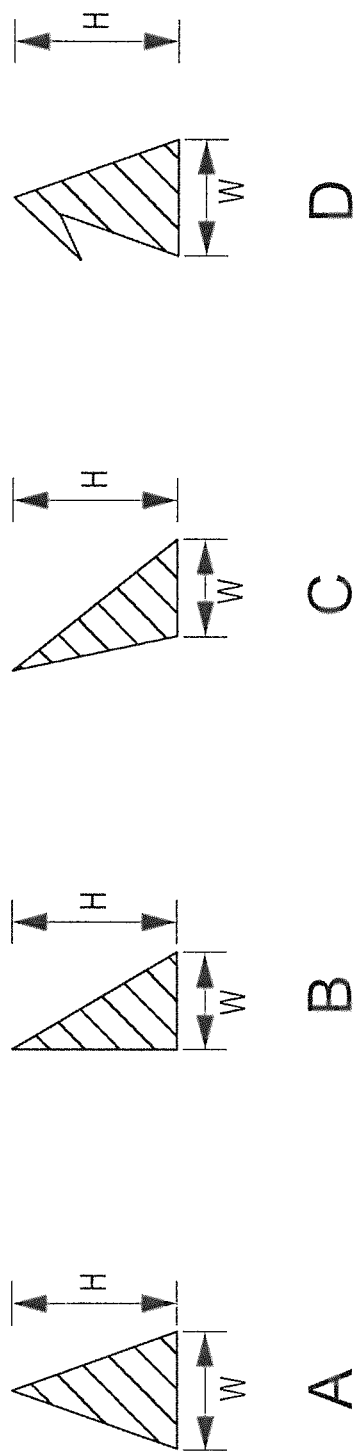
FIG. 10 is an illustration of cross-sections of various configurations for anchor protrusions for an implant device.

FIG. 10 shows examples of some shapes for anchor protrusions that include a tapering width in a direction from the base of the anchor protrusion toward a top of the anchor protrusion. FIG. 10 shows cross-sections of anchor protrusion configurations (designated A-D), each having a greater width at the base than at the top. The height (H) and base width (W) of the anchor protrusions are indicated in FIG. 10. The cross-sections shown in FIG. 10 may, for example, be across a ridge (e.g., circumferential ridge, spiral ridge), a knob protrusion or other anchor protrusion form. All of the anchor protrusion configurations A-D in FIG. 10 are shown with a leading side of the anchor protrusion on the right side and a trailing side on left side of the anchor protrusion. By leading side it is meant a side that enters the fistula first when a conduit containing the anchor protrusion is inserted into the fistula for implantation. By trailing side it is meant the side opposite the leading side and that enters the fistula after the leading side. As will be appreciated, forces applied to the anchor protrusions by tissue contacting the anchor protrusions during insertion into a fistula will impart stresses to the anchor protrusions and, to an extent as permitted by the material of construction of the anchor protrusion, such stresses will tend to deform the anchor protrusion in a direction toward the trailing side. Such deformation aids insertion, and is generally preferred to some degree. The different shapes of the configurations A-D affect the relative ease of insertion of a conduit into and removal of the conduit from a fistula. Configuration A is designed to be equally easy to insert and removable from a fistula while each of configurations B-D are designed to be more easy to insert into a fistula and more difficult to remove from the fistula. Configurations B and C are angled in a way to promote more easy insertion and more difficult removal from a fistula. Configuration D includes a hooked end to engage tissue on the trailing side to make removal from a fistula more difficult than insertion.

FIG. 11 shows some different example configurations (designated E-H) for a head for an implant device. For each head configuration, the length dimension (L) and width dimension (W) of the head configurations are shown. The heads of configurations E-H are shown on end showing the face surface (surface facing away from the fistula when implanted) and the opening of the internal passage at the proximal end of the implant device. For each of the head configurations E-H, the length and width of the face surface and the opposing flanged tissue engagement surface are the same. As shown in FIG. 11, head configuration E has a circular outer edge, and thus has equal length and width dimensions. Head configuration F has an elongated length dimension relative to width dimension, similar to that shown in the implant device embodiment described with reference to FIGS. 4-7. Head configuration G has an elongated length dimension relative to the width dimension, similar to configuration F, but for configuration G the internal passage opening at the proximal end of the implant device has an elliptical cross-section, rather than a circular cross-section as is the case for configurations E and F. Head configuration H has a crescent-shaped head with a significantly larger length dimension than width dimension. The internal passage for configuration H is also shown with an elliptical cross-section. Configurations F-H, with a larger length than width, are advantageously configured for use with fistulas opening into the orbit between the plica semilunaris and the lacrimal caruncle, with the length dimension of the head extending generally in a direction from the bottom of the orbit toward the top of the orbit next to the eyeball, and for configuration H with the concave side of the crescent disposed toward the eyeball and the convex side of the crescent disposed towards the lacrimal caruncle.

Figure 12:
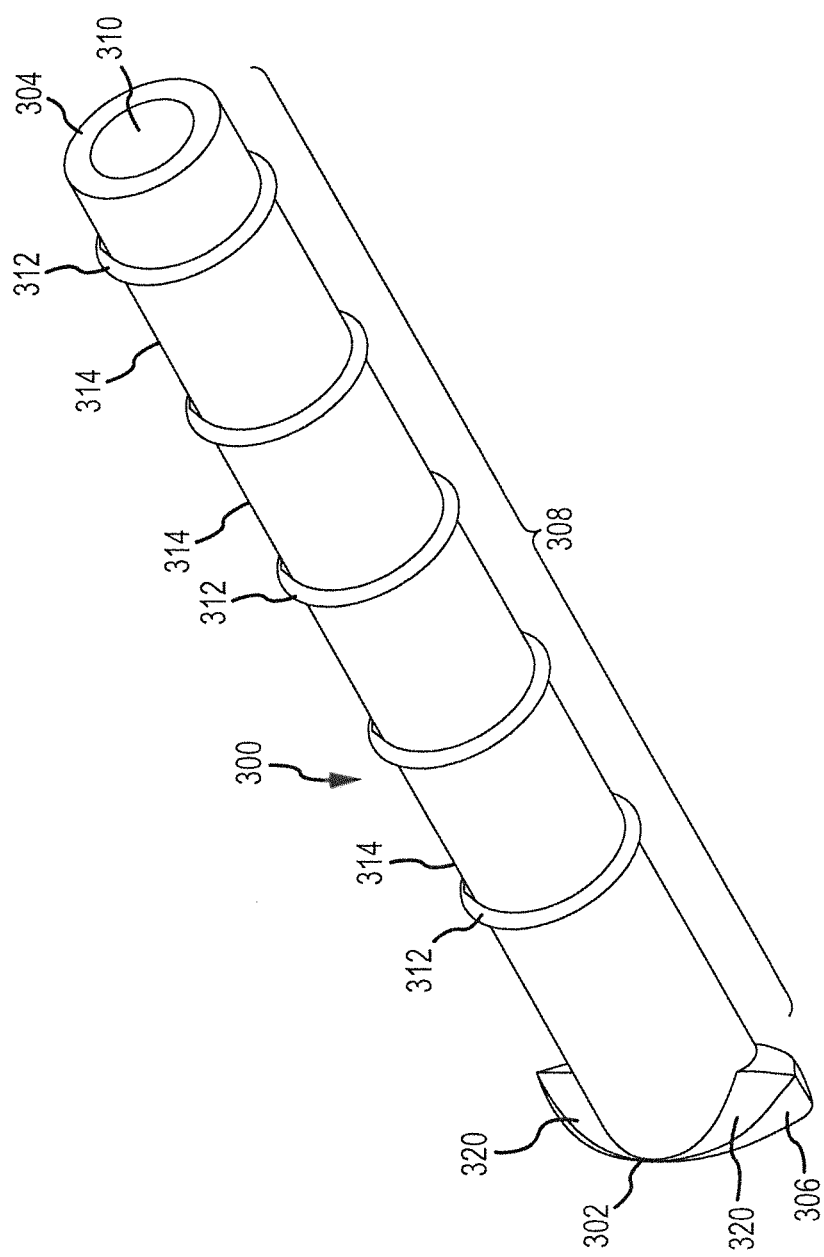
FIG. 12 is a perspective view of an embodiment of an implant device.
Figure 13:
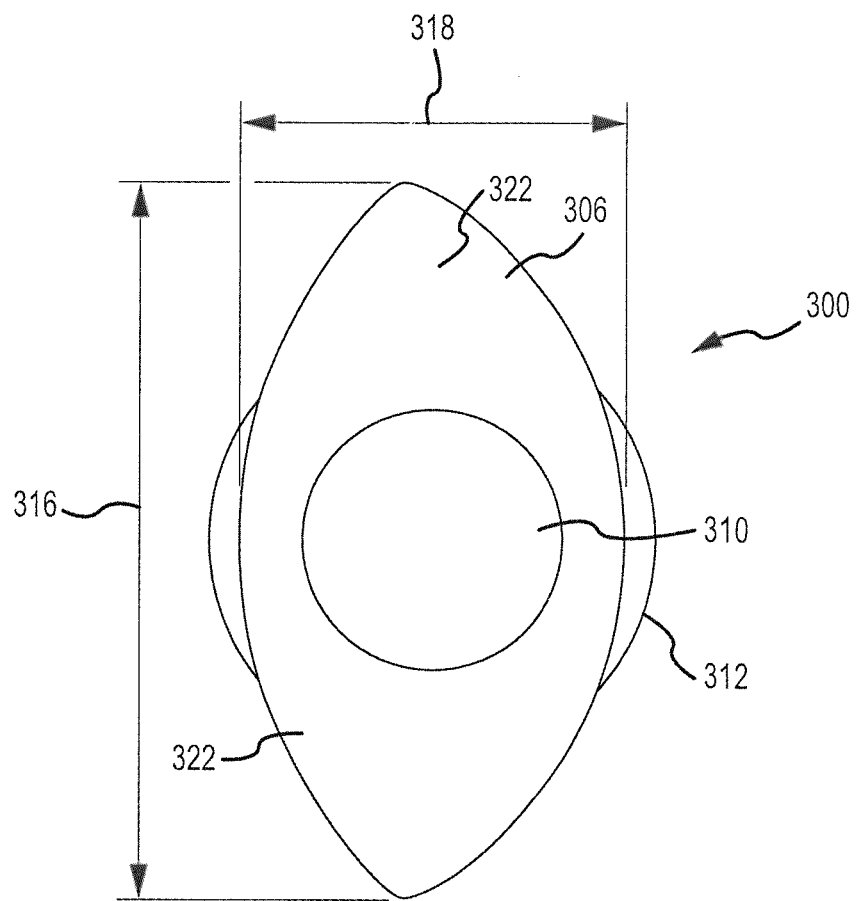
FIG. 13 is an end view of the same embodiment of an implant device shown in FIG. 12.

FIGS. 12 and 13 show another embodiment for an implant device. As shown in FIGS. 12 and 13, an implant device 300 has a proximal end 302 and a distal end 304, with a head 306 located at the distal end 304 and a conduit 308 extending from the head 306 to the distal end 304. The conduit 308 includes an internal passage 310 with a cylindrical shape and opening at the proximal end 302 and the distal end 304. The conduit 310 has an exterior surface including anchor protrusions 312, in the form of circumferential ridges with tapering width, and areas of recess 314 adjacent the anchor protrusions 312. The head 306 has an elongated shape with a significantly larger length dimension 316 than width dimension 318. As seen in FIG. 12, a flanged tissue engagement surface 320 has a beveled configuration (beveled halves extending from central line) to help seat against tissue in a manner to prevent rotation of the implant device 300 when implanted. The face surface 322 is a flat surface to provide a low profile to the head 306 when the implant device 300 is implanted. The configuration of the head 306 is well suited for placement between the plica semilunaris and lacrimal caruncle for use with a subconjunctival fistula route from the orbit where the opening of the fistula into the orbit is located between the plica semilunaris and the lacrimal caruncle. The length dimensions 316 and width dimension 318 represents the length and width of each of the face surface 322 and the flanged tissue engagement surface 320.

Figure 14:
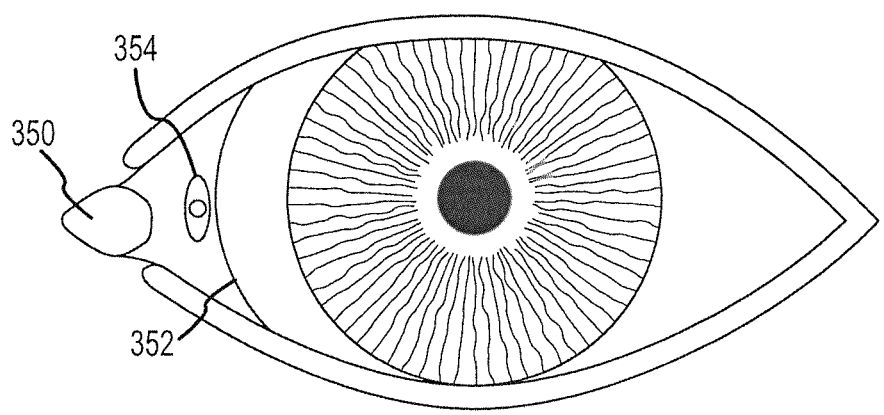
FIG. 14 is an illustration showing an embodiment for placement of an implant device between the lacrimal caruncle and plica semilunaris.

FIG. 14 shows an example of an implant device with a conduit passing through a fistula formed subconjunctivally between the lacrimal caruncle 350 and the plica semilunaris 352, and showing an example location for the head 354 of the implant device. The head 354 is shown with an elongated configuration, such as for example the head configuration shown in FIGS. 4-7, one of the head configurations F-H shown in FIG. 11 or the head configuration shown in FIGS. 12 and 13.

Figure 15:
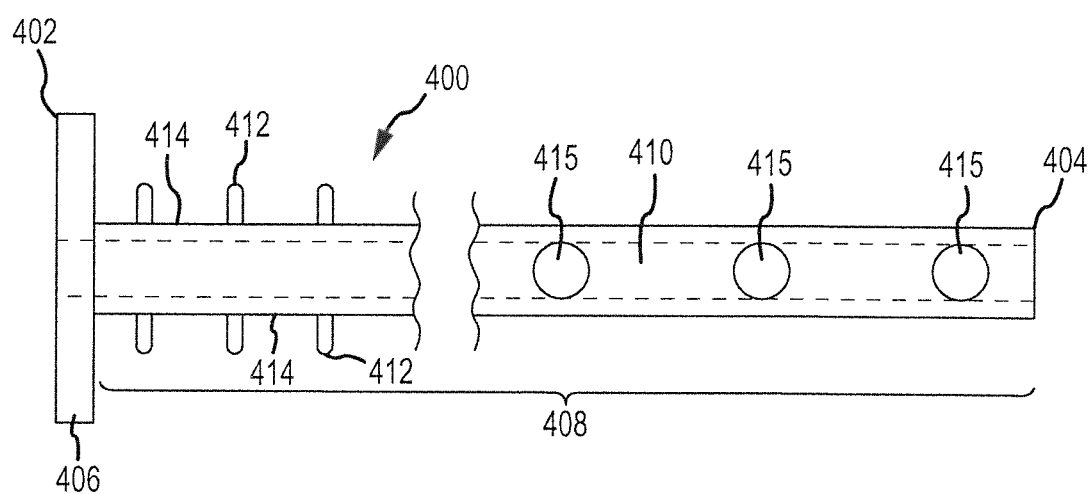
FIG. 15 is a side view of an embodiment of an implant device.

FIG. 15 shows another embodiment of an implant device. As shown in FIG. 15, an implant device 400 has a proximal end 402 and a distal end 404. The implant device 400 includes a head 406 at the proximal end 402 and a conduit 408 extending from the head 406 to the distal end 404. The conduit 408 has an exterior surface with anchor protrusions 412 and areas of recess 414 adjacent the anchor protrusions 412. An internal passage 410 (shown by dashed lines) extends from the proximal end 402 to the distal end 404. A distal longitudinal portion of the conduit 408 includes apertures 415 through the wall of the conduit 408 and providing fluid communication from the internal passage 410 to outside of the conduit 408. The apertures 415 provide a route for drug formulations, irrigation solutions or other treatment compositions to exit from the internal passage into different locations within a paranasal sinus when the implant device 400 is implanted. When the implant device 400 is implanted, at least one or more of the anchor protrusions 412 will be located within the fistula to engage tissue for anchoring and at least some, and preferably all, of the apertures 415 will be disposed beyond the distal end of the fistula inside of a paranasal cavity. The configuration shown in FIG. 15 is particularly advantageous for situations when the conduit 408 extends through multiple cavities of a paranasal sinus or when the conduit 408 extends from one paranasal sinus into another paranasal sinus. The embodiment shown in FIG. 15 does not include the anchor protrusions 412 on the longitudinal portion of the conduit 408 where the apertures 415 are disposed. As an alternative configuration, the longitudinal portion of the conduit 408 including the apertures 415 could include anchor protrusions, of the same configuration as those of the anchor protrusions 412 or of different configurations.

Figure 16:
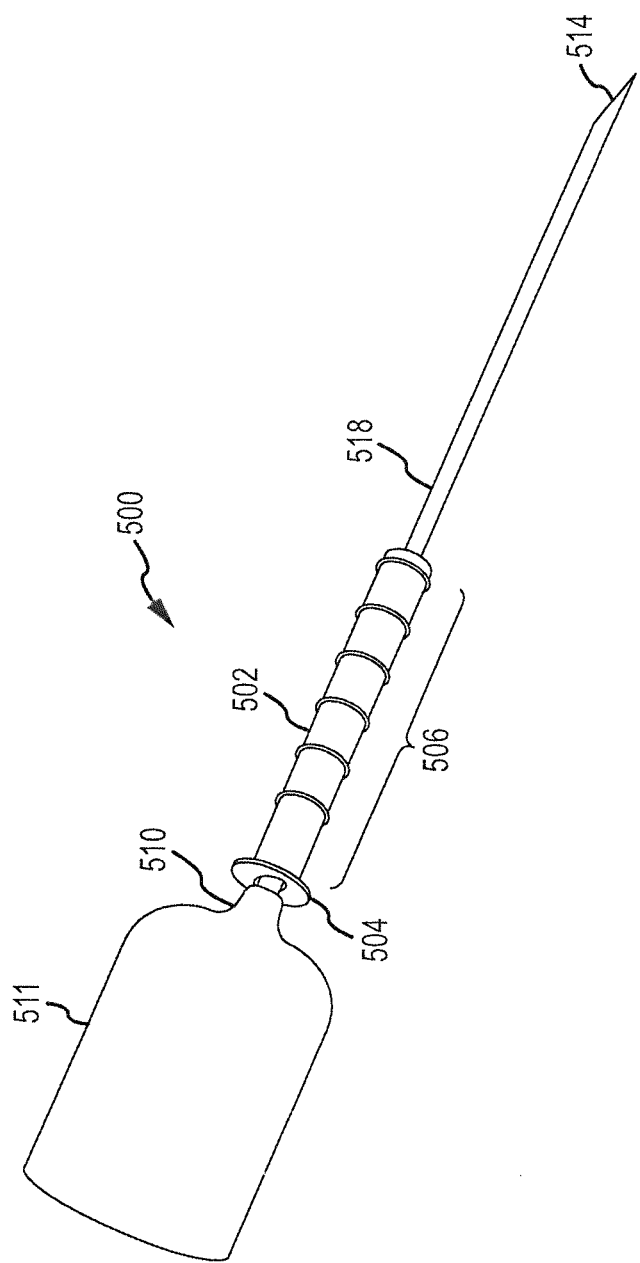
FIG. 16 is a perspective view of an embodiment of a surgical tool.

FIG. 16 shows one embodiment of a surgical tool. As shown in FIG. 16, a surgical tool 500 includes an implant device 502 having a head 504 and a conduit 506, for example as previously described with respect to any of the FIGS. 4-15. The implant device 502 is mounted on a carrier 510. The carrier 510 comprises a handle 511 adjacent a proximal end of the surgical tool 500. The carrier 510 includes a working member 518 connected to the handle 511. The working member 518 extends from the handle 511 through the internal passage of the implant device 502 and to a distal end of the surgical tool 500. At the distal end of the working member 518 is a distal tip 514. The handle 511 may be made of any convenient material of construction, for example plastic or metallic compositions. The working member 518 may be made for example of a medical-grade metallic composition, such as a medical-grade stainless steel. In general when a member is referred to herein as a "working member", the term indicates that the member is such that at least a portion of the member is designed for being disposed within or through a fistula when a tool containing the member is used, for example during formation of a fistula or during performance of some procedure in or through a fistula. Some examples of working members include various hollow members (e.g., hypodermic needles, cannulas) and various solid members (e.g., trocars, stylets, dilating members, implant delivery members). Such a working member may be disposed in or through the fistula in a manner that the member contacts tissue in the fistula or in a manner not to contact tissue in a fistula (e.g., inside of a passage of an implant device passing through the fistula).

With continued to reference to FIG. 16, the implant device 502 is mounted on the carrier 510 with the working member 518 disposed through the internal passage of the implant device 502. The width of the working member 518 disposed through the internal passage of the implant device 502 may advantageously be sized to be just smaller than the internal passage of the implant device for a close fit between them, provided that the fit is not so tight that the implant device 502 is difficult to slide down the working member 518 toward the distal tip 514.

Continuing to refer to FIG. 16, the surgical tool 500 may be used to form a fistula between the lacrimal system and a paranasal sinus and to facilitate implantation of the implant device 502 in the fistula. A surgeon may manipulate the surgical tool 500 by hand-grasping the handle 511. The surgeon may advance the distal tip 514 to a location within the lacrimal apparatus where the fistula is to be formed to a target paranasal sinus. The surgeon may then force the distal tip through tissue separating the lacrimal apparatus and the target paranasal sinus to form the fistula. With a leading portion of the working member 518 disposed through the fistula, a surgeon may slide the implant device 502 along the working member 518 toward the distal tip 514 until the implant device 502 is positioned for implantation with the conduit 506 disposed through the fistula and a flanged tissue engagement surface of the head 506 disposed against tissue adjacent the proximal end of the fistula in the lacrimal apparatus, or the carrier may continue to be advanced to push the conduit 506 into the fistula. After the implant device 502 is positioned for implantation, the surgeon may then manipulate the handle 504 to retract the working member 518 to withdraw the working member from the internal passage of the implant device 502 and to fully disengage the carrier 510 from the implant device 502, leaving the implant device 502 implanted with the conduit 506 extending through the fistula and into the paranasal sinus.

With continued reference to FIG. 16, the working member 518 may be a solid member (e.g., trocar, stylet) or may be a hollow member (e.g., a hollow needle, cutting cannula). If the working member 518 is a hollow member with an opening at the distal tip 514, then tissue will tend to be cored and collected in the hollow interior of the working member 518 when the surgical tool 500 is used to form a fistula. If the working member 518 is a solid member, then tissue coring should not occur. In many instances, it may be preferred to have the working member 518 be a solid member that does not core tissue, because the implant device may tend to be held more securely within a fistula formed without tissue coring. The surgical tool 500 shown in FIG. 16 is particularly well adapted for forming a fistula from the orbit subconjunctivally to a paranasal sinus, and particularly when the fistula is formed at a location in the orbit between the plica semilunaris and the lacrimal caruncle.

Figure 17:
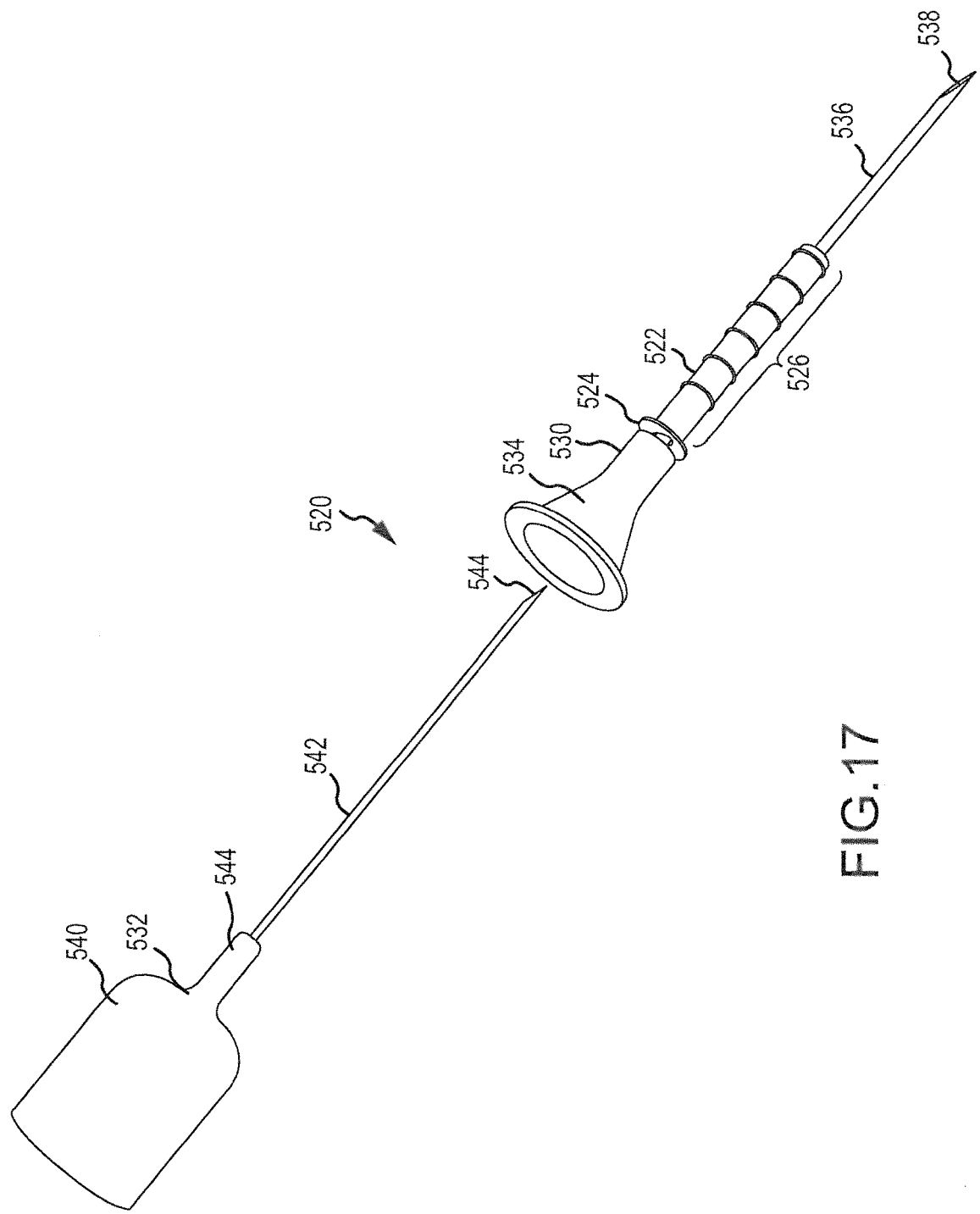
FIG. 17 is a perspective view of an embodiment of a surgical tool showing some components in exploded view.
Figure 18:
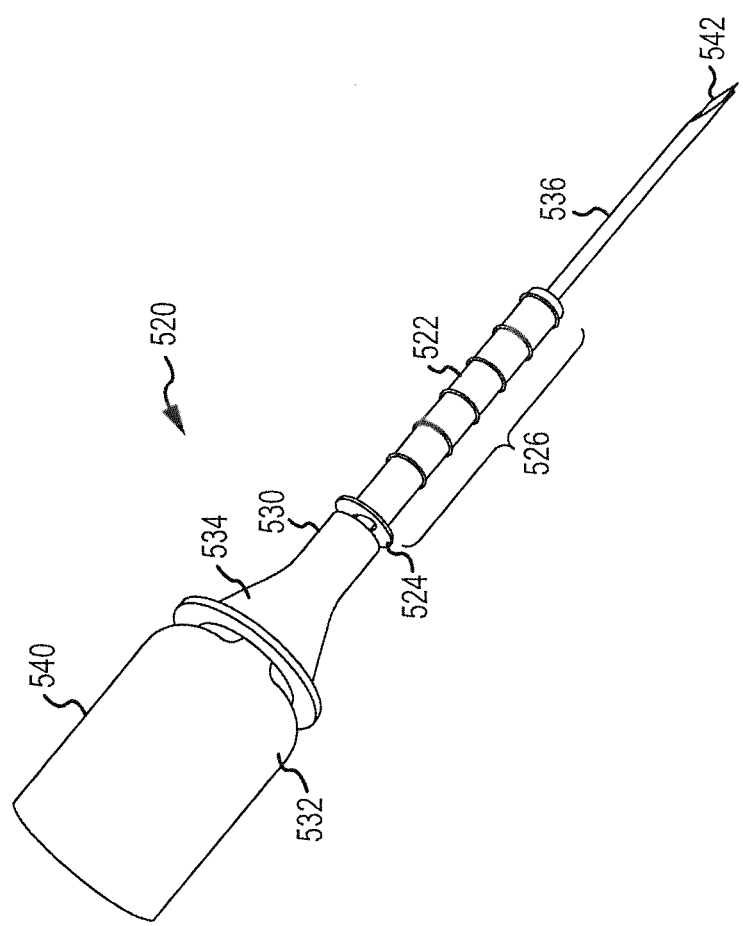
FIG. 18 is a perspective view of the same embodiment of a surgical tool shown in FIG. 17, showing the surgical tool fully assembled.

FIGS. 17 and 18 show another surgical tool, which may also be referred to as an implantation tool assembly. FIG. 17 shows an expanded view of some features of a surgical tool 520 and FIG. 18 shows the same surgical tool 520 as the surgical tool 520 appears fully assembled. As shown in FIG. 17, the surgical tool 520 includes an implant device 522 with a head 524 and a conduit 526, for example as described previously with respect to any of FIGS. 3-16. The surgical tool 520 includes a carrier with two pieces, a first carrier piece 530 and a second carrier piece 532. The first carrier piece 530 has a syringe hub 534 (e.g., for making a luer connection) and a hollow working member 536 (e.g., hollow needle, cannula) connected with the hub 534. The hollow working member 536 has a distal tip 538. The second carrier piece 532 has a handle 540 and a solid working member 542 (e.g., stylet, trocar) connected with the handle 540. The solid working member 542 has a distal tip 544. As assembled, the surgical tool 520 includes the solid working member 542 inserted through the interior of the hub 534 and through the hollow interior of the hollow working member 536. As assembled, the handle 540 of the second carrier piece 532 is disposed distal of the hub 534 with an engagement member 544 inserted into the interior of the hub 534. As will be appreciated, features of the hub 534 and/or the engagement member 544 and/or the handle 540 may contain keying and engagement features to align and/or permit detachable engagement of the first carrier piece and the second carrier piece when assembled. FIG. 18 shows the same surgical tool 520 as it appears fully assembled. As shown in FIG. 18, the first carrier piece 522 and the second carrier piece 532 are engaged with the solid working member 542 disposed through the hollow interior of the hollow working member 536.

With continued reference to FIGS. 17 and 18, the surgical tool 520 may be used to form a fistula between the lacrimal apparatus and a paranasal sinus. The distal tips 538 and 544 of the first and second carrier pieces 530 and 532 form a distal tip that will not significantly core tissue. A surgeon may grasp the handle 540 and advance the distal tip to a location in the lacrimal apparatus where the fistula is to be formed (e.g., in the orbit, in the nasolacrimal duct) and the distal tip may then be forced through tissue into a paranasal sinus to form the fistula to the target paranasal sinus. With a leading portion of the hollow working member 536 disposed through the fistula, the implant device 522 may be slid down the hollow working member 536 and into position for implantation with the conduit 526 disposed through the fistula and the head 524 disposed adjacent the proximal end of the fistula, or the hollow working member 536 may be further advanced to push the conduit 526 into the fistula. The hollow working member 536 may then be retracted and disengaged from the implant device 522 to leave the implant device 522 in the implanted position.

Figure 19:
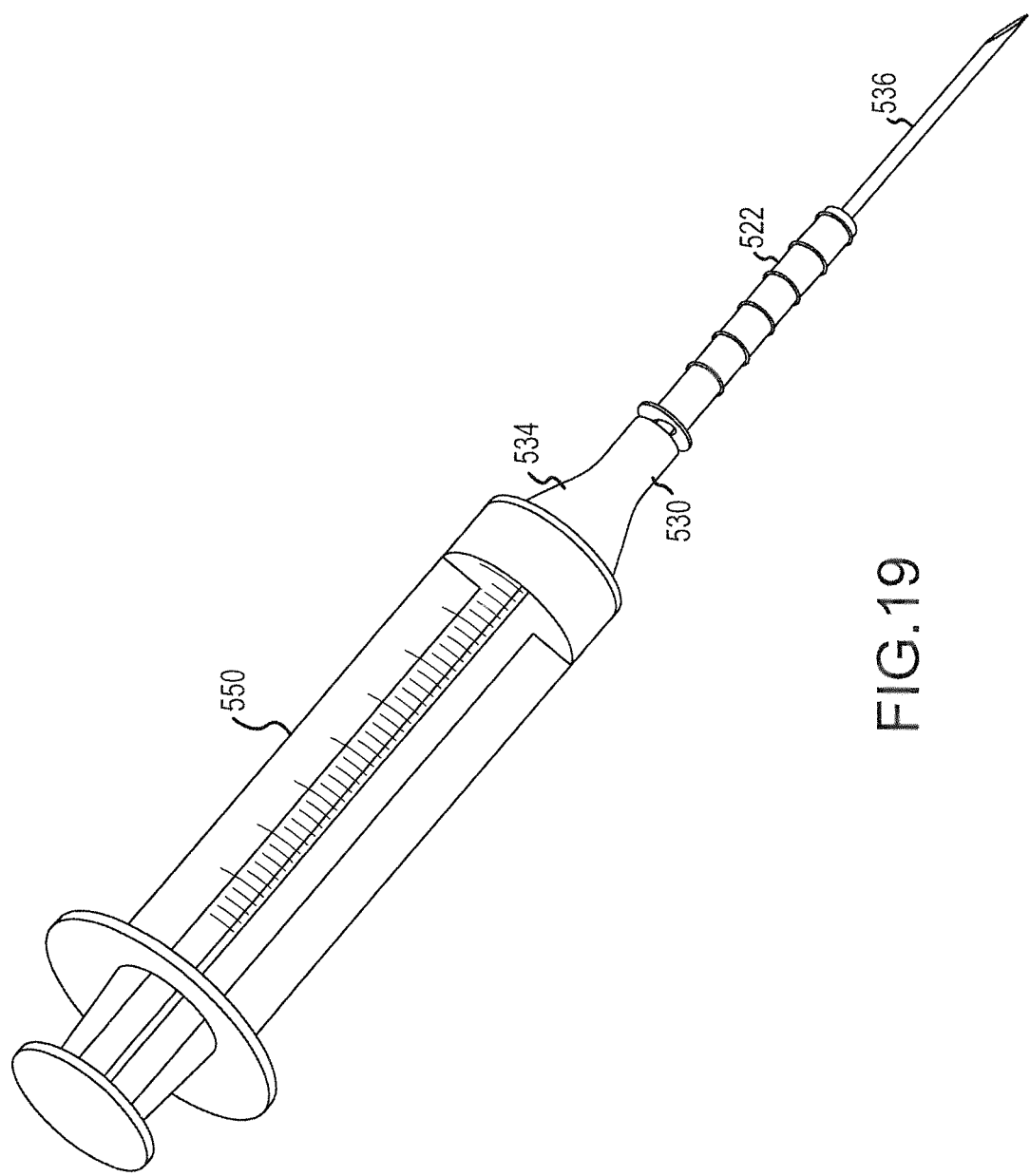
FIG. 19 is a perspective view showing a first carrier piece of the same embodiment of a tool shown in FIGS. 17 and 18, with the first carrier piece connected with a syringe.

Continuing with reference to FIGS. 17 and 18, the hollow working member 536 facilitates performance of an ancillary medical procedure involving aspirating fluid from or introducing fluid into the paranasal sinus. For example, before or after positioning the implant device 522 in the proper location for implantation, the second carrier piece 532 may be disengaged from the first carrier piece 534 to remove the solid working member 542 from the hollow interior of the hollow working member 536. The hollow working member 536 is then available for aspiration of fluid from or injection of fluid into the paranasal sinus. The hub 534 may be engaged with a corresponding connection structure of a syringe and the syringe may be operated to aspirate fluid from the paranasal sinus into the syringe or to inject fluid from the syringe into the paranasal sinus. Fluids that may be injected into the paranasal sinus include irrigation fluid or treatment compositions containing a drug, for example to inject a drug bolus for treatment of sinusitis. As used herein, "fluid" includes flowable compositions, including compositions that may have a solid material dispersed or suspended in a fluid medium. After the implant device has been properly positioned for implantation and after performing any desired ancillary medical procedure, the first carrier pierce may be retracted to disengage the hollow working member 536 from the internal passage of the implant device 522 and to leave the implant device 522 as an implant. FIG. 19 shows the first carrier piece 536 of the surgical tool 500 connected with a syringe 550.

Referring now to FIGS. 20-25, some additional examples of surgical procedures involving forming a fistula and implanting an implant device, and some example surgical tools for use therewith, will now be described.

Figure 20:
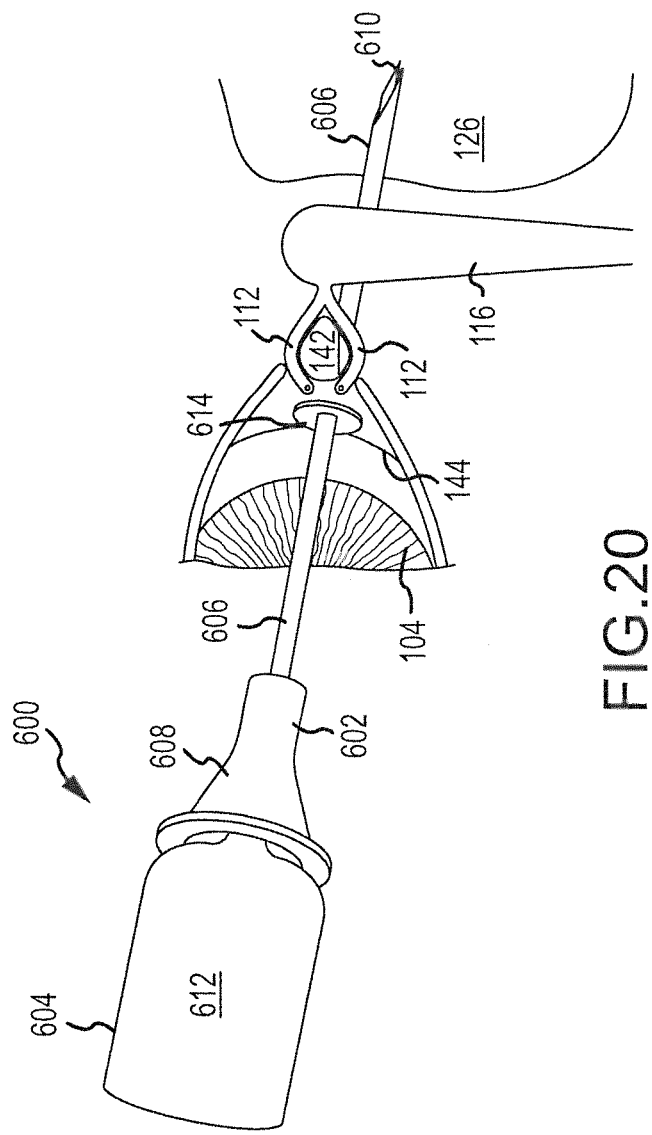
FIG. 20 is an illustration showing use of a surgical tool to form a fistula between the orbit and an ethmoid sinus during a surgical procedure.

In FIG. 20 a surgical tool, which may also be referred to as an implantation tool assembly, in the form of an entry tool 600 is shown in the process of making a fistula through tissue between the lacrimal caruncle 142 and the plica semilunaris 144. Numbering of anatomical parts is the same as in FIGS. 1 and 3. The fistula is formed through tissue between the conjunctival sac in the orbit and the ethmoid sinus 126. The route for the fistula would be consistent with general fistula route 132 as shown in FIG. 3. The entry tool 600 includes a first piece 602 and a second piece 604. The first piece 602 includes a hollow working member 606 and a hub 608. The second piece 604 includes a solid working member (not shown) disposed through a hollow interior of the hollow working member 606. A distal tip portion of the hollow working member 606 of the first piece 602 and a distal tip portion of the solid working member of the second piece 604 form a distal tip 610 with a shape suitable for insertion through the tissue to form a fistula from the conjunctival sac to the ethmoid sinus 126. The second piece 604 includes a hand-manipulable handle 612. The hub 608 may be configured for connecting with a syringe or other fluid manipulation device, such as through a luer connection. The handle 612 may be retracted relative to the hub 608 to remove the solid working member from the interior of the hollow working member 606 and to disengage the second piece 604 from the first piece 602. As shown in FIG. 20, the distal tip 610 has been advanced from a location in the conjunctival sac between the caruncle 142 and the plica semilunaris 144 to form a fistula between the conjunctival sac and the ethmoid sinus 126. As shown, the fistula passes behind the caruncle 142, canaliculi 112 and nasolacrimal duct 116 to access the ethmoid sinus 126. The first piece 602 of the entry tool 600 includes a collar stop 614 to prevent the hollow working member 606 from being advanced through tissue beyond a certain distance. The first piece 602 and the second piece 604 may, for example, be substantially the same as the first carrier piece 530 and the second piece 532 of the tool assembly 520 of FIG. 17, but with the added collar stop 614 and not including an implant device mounted thereon.

Figure 21:
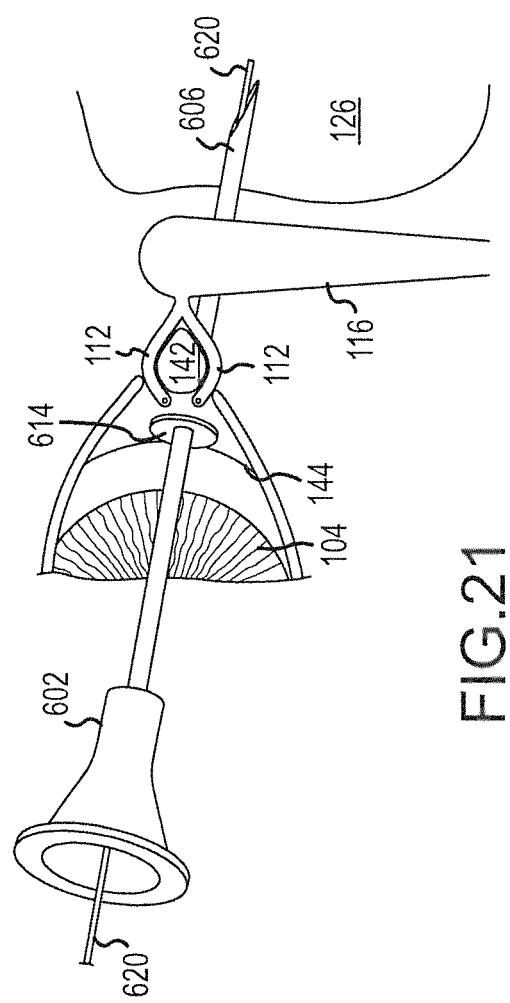
FIG. 21 is an illustration showing insertion of a guide wire following formation of the fistula during a surgical procedure.
Figure 22:
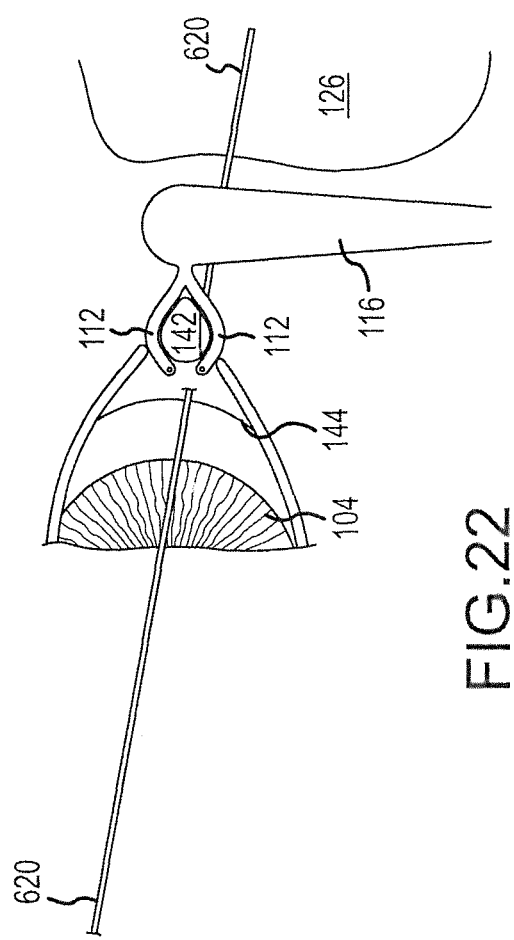
FIG. 22 is an illustration showing a guide wire in place as a guide to a fistula during a surgical procedure.

After the entry tool 600 has been used to initially form a fistula to the ethmoid sinus 126, then the second piece 604 may be disengaged from the first piece 602 and a guide wire inserted through the internal passage through the hollow working member 606. FIG. 21 shows the first piece 602 after disengagement of the second piece 604 and after insertion of a guide wire 620 through the first piece 602 and exiting from a distal end of the first piece 602 in the ethmoid sinus 126. After insertion of the guide wire 620, the first piece 602 may be retracted and removed from the fistula, leaving the guide wire 620 in place as a guide to and through the fistula. FIG. 22 shows the guide wire 620 disposed through the fistula after removal of the first piece 602. The guide wire 620 is now available for guiding additional tools to and through the fistula into the ethmoid sinus 126.

Figure 23:
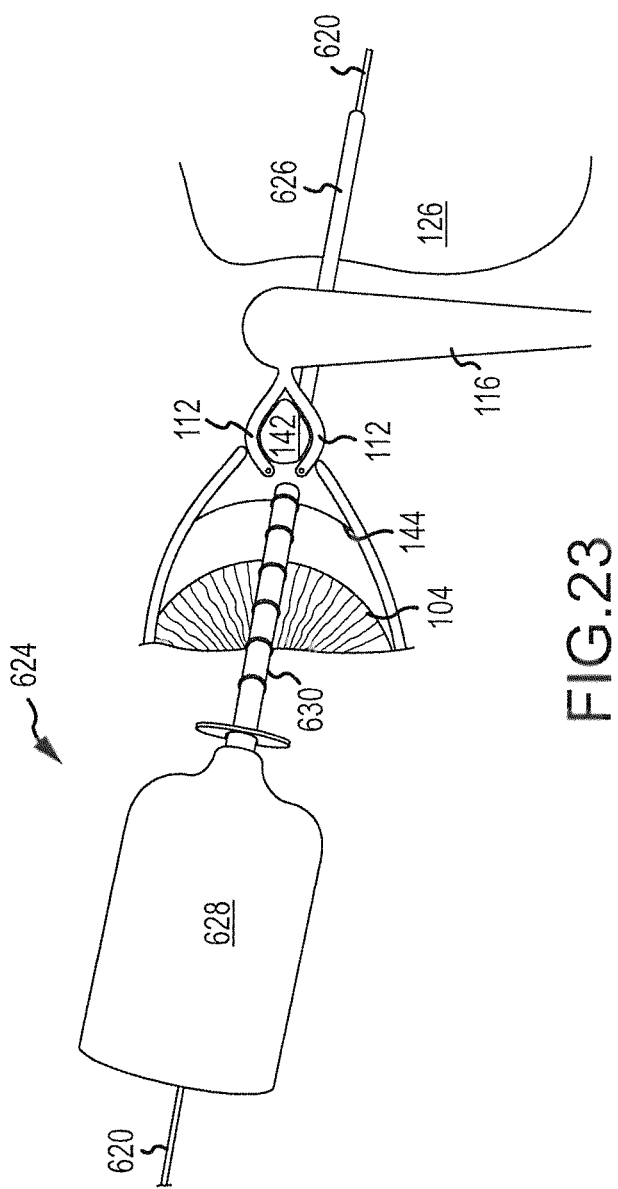
FIG. 23 is an illustration showing use of a surgical tool for implantation of an implant device during a surgical procedure.
Figure 24:
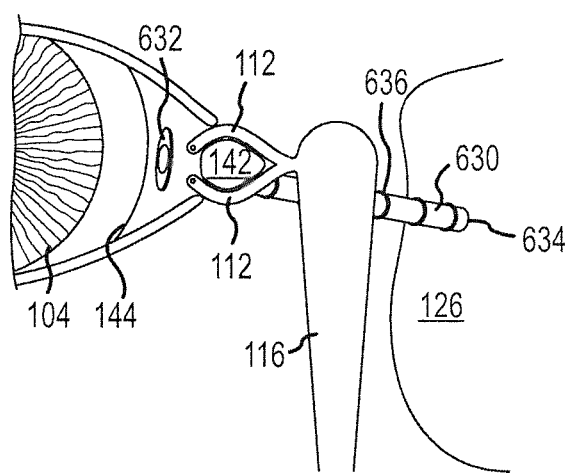
FIG. 24 is an illustration showing placement of an implant device following implantation during a surgical procedure.

With reference now to FIG. 23, the guide wire 620 has been used to guide a surgical tool, in the form of an implant tool 624. The implant tool 624 includes a hollow working member 626 and a hand-manipulable handle 628. The implant tool 624 includes an internal passage passing through the handle 628 and the hollow working member 626. As shown in FIG. 23, the guide wire 620 has been threaded through the internal passage of the implant tool 624 to guide the hollow working member 626 to and through the fistula and into the ethmoid sinus 126. The implant tool 624 also includes an implant device 630 mounted on the hollow working member 626. FIG. 23 shows the implant tool 624 advanced to a point where the distal end of the implant device 630 is in the vicinity of the proximal end of the fistula opening into the conjunctival sac. From this position, the implant device 630 may be advanced into the fistula with a head of the implant device 630 disposed adjacent the conjunctiva in the conjunctival sac and a distal end of the implant device 630 extending into the ethmoid sinus 626. The implant tool 624 may, for example, be a tool of the design such as that shown for the surgical tool 500 in FIG. 16, with a hollow needle for the working member 518. The implant device 630 of the implant tool 624 may, for example, have features as described with respect to any of FIGS. 4-19. With the continued reference to FIG. 23, the hollow working member 626 of the tool 624 preferably includes a blunt tip. The handle 628 and the hollow working member 626 form a carrier for the implant device 630. The handle 628 may be retracted and the hollow working member 626 disengaged from the implant device 630 after the implant device has been appropriately positioned for implantation through the fistula. As an alternative to the configuration of the implant tool 624 as shown in FIG. 23, the implant tool 624 could be configured to include a hub for connection (e.g., through a luer connection) with a syringe of other fluid manipulation device. For example, the implant tool 624 could be configured with a hub in a manner similar to the configuration of the first piece 602 shown in FIG. 21 and with the implant device appropriately mounted for implantation. As another variation on the configuration of the implant tool 624, the working member 626 could be fitted with a collar stop (e.g., as shown in FIG. 21) or other mounting aid against which the implant device 630 could be disposed to provide some additional distance between a proximal end of the implant device 630 and the handle 628. FIG. 24 shows the implant device 630 as implanted and following disengagement of the hollow working member 626 of the implant tool 628. As implanted, a head 632 at the proximal end of the implant device 630 is located adjacent the conjunctiva in the conjunctival sac within the orbit between the caruncle 142 and the plica semilunaris 144 and the distal end 634 of the implant device 630 is located in the paranasal sinus 626. Some of anchor protrusions 636 are disposed within the fistula to engage tissue and help anchor the implant device 630.

Figure 25:
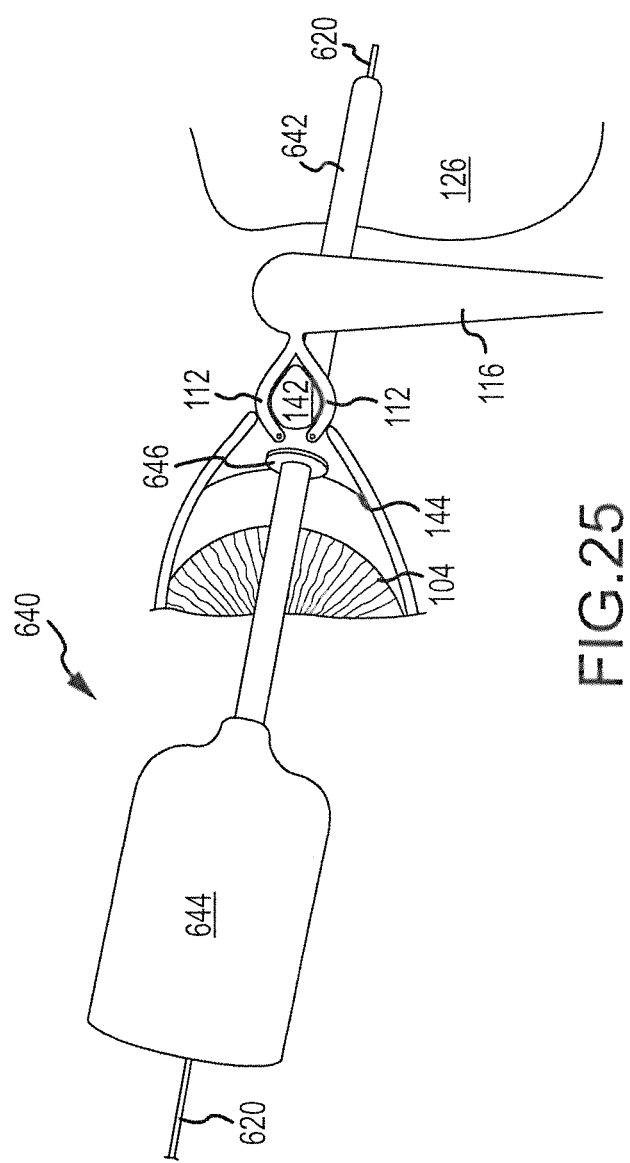
FIG. 25 is an illustration showing use of a surgical tool to dilate a fistula following initial formation of the fistula during a surgical procedure.

The procedure as described with reference to FIGS. 20-24 permits the working member 606 of the entry tool 600 to have a larger diameter working member 626 to form a fistula of appropriate size for accommodating the implant device 630 which is then implanted in a separate step using the implant tool 624 with the implant device 630 carried on to the working member 626, which may advantageously have a smaller diameter then the working member 606 used to form the fistula. As an alternative, an intermediate step to dilate the fistula to a desired size for implantation may be performed between initially forming the fistula with the entry tool 600 and implanting the implant device 630 using the implant tool 624. FIG. 25 shows a surgical tool in the form of a dilator tool 640 having a hollow working member 642 and a hand-manipulable handle 644. The working member 642 is disposed through the fistula, guided by the guide wire 620 passing through an internal passage through the dilator tool 640. As shown in FIG. 25, the working member 642 has been advanced to the point where a stop collar 646 attached to the working member 642 has engaged conjunctival tissue in the conjunctival sac adjacent a proximal end of the fistula. For this alternative implementation, the hollow working member 642 of the dilator tool 640 would have a larger diameter than the hollow working member 606 of the entry tool 600 shown in FIGS. 20 and 21. The hollow working member 642 of the dilator tool 640, therefore widens the fistula further to a desired size to accommodate easier insertion of the implant device 630. Although the intermediate step of dilation as shown is not required, it permits the use of a smaller-diameter working member 606 during initial formation of the fistula. The use of a smaller diameter for the working member 606 to initially form the fistula permits better visibility and procedural control for a surgeon performing the procedure. The working member 642 may preferably include a blunt tip.

In a method for providing access to a paranasal sinus to a human to permit performance of medical treatments or procedures in the paranasal sinus over an extended time, a surgically formed, durably patent fistula may be created between the lacrimal apparatus of the human and the paranasal sinus. By surgically formed, it is mean that the fistula is an artificial passage through tissue that is intentionally formed by a surgical operation. For example, the fistula may be formed using a trocar, stylet, needle or cannula. The fistula may be formed by a surgical tool as described with reference to any of FIGS. 16-19. By "durably patent" it is meant that the fistula is resistant to closure by natural tissue repair mechanisms and remains open (patent) for an extended period of time to provide access into the paranasal sinus over the extended period of time. The extended period of time may be any period of time sufficient for performing through the fistula any desired medical treatments or procedures. The extended period of time may, for example, be at least 7 days, at least 14 days, at least 30 days, at least 180 days, or longer. The extended period may be permanent.

A fistula may be maintained as durably patent for an extended period of time by a variety of techniques. As one example for maintaining fistula patency, an implant device may be disposed through the fistula to prevent the fistula from closing, and the implant device may include an internal passage for providing access through the fistula into the paranasal sinus. When access to the paranasal sinus is no longer required, the implant device may be removed to permit tissue to repair and close the fistula. The implant device may, for example, have a configuration as described with respect to any of FIGS. 4-19 or may have a different configuration. As another example for maintaining fistula patency, the fistula may be formed initially with a relatively large diameter, and preferably with a clean cut. A large, cleanly cut hole will naturally tend to remain patent and not repair for at least a significant time. The relatively large diameter of the fistula may, for example be at least 2 millimeters or larger, as described above. When the fistula is formed with such a large diameter, the fistula will preferably be formed at a location in the nasolacrimal duct. As another example for maintaining fistula patency, after the fistula is formed the tissue adjacent the fistula may be mechanically treated to form a mechanical impediment to tissue repair that would close the fistula. The mechanical treatment could involve, for example over-sewing tissue adjacent the fistula or stapling tissue adjacent the fistula to mechanically retain the tissue in a manner to inhibit tissue repair that would close the fistula. As another example for maintaining fistula patency, tissue adjacent the fistula may be treated with a substance (e.g., a drug) effective to inhibit natural tissue repair and closure of the fistula, such as for example treatment with an antigranulation or anti-scarring agent (e.g., steroids, Mitomycin C).

Some aspects of the invention involve use of a break-away sheath. Such break-away sheath may be used with or without use also of an over-the-wire procedure.

Figure 26:
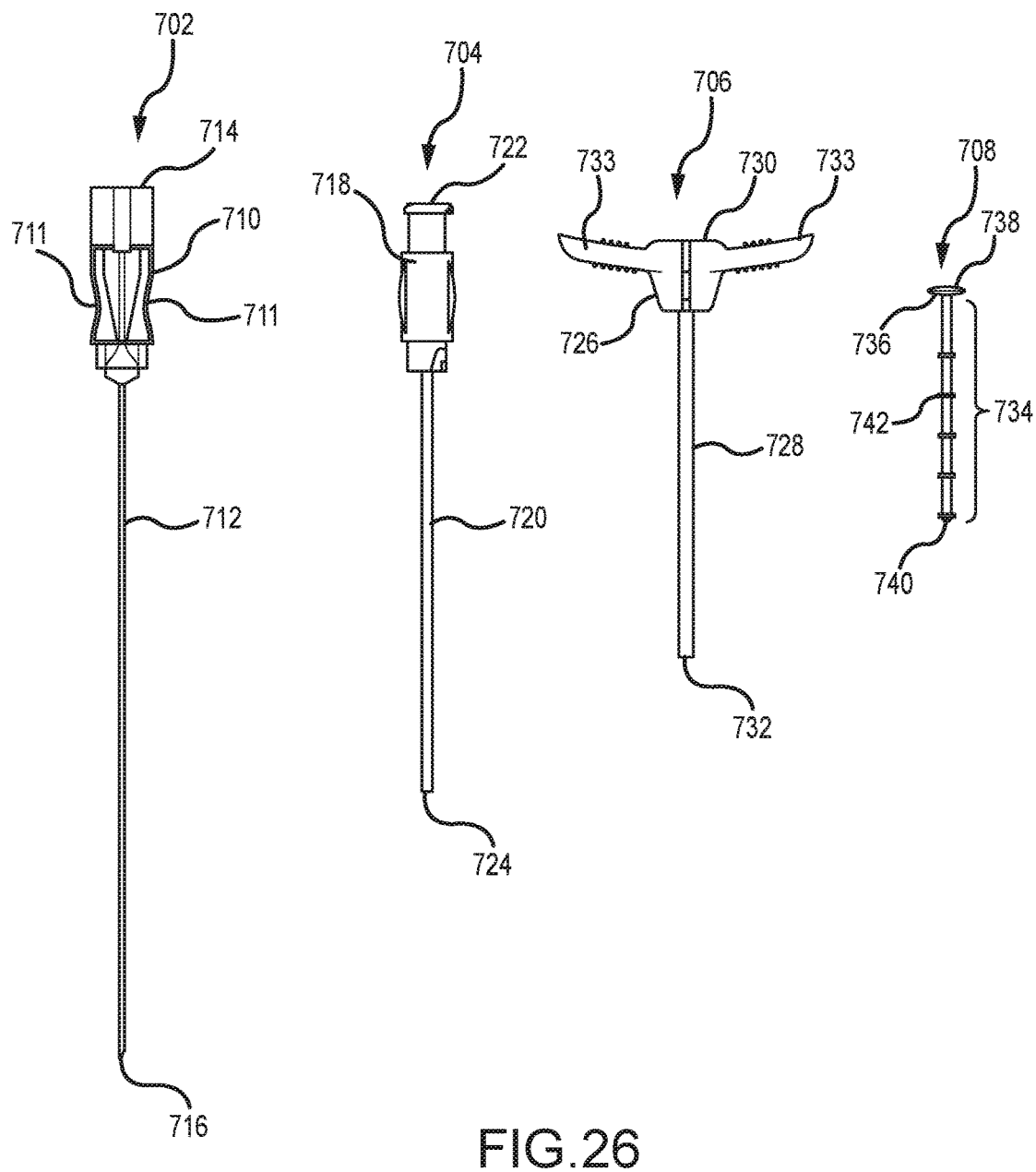
FIG. 26 is an illustration of components of an embodiment of an implantation kit.

Reference is now made to FIG. 26, which shows some components that may be included with an implantation kit according to one embodiment of the invention. Additional components to those shown in FIG. 26 may also be included with the kit. As shown in FIG. 26, the kit includes a piercing tool 602, a dilator tool 604, a sheath tool 606 and an implant device 608. Reference may be made to "proximal" or "distal" in describing relative locations of component features in relation to a medical professional during use. A proximal end of a component or feature may refer to a longitudinal end of the component or feature that may be disposed toward a medical professional during normal use and a distal end may refer to a longitudinal end opposite the proximal end, and which may be disposed away from the medical professional during normal use. Reference to a feature as being located proximal of some other feature may mean that the feature is located toward a medical professional during normal use relative to the other feature. Conversely, a feature referred to as being located distal of some other feature may mean that the feature is located away from the medical professional during normal use relative to the other feature.

As shown in FIG. 26, the piercing tool 702 includes a handle portion 710 and a working member 712. The handle portion 710 is located adjacent a proximal end 714 of the piercing tool 702 and the working member 712 extends from the handle 710 to a distal end 716 of the piercing tool 702. The distal end 716 of the piercing tool 702 also coincides with a distal end of the working member 712. A proximal end of the working member 712 is located adjacent to a distal end of the handle 710. The handle portion includes finger grip indentations 711 to facilitate easy handling and manipulation.

As shown in FIG. 26, the dilator tool 704 includes a head portion 718 and a hollow dilator member 720. The dilator tool 704 includes an internal passage that extends through the length of the dilator tool 704 from a proximal end 722, through the dilator member 720 and to a distal end 724 of the dilator tool 704. The internal passage of the dilator tool 704 is configured (e.g., has sufficient length and appropriate width features) to permit the working member 712 to be inserted into and disposed through the internal passage of the dilator tool 704 with the proximal end of the dilator tool 704 disposed toward the proximal end of the working member 712 and with a distal portion of the working member 712 extending beyond the distal end 724 of the dilator tool 704. In that regard, the working member 712 may have a longitudinal length that is larger than a longitudinal length of the dilator member 720 and larger than a longitudinal length of the dilator tool 704.

As shown in FIG. 26, the sheath tool 706 includes a head portion 726 and a break-away sheath 728. The head portion 726 is located adjacent a proximal end 730 of the sheath tool 706 and the break-away sheath 728 extends from the head portion 726 to a distal end 732 of the sheath tool 706. The sheath tool 706 includes an internal passage from the proximal end 730, through the break-away sheath 728 and to the distal end 732, with the internal passage configured to permit insertion of the hollow dilator member 720 therethrough. The dilator member 720 may be inserted through the internal passage of the sheath tool 706 with the head portion of the sheath tool disposed toward the head portion 718 of the dilator tool 704 and with the dilator member 720 extending through the entire length of the break-away sheath 728 with a distal portion of the dilator member 720 exposed beyond the distal end 732 of the sheath tool 706. The head portion 718 of the dilator tool 704 may be configured to engage with the head portion 726 of the sheath tool 706. Such engagement may include a locking engagement, such as a rotational lock between the head portion 718 and the head portion 726 to retain the dilator tool 704 and the sheath tool 706 in an engaged relationship or to permit disengagement of the dilator tool 704 and the sheath tool 706 as desired. A distal portion of the handle 710 of the piercing tool 702 may likewise be configured to engage with a proximal end of the head portion 718 of the dilator tool 704, and such an engagement configuration may include a locking engagement, such as a rotational lock. In one possible implementation, the dilator tool 704 may be configured at a proximal end of the head portion 718 with a fitting, such as a Luer fitting, for making connection with a syringe or other fluid manipulation apparatus. The head portion 726 of the sheath tool 706 includes handle tabs 733, which facilitate easy handling and manipulation of the sheath tool, and which may be used to exert a force to snap apart the head portion 726 into two halves to facilitate break-away removal of the break-away sheath 726 from around an object that may be disposed within the internal passage of the break-away sheath 728.

With continued reference to FIG. 26, the implant device 708 includes a conduit 734 and a head 736. The head 736 is located adjacent a proximal end 738 of the implant device 708 and the conduit 734 extends distal of the head 736 to a distal end 740 of the implant device 708. The conduit 734 is configured for being disposed through a fistula and includes exterior surface features in the form of circumferential ridges 742 and recessed areas between the ridges 742 to engage tissue within the fistula and help anchor the implant device 708 when implanted. The implant device 708 may, for example, be or have features as disclosed elsewhere herein (e.g., FIGS. 3-15 and related discussion). The implant device 708 has an internal passage that passes through the entire length of the implant device 708 from the proximal end 738 to the distal end 740. The internal passage of the implant device 708 may be configured so that the working member 712 may be inserted through the internal passage of the implant device 708 to mount the implant device 708 on the working member 712. The implant device 708 may have longitudinal length significantly shorter than a longitudinal length of the working member 712. The working member 712 may have a length that is at least as long as a combined length of the break-away sheath 728 and the dilator member 728, or the working member may even have a length that is at least as long as or longer than a combined length of the implant device 708 and the sheath tool 706.

Figure 27:
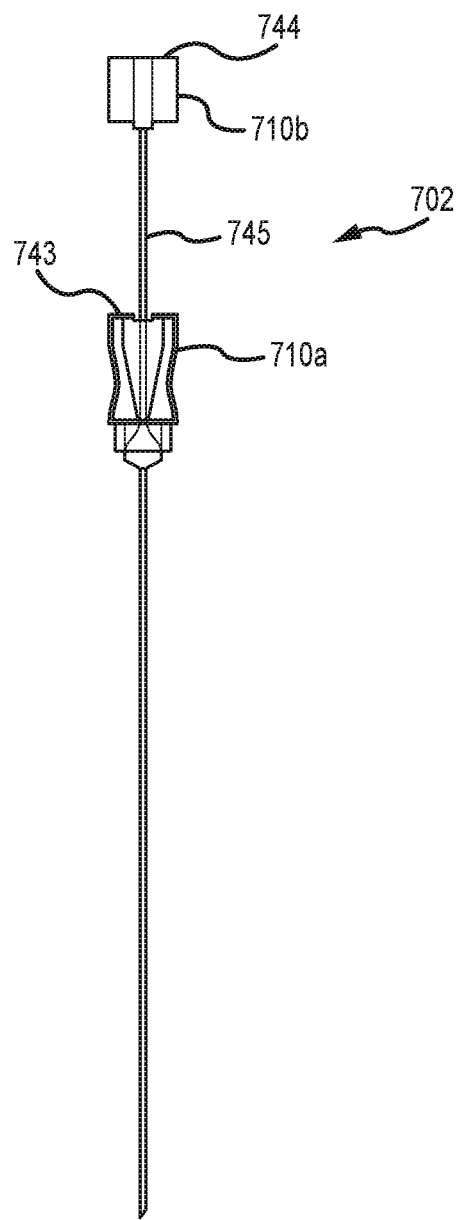
FIG. 27 is an illustration of an embodiment of a piercing tool that may be included in an implantation kit.

The piercing tool 702 may be comprised of two pieces, a hollow piece including the working member 712 in the form of a hollow member needle (e.g., hollow needle or cannula) and an insert pierce including a solid member (e.g., stylet) insertable through the hollow working member 712. FIG. 27 shows such a two-piece configuration for the piercing tool 702, including a hollow piece 743 and an insert piece 744 with a solid member 745 shown partially inserted into the hollow piece. As described previously, use of a needle/stylet or cannula/stylet configuration to form a fistula may avoid coring tissue that might otherwise occur if tissue is pierced with a hollow member to form a fistula. As shown in FIG. 27, the hollow piece 743 includes a portion 710*a* of the handle portion 710 (FIG. 26) and the insert portion 743 includes a portion 710*b* of the handle portion 710 (FIG. 26). In the configuration of the piercing tool 702 shown in FIG. 27, the hollow piece 743 would function as an implantation tool (including the working member 712 as a hollow member) for the kit. Spinal needle/stylet assemblies may be used as such a two-piece piercing tool 702. As an alternative configuration, the piercing tool 702 could be of a single piece configuration including a solid member (e.g., a stylet) and no insert piece, in which case the piercing tool 702 would function as the implantation tool (including the working member 712 as a solid member) for the kit.

Figure 28:
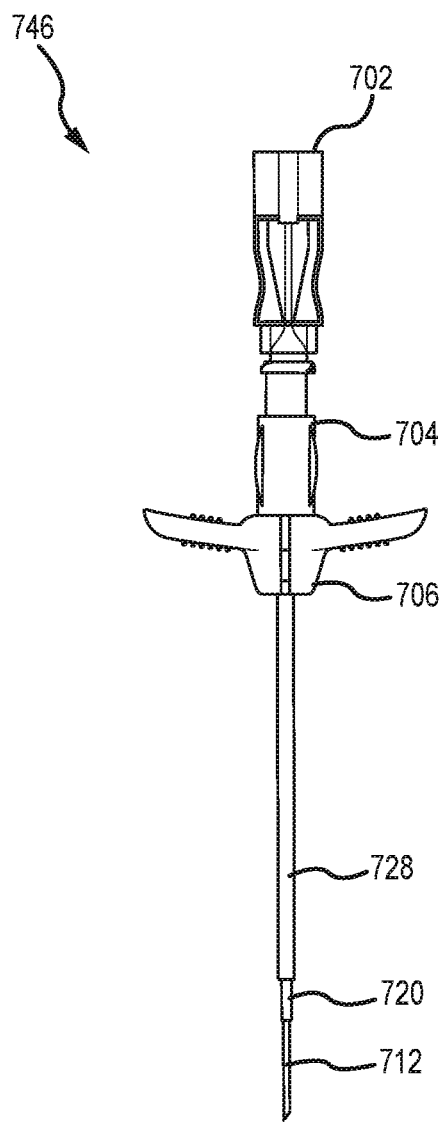
FIG. 28 is an illustration of a tool assembly including components of the implantation kit embodiment of FIG. 26.
Figure 30:
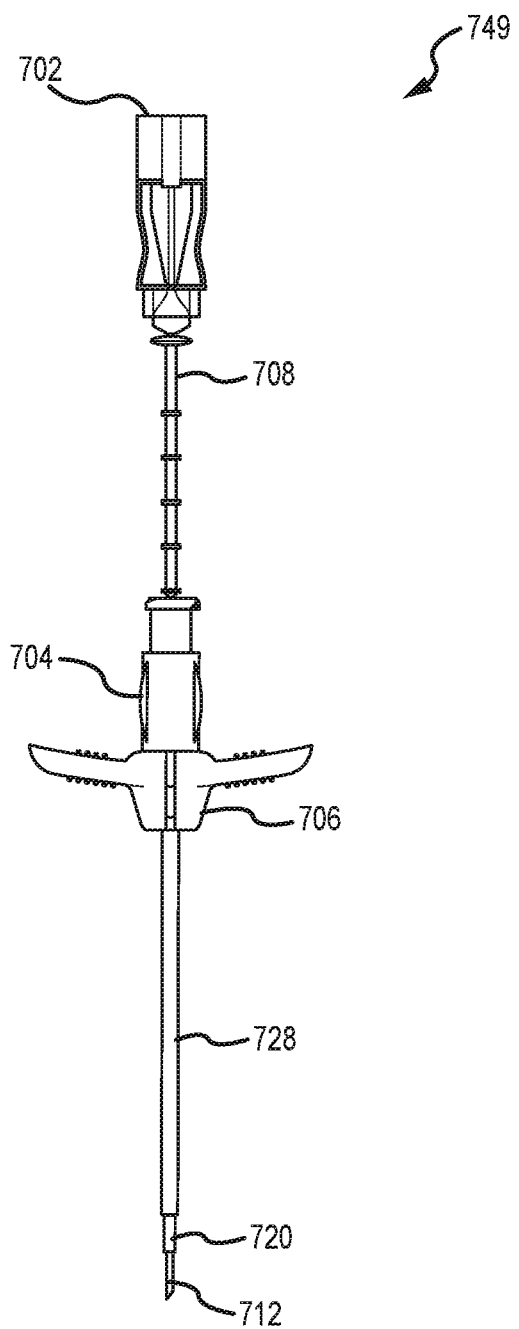
FIG. 30 is an illustration of a tool assembly including components of the implantation kit embodiment of FIG. 26.

With continued reference to FIG. 26, the piercing tool 702, dilator tool 704 and sheath tool 706 may be assembled together, and either together with or in the absence of the implant device 708, in tool assembly configurations that may be useful for piercing tissue and forming a fistula through the tissue. When in such a tool assembly configuration, the working member 712 is inserted through the internal passage of the dilator tool 704 and the working member 712 and dilator member 720 combination is inserted through the internal passage of the sheath tool 706, so that the dilator member 720 will be annularly disposed between the working member 712 and the break-away sheath 728. By annularly disposed, it is meant that the dilator member 720 may be located in an annular area between the working member 712 and the break-away sheath 728. In this configuration, a distal portion of the dilator member 720 may be exposed distal of the distal end 732 of the sheath tool 706 and a distal portion of the working member 712 may be exposed distal of the distal end 724 of the dilator tool 704. FIG. 28 shows an example of a tool assembly 746 with such a configuration including the piercing tool 702, dilator tool 704 and sheath tool 706 of the kit of FIG. 26, but not including the implant device 708. FIG. 30, discussed further below, shows an example tool assembly 748 with such a configuration including the piercing tool, 702, dilator tool 704, sheath tool 706 and implant device 708.

Figure 29:
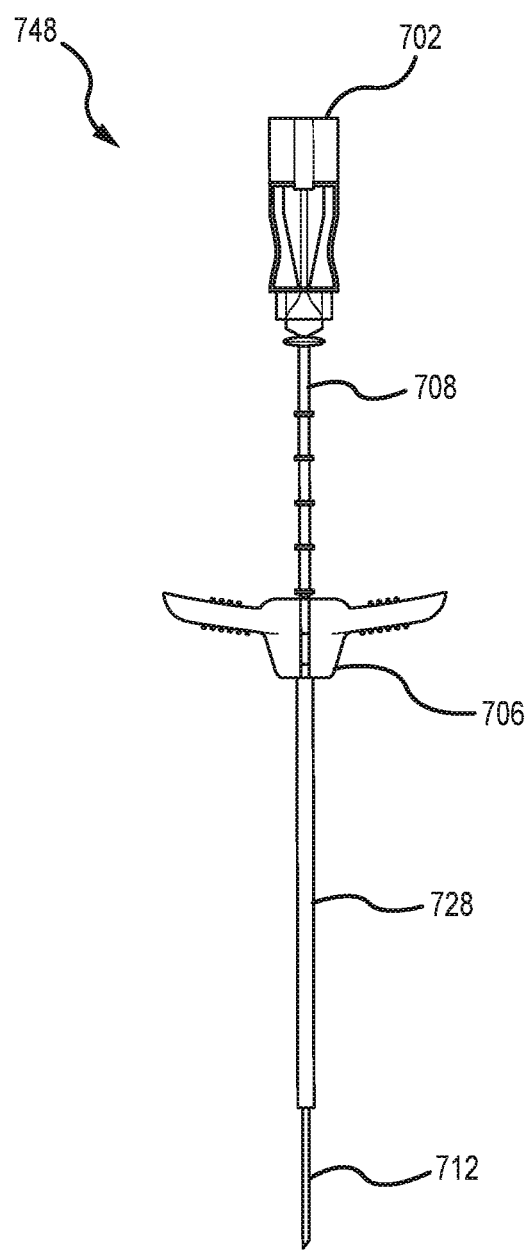
FIG. 29 is an illustration of a tool assembly including components of the implantation kit embodiment of FIG. 26.

With reference again to FIG. 26, the piercing tool 702 (or a hollow piece component thereof), sheath tool 706 and implant device 708 are assemblable, in the absence of the dilator tool 704, into a tool configuration useful for implantation of the implant device 708 to provide an artificial fluid path in fluid communication with the lacrimal apparatus within the orbit and with the proximal end 738 of the implant device 708 disposed in the lacrimal apparatus, for example within the orbit. In such a tool assembly configuration, the implant device 708 may be mounted on the working member 712 with the working member 712 inserted through the internal passage of the implant device 708 from the proximal end 738 of and out of the distal end 740 of the implant device 708. With the implant device 708 mounted on the working member 712, the working member 712 may be inserted into the internal passage of the sheath tool 706. In one preferred implementation, the exterior width of the conduit 734 of the implant device 708 and the internal passage of the sheath tool 706 may be configured so that implant device 708 may not be inserted into the internal passage of the sheath tool 706. In an alternative implement, the configuration of the implant device 708 and the sheath tool 706 may be such that the at least a portion of the implant device may be inserted into the internal passage of the sheath tool 706, but the implant device 708 may not be passed through the entire length of such internal passage. FIG. 29 shows and example of such a tool assembly configuration 748 including the piercing tool 702, sheath tool 706 and implant device 708, but not including the dilator tool 704 (FIG. 26). In an implementation when the piercing tool 702 includes a two-component structure with a hollow piece and an insert piece (e.g., FIG. 27), such a tool assembly configuration may or may not include the insert piece (e.g., insert piece 744 of FIG. 27).

Dilator/sheath combinations are available for vascular applications and may be used to provide the dilator tool 704 and the sheath tool 706 as shown in FIG. 26. Vascular dilation sheaths, however, typically may have a tapered end that may not provide an internal passage sufficiently large for passing a needle, stylet or cannula of appropriate size for use as the working member 712. It has been found that the restriction of the tapered end may be removed (e.g., by cutting the tapered end off with scissors) to accommodate passage of a working member 712 of an appropriate size through the dilator member 720. The break-away sheaths on such vascular dilation tools may be made from polytetrafluoroethylene (PTFE), which has a property of peeling apart when removed in a break-away manner, which is beneficial for vascular applications. One issue with polytetrafluoroethylene is that it is difficult to form a tubular wall with sufficient rigidity to effectively function as a dilator, thus the use of a separate dilator member insert to maintain the structural integrity of such a polytetrafluoroethylene break-away sheath during dilation operations. Although as noted such a vascular dilator/sheath combination, or similar dilator/sheath tool combinations, may be used with the present invention, in some implementations, a sheath tool may be provided with mechanical properties (e.g., rigidity) sufficient to permit the sheath tool to provide both the dilator functionality and the break-away functionality. In some preferred implementations, such sheath tools may include a break-away sheath made from a material other than polytetrafluoroethylene. For example, such a sheath tool with sufficient mechanical properties for acting as a dilator prior to being broken away may be made from a polymeric material for example based on polyethylene, polypropylene, polycarbonate, or acrylonitrile butadiene styrene polymer (ABS polymer).

As noted above, components of the kit of FIG. 26 may be assemblable into a tool assembly configuration including all of the piercing tool 702, the dilator tool 704, the sheath tool 706 and the implant device 708, and such a tool assembly configuration may be used to form a fistula through which the implant device 708 may be implanted, as an alternative to using the example configuration of the tool assembly 746 shown in FIG. 28. FIG. 30 shows an example of a tool assembly 749 with a configuration including the piercing tool 702, dilator tool 704, sheath tool 706, and implant device 708, and with a distal portion of the dilator member 720 exposed distal of the break-away sheath 728 and with a distal portion of the working member 712 exposed distal of the dilator member 720. Such a tool assembly configuration 749 could be used, for example, as an alternative to the example tool assembly 746 of FIG. 28 for forming a fistula, including dilating the fistula to the outer width of the break-away sheath 728. Using such a tool assembly 749 as shown in FIG. 30 may provide an advantage in that it may not be necessary to perform the extra step of mounting the implant device 708 on the working member 712 after forming the fistula, to prepare the tool assembly 748 of FIG. 29. Rather, all that would be required would be to retract the working member 712 from the sheath tool 706, remove the dilator tool 704 and reinsert the working member 712, either with or without a solid member (e.g., stylet) disposed through the working member 712 when the working member 712 is a hollow member.

Figure 31:
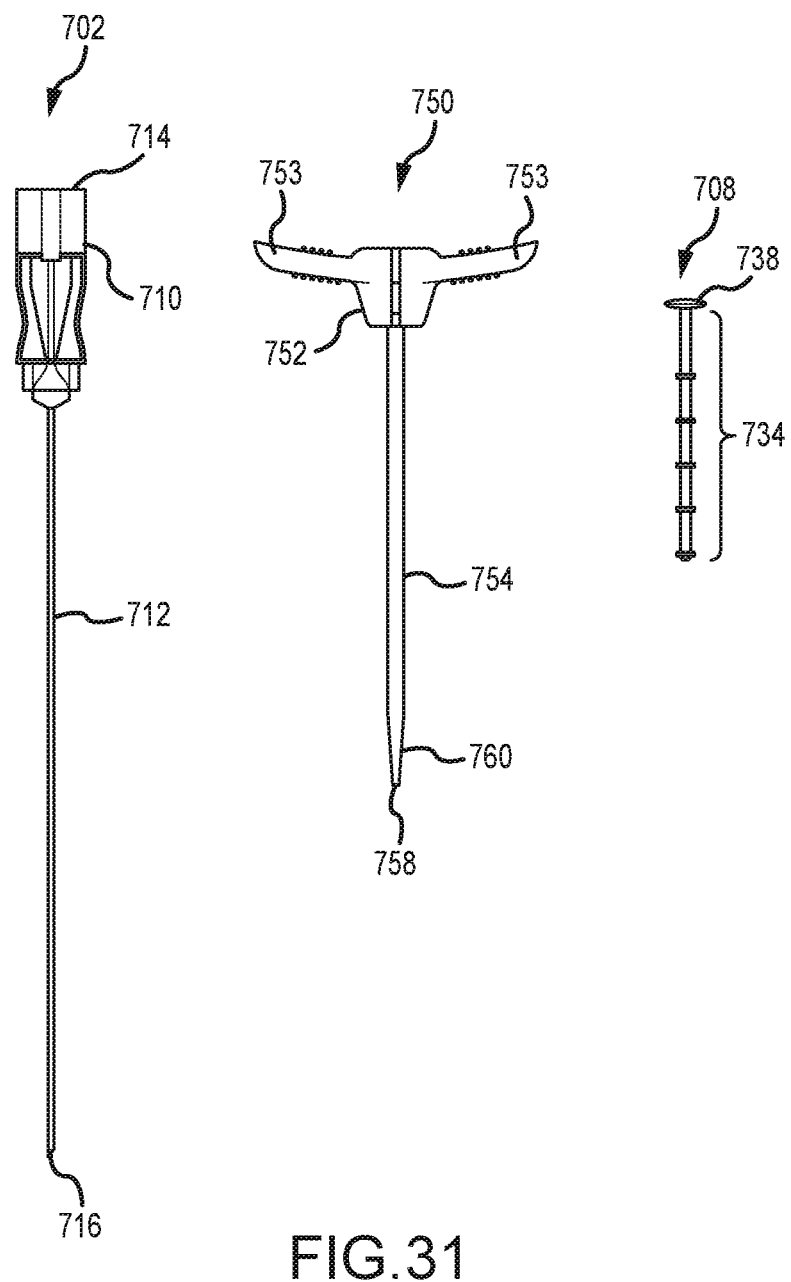
FIG. 31 is an illustration of components of an embodiment of an implantation kit.

Reference is now made to FIG. 31, which illustrates components for an implantation kit including a sheath tool that functions also as a dilator, thus eliminating the need for a separate dilation tool. The implantation kit may include additional components to those shown in FIG. 31. As shown in FIG. 31, the implantation kit includes the piercing tool 702 and the implant device 708 as shown in FIG. 26. The piercing tool 702 may be a two-piece construction (e.g., FIG. 27) or single-piece construction (e.g., FIG. 27). The implantation kit also includes a sheath tool 750 that provides both dilation and break-away functionality. The sheath tool 750 has a head portion 752 and a break-away sheath 754 that extends longitudinally away from the head portion 752 to a distal end 758 at a distal end of the break-away sheath 754. The sheath tool 750 may have a similar configuration to that shown for sheath tool 706 in FIG. 26, but designed to function also as a dilator. In that regard, the break-away sheath 754 may be made of a material providing enhanced mechanical properties for use as a dilator relative to polytetrafluoroethylene, such as one of the polymeric materials previously noted. The sheath tool 750 also includes a tapered portion 760 adjacent the distal end 758. The tapered portion 760 assists in facilitating fistula dilation during a procedure to form a fistula of an appropriate dilated size. The internal passage through the sheath tool 750 is appropriately sized at the distal end 758 to permit passage of the working member 712 with a relatively close tolerance. The head portion 752 of the sheath tool 750 includes handle tabs 753 that facilitate manipulation of the sheath tool 750, including to exert a force to cause the head portion to snap in half for break-away removal of the break-away sheath 754. Rather than the break-away sheath 754 peeling apart as might be the case for polytetrafluoroethylene, the break-away sheath 754 may be made with mechanical properties so that it may essentially snap into two halves over the entire length of the break-away sheath 754 when the head portion 752 is snapped open. This may be the case for example when the break-away sheath is made of a polymeric material other than PTFE, such as the polymeric materials previously noted.

Figure 32:
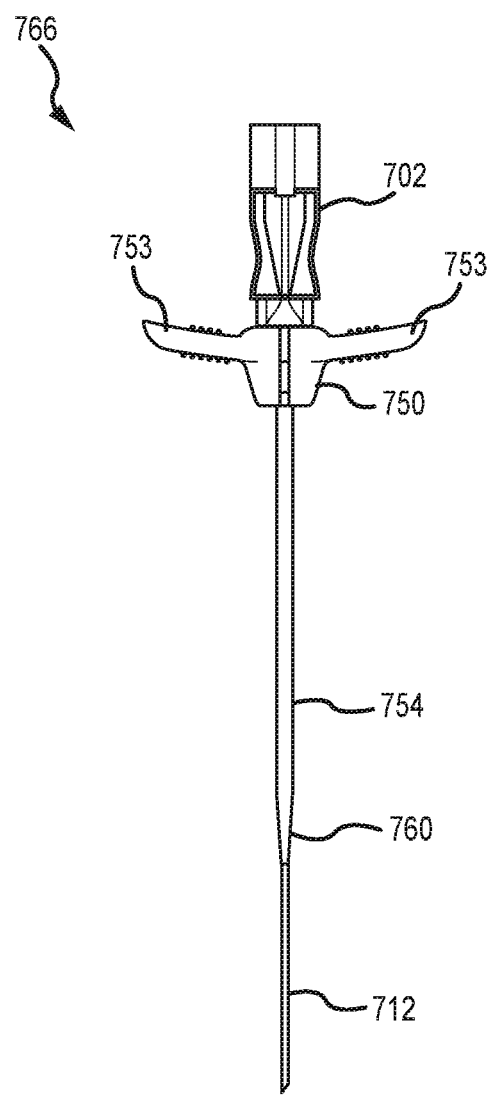
FIG. 32 is an illustration of a tool assembly including components of the implantation kit embodiment of FIG. 31.

With continued reference to FIG. 31, the piercing tool 702 and the sheath tool 750 are assemblable, in either in the absence of the implant device 708 or together with the implant device 708, in tool assembly configurations similar to those described with respect to FIGS. 28 and 30, except not including a separate dilator member, because the dilator function may be provided by the break-away sheath 754. Reference is now made to FIG. 32 showing an example tool assembly 766 with such a configuration including the piercing tool 702, and sheath tool 750 of FIG. 31, but not including the implant device 708. In the tool assembly 766, the working member 712 is inserted through the internal passage of the sheath tool 750 with a distal portion of the working member 712 exposed distal to the break-away sheath 754. With the tool assembly, a piercing tip at the distal end of the working member 712 may pierce tissue to initiate formation of a fistula, and then the sheath tool 750 may be advanced to cause dilation of the fistula to the maximum external width of the break-away sheath 754 located proximal of the distal tapered portion 760.

Figure 33:
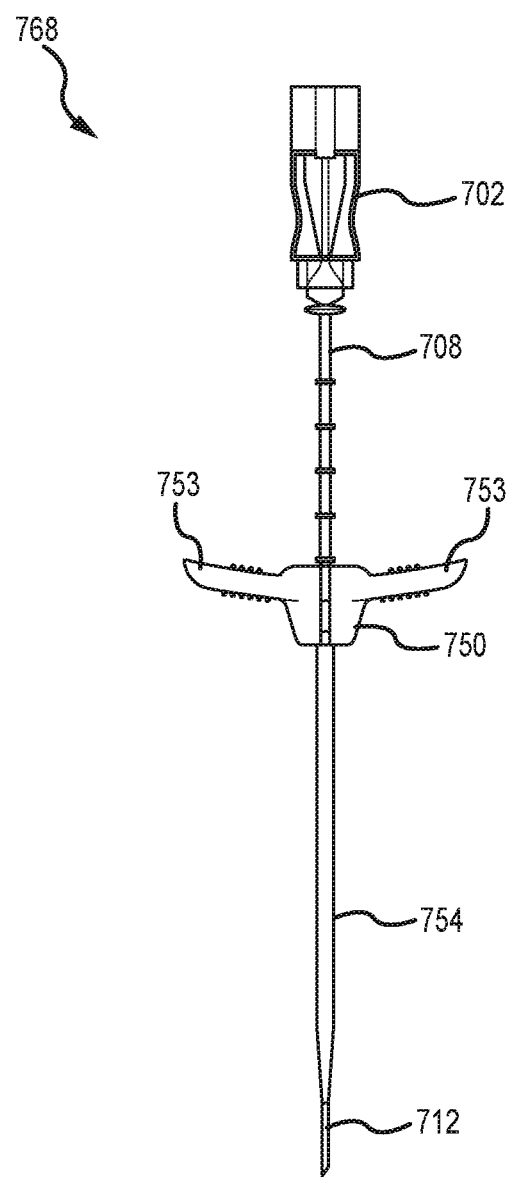
FIG. 33 is an illustration of a tool assembly including components of the implantation kit embodiment of FIG. 31.

An example tool assembly 768 with a configuration including the piercing tool 702, the sheath tool 754 and the implant device 708 is shown in FIG. 33. The configuration of the tool assembly 768 may be used to form the fistula and/or to facilitate implantation of the implant tool 708 following formation of the fistula. In the tool assembly 768, the implant device 708 is mounted on the working member 708 and the working member is inserted through the break-away sheath with at least a portion of the implant device 708 disposed proximal of the break-away sheath 754, and preferably with at least a portion of the implant device 708 disposed proximal of the sheath tool 750.

With continued reference to FIG. 33, the tool assembly 768 may have a distal portion of the working member 712 exposed distal of the break-away sheath 754. In one implementation, the tool assembly may be used to form the fistula, rather than a tool assembly such as the tool assembly 766 of FIG. 32. A piercing tip of the piercing tool 702 may form an initial fistula, and the sheath tool 750 may then be advanced (e.g., using the handle tables 753) to dilate the fistula to a size of the exterior width of the break-away sheath 754 above the tapered portion 760. Using the tool assembly 768 to form the fistula may have the advantage of not requiring disengagement of the working member from the break-away sheath 754 to mount the implant device 708 on the working member 712 after formation of the fistula. Rather, after forming the fistula, the sheath tool 750 may be removed by break-away removal to remove the break-away sheath 754 from around the working member 712 (e.g., through manipulation of handle tabs 753) and the implant device 708 may then be advanced over the working member and into place extending through the fistula for implantation.

With reference again to FIG. 31, the break-away sheath 754 of the sheath tool 750 may be configured with break-away structural features permitting the break-away sheath 754 to be removed in a desired break-away fashion. Such break-away structural features may, for example, include predetermined break points in the head portion 752 and along the length of the break-away sheath 754, scoring of the material of the break-away sheath 754 and/or head portion 752 (such as with a laser grinder or other tool) to provide a predetermined failure path, or a tear strip may be embedded along the length of the sheath tool 750 that may be torn-away to destroy the structural integrity of the break-away sheath wall along a predetermined tear line.

Figure 34:
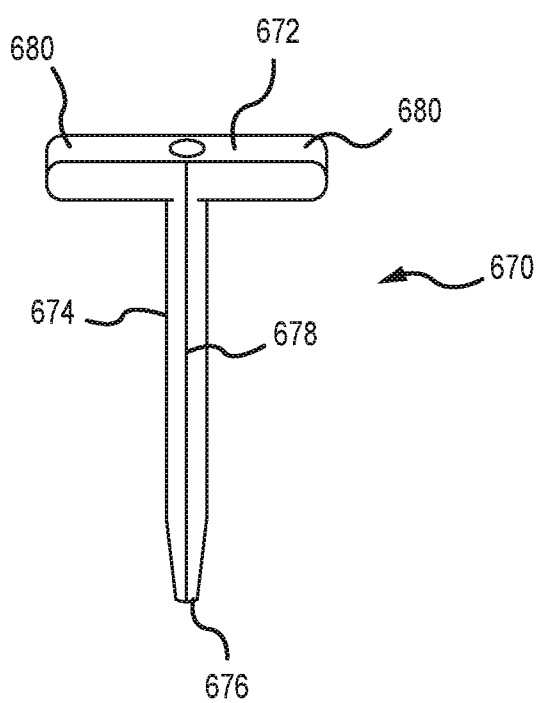
FIG. 34 is an illustration of a sheath tool.

Reference is now made to FIG. 34, which shows one example of a sheath tool 670 that may be used to provide both break-away sheath functionality and dilator functionality (e.g., may be used instead of the sheath tool 750 in the implantation kit of FIG. 31 and tool assemblies of FIGS. 32 and 33). The sheath tool 670 includes a head portion 672 and a break-away sheath portion 674 extending from the head portion 672 to a distal end 676 of the sheath tool 670. The sheath tool 670 includes two score lines 678 disposed on opposing sides of the sheath tool 670 and extending down the full length of the sheath tool 670. The score lines 678 represent areas where the structural integrity of the sheath tool 670 has been reduced to provide a failure path for break-away removal of the break-away sheath 674. The head portion 672 includes handle tabs 680 that facilitate hand manipulation of the sheath tool 670, including to provide leverage points for exerting sufficient force to cause the sheath tool 670 to break into two pieces along the predetermined failure path of the score lines 678 for break-away removal of the break-away sheath 674 to expose a member (e.g., a working member) that may be disposed through the break-away sheath 674 during use. The sheath tool 670 may be manufactured as a single molded (e.g., injection molded) piece, such as of a polyethylene, polypropylene, polycarbonate or acrylonitrile butadiene styrene polymer composition.

Reference is now made to FIGS. 35-43 in relation to an example implementation of a method of implanting an implant device to provide an artificial fluid path and fluid communication with the lacrimal apparatus within the orbit. A similar procedure may also be followed to access the nasolacrimal duct subcutaneously or through the mouth, for example, to implant an implant device to provide an artificial fluid path in fluid communication with the lacrimal apparatus within the nasolacrimal duct. For illustration purposes, the example procedure shown in FIGS. 35-43 uses the components of the implantation kit shown in FIG. 26 with a two-piece configuration for the piercing tool 702 shown in FIG. 27, and using specifically the tool assemblies shown in FIGS. 28 and 29. Anatomical features shown in FIGS. 35-43 are identified with the same reference numerals as used in FIGS. 1,3 and 20-24.

Figure 35:
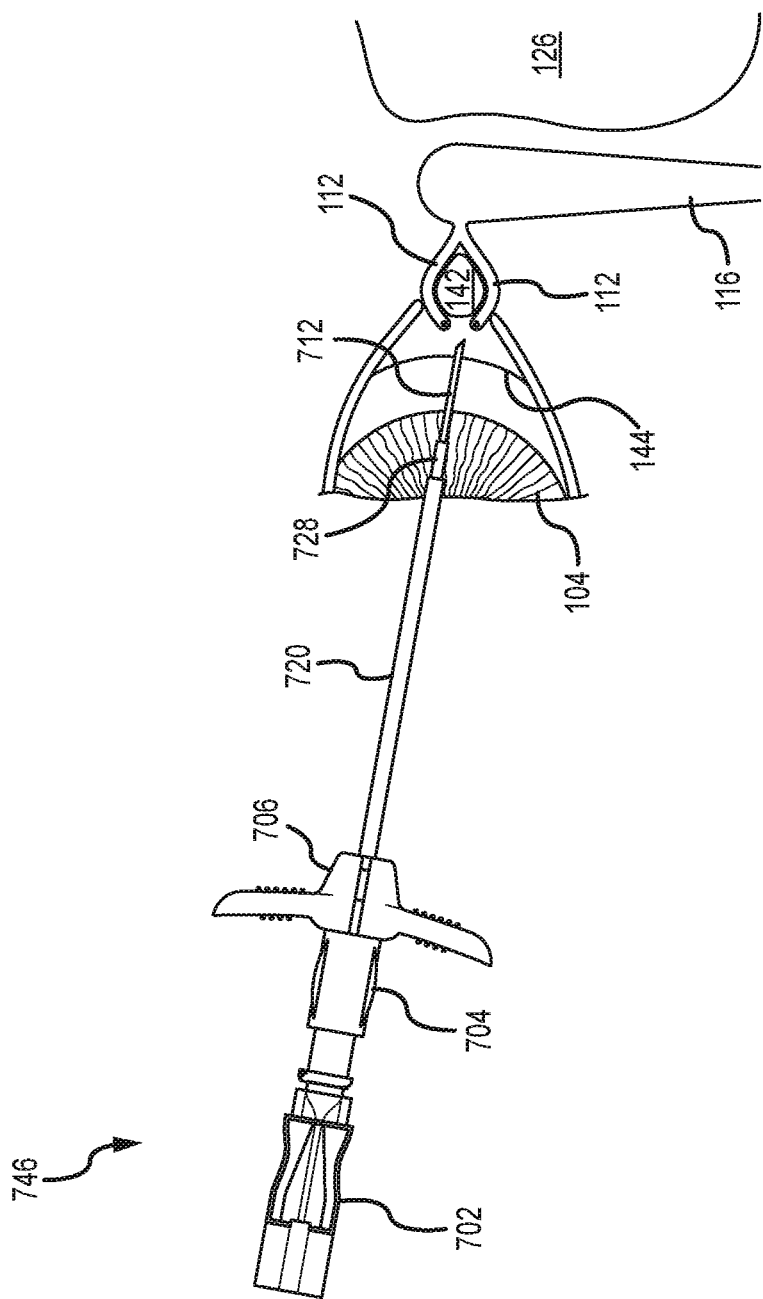
FIG. 35 is an illustration of a tool assembly positioned in preparation for performing a procedure to implant an implant device to provide an artificial fluid path from the lacrimal apparatus within the orbit to an ethmoid sinus.
Figure 36:
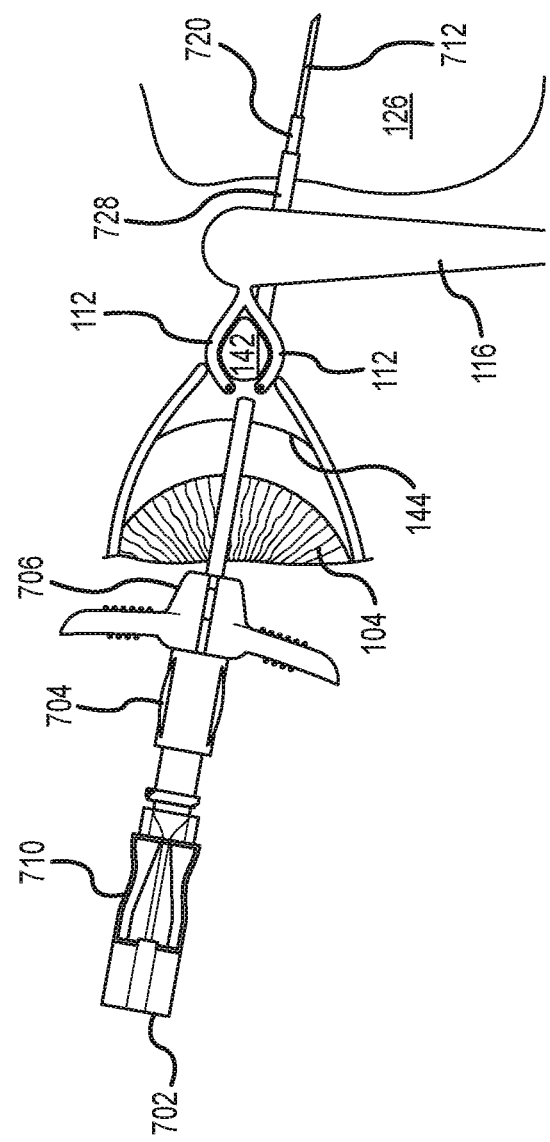
FIG. 36 is an illustration of a tool assembly positioned during a procedure to implant an implant device to provide an artificial fluid path from the lacrimal apparatus within the orbit to an ethmoid sinus.

FIG. 35 shows the tool assembly 746 of FIG. 28 positioned for forming a fistula between the orbit and the ethmoid sinus 126. The proximal end of the fistula is to be located in the orbit between the lacrimal caruncle 142 and plica semilunaris 144. FIG. 36 shows the tool assembly 746 with the working member 712, dilator member 720 and break-away sheath 728 advanced to form a fistula between the orbit and the ethmoid sinus 126, dilated to the exterior width of the break-away sheath 728. This may be accomplished by a medical professional advancing the tool assembly 746 until the medical professional feels the advancing tip of the working member 712 puncture through the tissue separating the orbit and the ethmoid sinus 126. The medical professional may then continue to advance the tool assembly 746 as a unit to advance the dilator member 720 and break-away sheath 728 to dilate the initial fistula. Alternatively, the medical professional may advance the combined dilator tool 704 and sheath tool 706 over the working member 712 while holding the piercing tool 702 and the working member 712 substantially stationary. The latter approach may provide an advantage of reducing a possibility that a piercing tip of the piercing tool 702 may be advanced to a point of inadvertently piercing tissue on a distal side of the ethmoid sinus 126. With the later approach, the head portion 710 of the piercing tool 702 may be somewhat retracted from to the dilator tool 704 relative to the relative positioning of the piercing tool 702 and the dilator tool 704 shown in FIG. 36.

Figure 38:
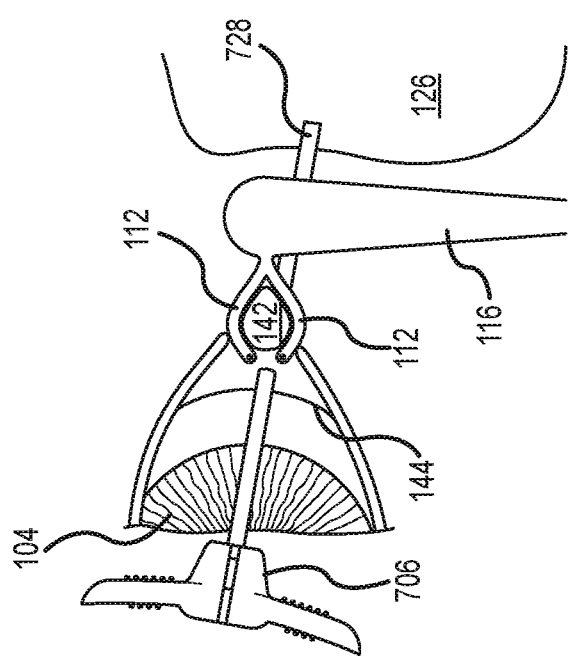
FIG. 38 is an illustration of a sheath tool positioned during a procedure to implant an implant device to provide an artificial fluid path from the lacrimal apparatus within the orbit to an ethmoid sinus.

After the fistula of a desired dilated size has been formed by advancing the working member 712, dilator member 720 and break-away sheath 728 through tissue between the orbit and the ethmoid sinus 126, then the piercing tool 702 and the dilator tool 704 may be retracted to remove the working member 712 and the dilator member 720 from the break-away sheath 728, and to permit disengagement of the piercing tool 702 and the dilator tool 704 from the sheath tool 706. FIG. 38 shows the sheath tool 706 remaining in position with the break-away sheath 728 disposed through the fistula into the ethmoid sinus 126 following disengagement of the piercing tool 702 and dilator tool 704. As shown in FIG. 38, the sheath tool 706 maintains control of the location of the fistula to facilitate performance of further operations as part of the implantation procedure.

Figure 37:
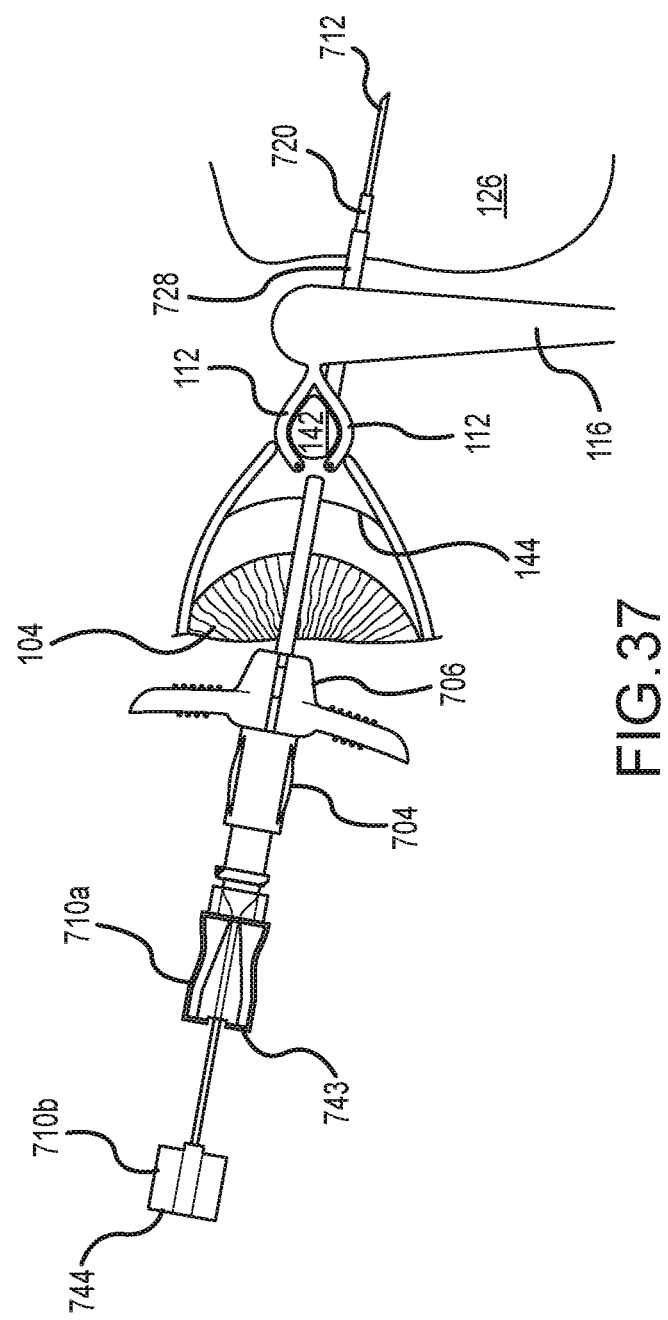
FIG. 37 is an illustration of a tool assembly positioned during a procedure to implant an implant device to provide an artificial fluid path from the lacrimal apparatus within the orbit to an ethmoid sinus.

Optionally, one or more procedures may be performed prior to disengaging the working member 712 and the dilator tool 704 from the sheath tool 706. Referring to FIG. 37, the insert piece 744 may be retracted and disengaged from the hollow piece 743, and one or more fluids may be injected through the hollow working member 712. For example, contrast media may be injected through the hollowing working member 712 and may be imaged to confirm that the fistula has been formed to the proper location prior to proceeding with implantation. The injection of contrast media may be from a syringe or other fluid manipulation apparatus, such as may be connected through a fitting (e.g., Luer fitting) provided adjacent the proximal end of the hollow piece 743. Alternatively, the insert piece 744 may be refracted after the working member 712 has punctured through to the ethmoid sinus 126, but before the dilator member 720 and the break-away sheath are advanced to dilate the initial fistula formed by the working member 712. Contrast media may be injected through the hollow piece 743 and imaged to confirm proper location of the initial puncture prior to advancing the dilator member 720 and the break-away sheath 728 to dilate the initial fistula formed by the initial puncture with the piercing tool 702.

Figure 39:
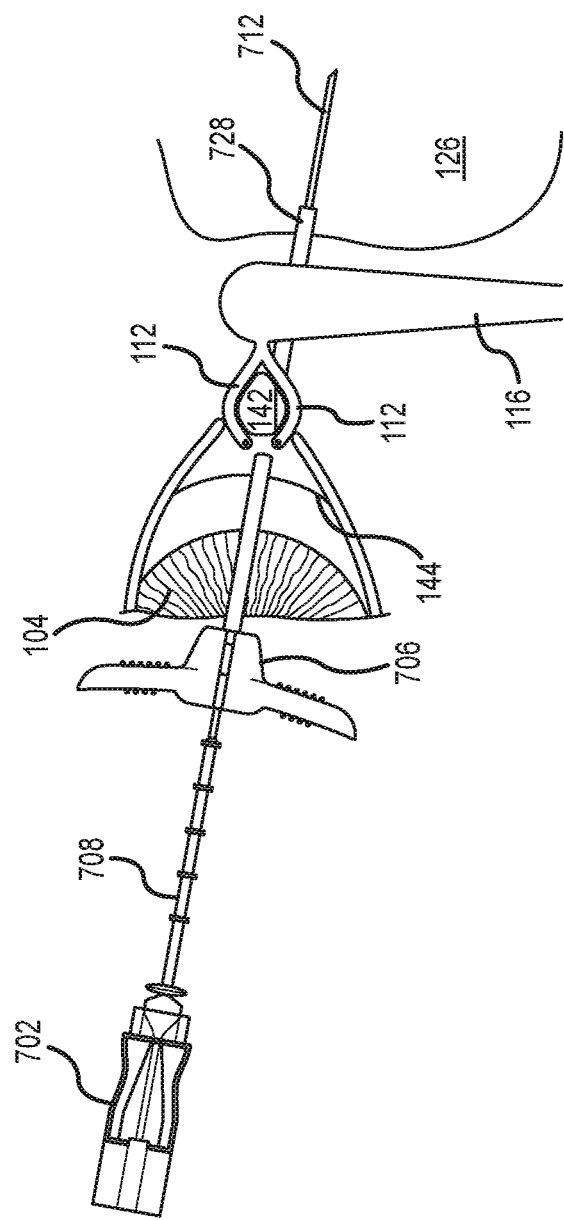
FIG. 39 is an illustration of a tool assembly positioned during a procedure to implant an implant device to provide an artificial fluid path from the lacrimal apparatus within the orbit to an ethmoid sinus.

After disengagement of the piercing tool 702 and the dilator tool 704 from the sheath tool 706, then the implant device 708 may be mounted on the working member 712 and the working member 712 reinserted into the break-away sheath 728 to position the implant device 708 for implantation. FIG. 39 shows the implant device 708 mounted on the working member 712 of the piercing tool 702 with a portion of the working member 712 distal of the implant device 708 inserted through the break-away sheath 728 of the sheath tool 704. As shown in FIG. 39, the piercing tool 702, sheath tool 704 and implant device 708 are assembled into a configuration of the tool assembly 748 shown in FIG. 29. As shown in FIG. 39, the tool assembly is positioned in an implantation position relative to the fistula to accommodate implantation of the implant device 708 through the fistula to form an artificial fluid path between the lacrimal apparatus within the orbit and the ethmoid sinus 126. Implantation of the implant device 708 involves removing the break-away sheath 728 from around the working member 712 to permit the implant device 708 to be positioned in the fistula in an implantation position.

Figure 40:
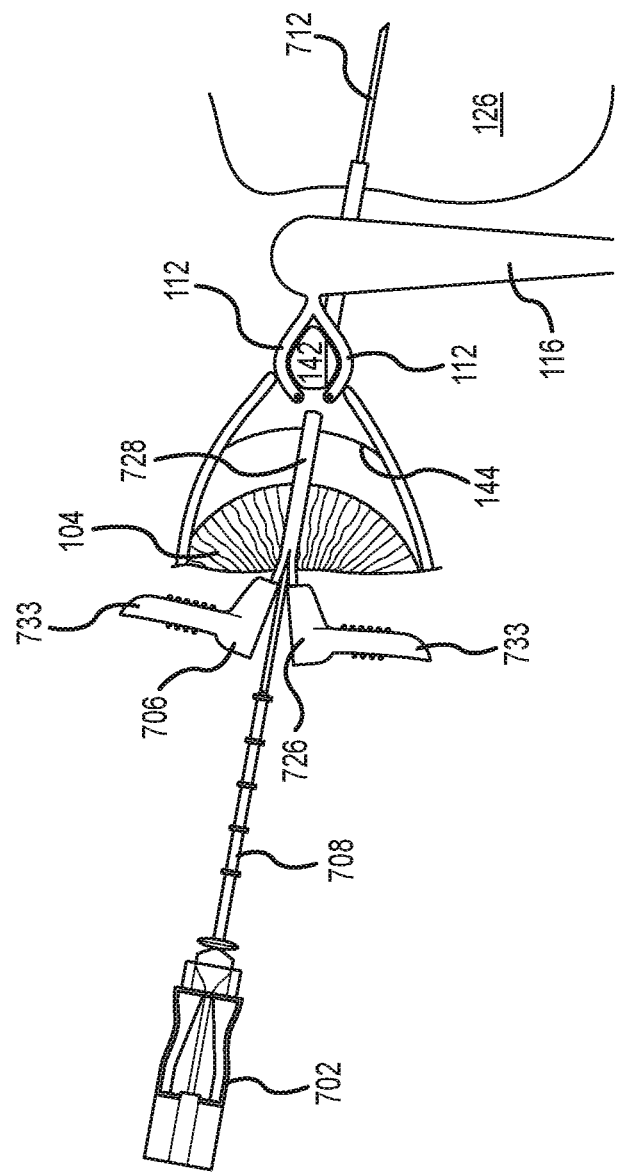
FIG. 40 is an illustration of a tool assembly positioned during a procedure to implant an implant device to provide an artificial fluid path from the lacrimal apparatus within the orbit to an ethmoid sinus.
Figure 41:
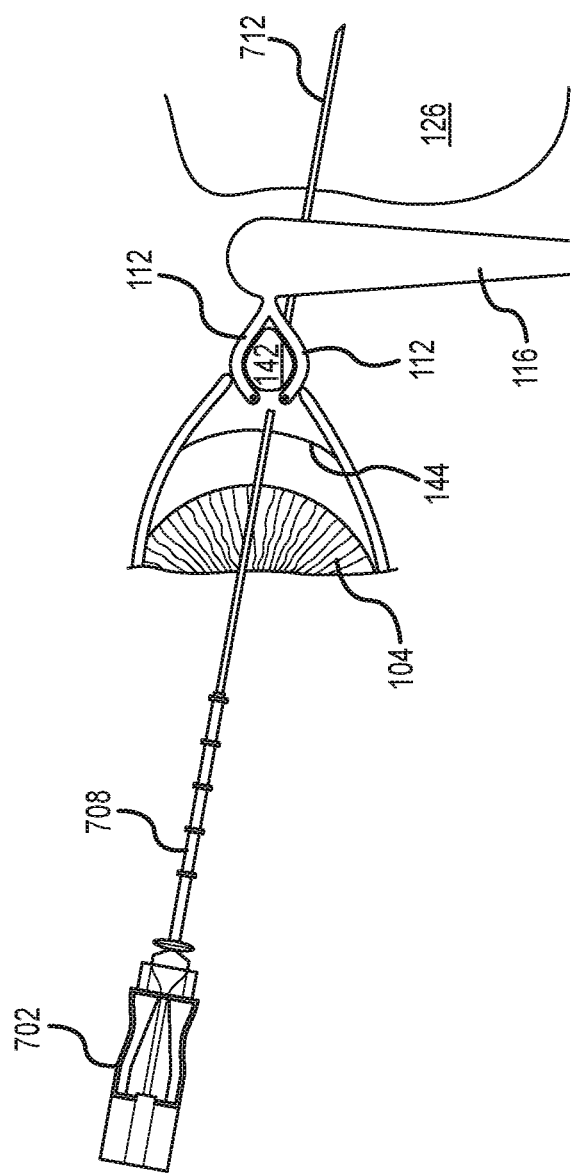
FIG. 41 is an illustration of a tool assembly positioned during a procedure to implant an implant device to provide an artificial fluid path from the lacrimal apparatus within the orbit to an ethmoid sinus.
Figure 42:
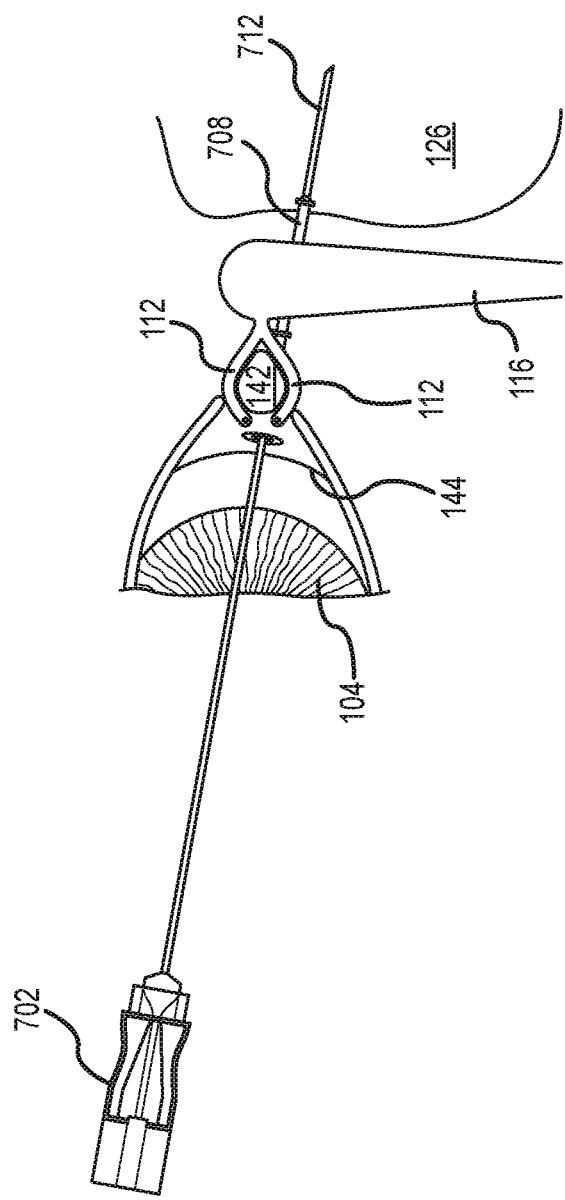
FIG. 42 is an illustration of a tool assembly positioned during a procedure to implant an implant device to provide an artificial fluid path from the lacrimal apparatus within the orbit to an ethmoid sinus.
Figure 43:
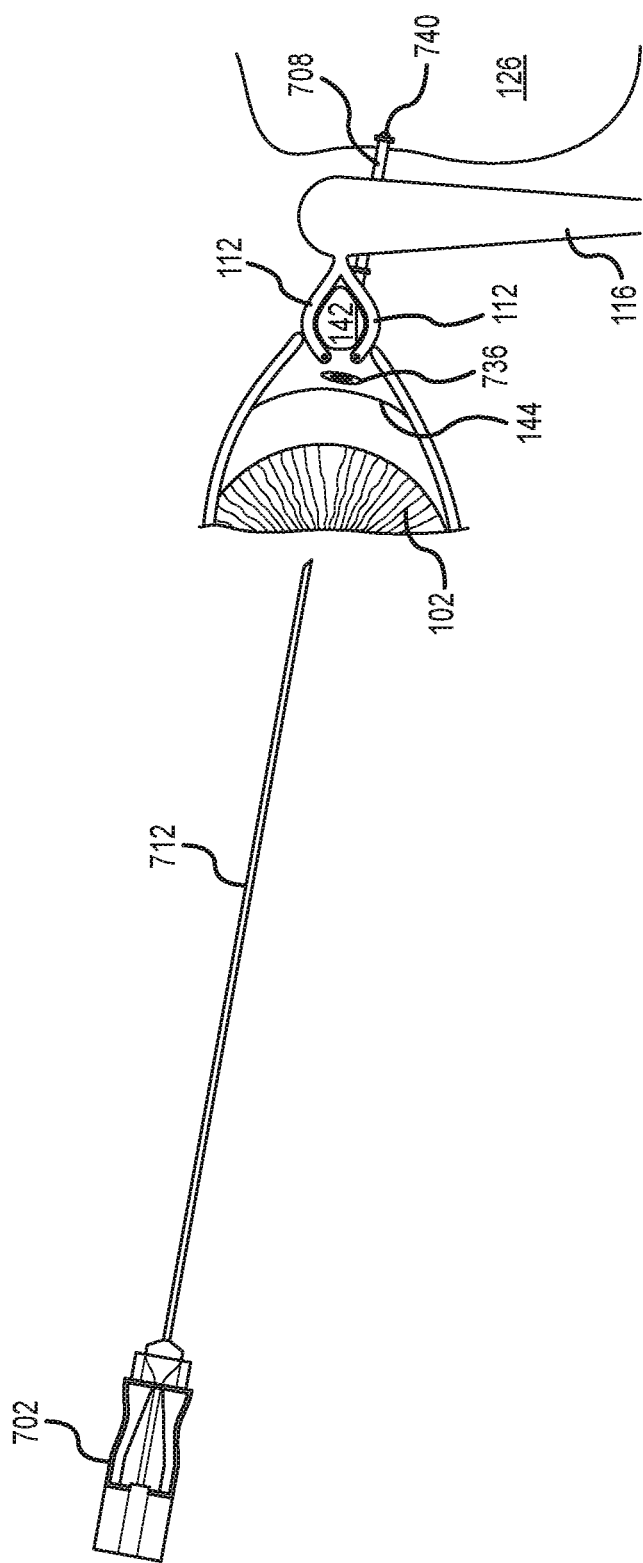
FIG. 43 is an illustration showing an implant device implanted following implantation to provide an artificial fluid path from the lacrimal apparatus within the orbit to an ethmoid sinus

FIG. 40 shows break-away removal of the break-away sheath 728 from around the working member 712. As shown in FIG. 40, the handle tabs 733 of the sheath tool 706 may be manipulated to snap the retaining mechanism in the handle portion 726 of the sheath tool 706 and to permit a peeling apart of the break-away sheath 728. As the break-away sheath 728 is peeled apart, the implant device 708 may be advanced toward the fistula and the break-away sheath 728 may be retracted from the fistula until it has been completely removed from the fistula and completely removed from around the working member 712. FIG. 41 shows the piercing tool 702 and the implant device 708 following complete removal of the sheath tool 706. FIG. 42 shows the implant device 708 in an implantation position within the fistula after having been advanced along the working member 712 and manipulated for desired positioning through the fistula. After the implant device 708 has been positioned in an implantation position, the piercing tool 702 may be retracted from the fistula and disengaged from the implant device 708 to leave the implant device 708 in place for the implantation with the head 736 of the implant device 708 located in the lacrimal apparatus within the orbit and with the distal end 740 of the implant device 708 located in the ethmoid sinus 126, as shown in FIG. 43. Either before or after retraction of the piercing tool 702, the implant device 708 may be rotated to position the head 736 in a desired orientation, for example to orient the head 736 with a length in a vertical direction and a narrower width in a horizontal direction, as shown in FIGS. 42 and 43.

A procedure similar to that described with reference to FIGS. 35-43 may also be performed using the components of the implantation kit shown in FIGS. 31-33 not including a separate dilator tool, and instead using a break-away sheath configured (including materials of construction) to provide sufficient mechanical properties to perform the dilation function as well as to provide the break-away capability. In that regard, the tool assembly 766 shown in FIG. 32 may be used to form a fistula in a manner similar to that shown in FIGS. 35 and 36, and the piercing tool 702 of the tool assembly 766 of FIG. 32 may be retracted to leave in place the sheath tool 750 with the break-away sheath 754 disposed through the fistula, similar to as shown in FIG. 38. The tool assembly 768 shown in FIG. 33 could then be formed by mounting the implant device 708 onto the working member 712 of the piercing tool 702 and inserting the distal portion of the working member 712 through the break-away sheath 754, but with the resulting tool assembly 768 of FIG. 33 positioned similar to the positioning shown in FIG. 39. Operations similar to those shown in FIGS. 40-43 could then be performed by snapping apart the head portion 752 and the break-away sheath 754 by applying sufficient force to the handle tabs 753, removing the sheath tool 750, positioning the implant device 708 through the fistula in an implantation position and retracting the working member 712 to disengage the implant device 708 and leave the implantation device 708 implanted through the fistula.

In a similar manner as just described, a procedure may involve forming the fistula with a tool assembly on which the implant device 708 is pre-mounted on the working member 708, for example using the tool assembly 749 shown in FIG. 30 or the tool assembly 768 shown in FIG. 33. In such a procedure, it would not be necessary to perform the extra step of mounting the implant device 708 on the working member 712 after forming the fistula and before positioning the implant device 708 for implantation. In the case of use of the tool assembly 768 shown in FIG. 33 to form the fistula, it may not be necessary to disengage the working member from the break-away sheath prior to positioning the tool assembly 768 in an implantation position relative to the fistula to facilitate implantation of the implant device 708.

A variety of medical treatments and procedures may be performed through a fistula formed between the lacrimal apparatus and a paranasal sinus, whether or not the fistula is durably patent. One or more medical devices may be inserted into the paranasal sinus through the fistula. For example a hollow working member (e.g., hollow needle, cannula) may be inserted through the fistula into the paranasal sinus to permit aspiration of fluid from or injection of a treatment formulation (e.g., drug formulation, irrigation fluid) into the paranasal sinus. As another example, a treatment formulation (e.g., drug formulation, irrigation fluid) may be transmitted through the fistula into the paranasal sinus by natural flow from the lacrimal system. A treatment formulation may be administered to the vicinity of the eye (e.g., as eye drops) to naturally flow from the lacrimal apparatus through the fistula and into the paranasal sinus. The fistula may, but need not necessarily be, a durably patent fistula. For example, a conduit of a medical device be inserted from the lacrimal apparatus through tissue and into the paranasal sinus, fluid may be aspirated through or injected from the conduit, and the conduit may then be removed to allow the fistula formed by insertion of the conduit to quickly repair. Such a conduit may, for example, be a hypodermic needle or cannula (e.g., connected to a syringe, drip system or other fluid injection/aspiration system). The fistula may be formed by insertion of a member including the needle or cannula and may naturally repair and close quickly following removal of the conduit. For example, the fistula may be formed by insertion of a hypodermic needle, a fluid may be injected or aspirated through the hypodermic needle and the hypodermic needle may then be removed to permit the fistula to repair. As another example, the fistula may be formed by a trocar/cannula assembly, the trocar may then be removed, a medical procedure performed through the cannula (e.g., fluid injection or aspiration), and the cannula may then be removed to permit the fistula to repair. As another example, the fistula may be formed by a cutting cannula, a medical procedure performed through the cannula (e.g., fluid injection or aspiration), and the cannula may then be removed to permit the fistula to repair.

A surgically created, durably patent fistula may be advantageously located for transmitting lacrimal fluid (tears) to a paranasal sinus. Lacrimal fluid from the lacrimal apparatus may be permitted to drain into the paranasal sinus. In one preferred implantation, the surgically-created, durably patent fistula is from either the orbit or the nasolacrimal duct to either the ethmoid sinus or the maxillary sinus, with a fistula route from the orbit being more preferred.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically incompatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

The features in the drawings are shown for illustration purposes and to generally show relative positioning and interaction, and the features shown are not necessarily to scale.

What is claimed is:

1. An implantation tool assembly for implantation of an implant device to provide an artificial fluid path in fluid communication with the lacrimal apparatus, the implantation tool assembly comprising:
   an implant device, the implant device comprising:
      a proximal end and a distal end at opposite longitudinal ends of the implant device;
      a first internal passage extending between the proximal end and the distal end of the implant device and having a first end open at the proximal end of the implant device and a second end open at the distal end of the implant device;
      a longitudinal length between the proximal end and the distal end of the implant device in a range of from 2 millimeters to 50 millimeters;
      a width of the first internal passage transverse to the length in a range of from 0.25 millimeter to 5 millimeters; and
      wherein, the implant device is configured to be implanted with the proximal end disposed in the lacrimal apparatus;
   an implantation tool with a proximal end and a distal end, the implantation tool comprising:
      a working member extending longitudinally in a direction from the proximal end toward the distal end of the implantation tool assembly; and
      a hand-manipulable handle connected with the working member and hand graspable proximal of the working member to hand manipulate the implantation tool;
      wherein, the working member is disposed through the first internal passage of the implant device with the proximal end of the implant device disposed toward the handle and the distal end of the implant device disposed toward the distal end of the implantation tool;
   a sheath tool with a proximal end and a distal end, the sheath tool comprising:
      a break-away sheath and a second internal passage extending longitudinally through the break-away sheath in a direction from the proximal end toward the distal end of the sheath tool;
      wherein, the sheath tool is configured to slidably receive at least a portion of the working member in the second internal passage, and at least a portion of the working member of the implantation tool is disposed in the second internal passage in the break-away sheath; and
      wherein, the sheath tool is configured for break-away removal of the break-away sheath from the working member of the implantation tool to remove the break-away sheath from the at least a portion of the member of the implantation tool disposed in the second internal passage in the break-away sheath.

2. An implantation tool assembly according to claim 1, wherein the working member is a hollow member.

3. An implantation tool assembly according to claim 1, wherein at least a portion of the implant device mounted on the working member is located proximal of the break-away sheath.

4. An implantation tool assembly according to claim 3, wherein at least a distal portion of the working member is exposed distal of the break-away sheath.

5. An implantation tool assembly according to claim 4, comprising a hollow dilator member annularly disposed between the working member and the break-away sheath.

6. An implantation tool assembly according to claim 1, wherein the working member has a longitudinal length at least as long as the combined longitudinal lengths of the implant device and the sheath tool.

7. An implantation tool assembly according to claim 1, wherein:
   the working member has an exterior width within a range of from 0.7 to 1.3 millimeters;
   the working member has a longitudinal length in a range of from 70 to 225 millimeters;
   the break-away sheath has a longitudinal length in a range of from 20 to 75 millimeters; and
   the implant device has a longitudinal length in a range of from 10 to 25 millimeters.

8. An implantation tool assembly according to claim 1, wherein the sheath tool comprises tab portions adjacent the proximal end of the sheath tool for manually manipulating the sheath tool and for exerting a force to commence break-away removal of the break-away sheath.

9. An implantation tool assembly according to claim 1, wherein the implant device comprises:
- a conduit extending from adjacent the proximal end to adjacent the distal end and the internal passage extends between the proximal end and the distal end and through the conduit, the internal passage having a first end open at the proximal end and a second end open at the distal end;
- an exterior of the conduit comprising an anchoring surface feature including protrusion areas and recess areas; and
- the implant device is configured to be implanted to fluidly connect the lacrimal apparatus to the paranasal sinus through the fistula so that when implanted:
  - the proximal end is disposed with the first end of the internal passage opening in the lacrimal apparatus;
  - the distal end is disposed in the paranasal sinus with the second end of the internal passage opening in the paranasal sinus; and
  - the conduit is disposed through the fistula with at least a portion of the recess areas disposed within the fistula and with at least a portion of the protrusion areas disposed in the fistula and engaging tissue exposed within the fistula to anchor the implant device.

10. An implantation tool assembly according to claim 9, wherein:
- the protrusion areas have a height relative to the recess areas in a range of from 0.1 millimeter to 1 millimeter;
- the protrusion areas comprise protrusion occurrences having a center-to-center spacing in a range of 0.75 millimeter to 2 millimeters;
- the protrusion areas are on a longitudinal portion of the conduit extending at least 3 millimeters along the length of the device;
- the conduit has a length is in a range of from 8 millimeters to 30 millimeters; and
- the conduit has an exterior width defined by an extent of the protrusion areas transverse to the length that is within a range of from 1.5 millimeters to 3 millimeters.

11. An implantation tool assembly according to claim 1, wherein comprises:
- a conduit extending from adjacent the proximal end to adjacent the distal end, and the internal passage extends between the proximal end and the distal end and through the conduit, the internal passage having a first end open at the proximal end and a second end open at the distal end;
- a head adjacent the conduit at the proximal end, the head having a length dimension in a range of from 2 to 8 millimeters and a width dimension transverse to the length dimension with a ratio of the length dimension to the width dimension being in a range of from 1.5 to 4;
- the implant device configured to be implanted to fluidly connect the lacrimal apparatus in the orbit and the paranasal sinus through the fistula so that when implanted:
  - the proximal end and the head are disposed with the first end of the internal passage opening in the lacrimal apparatus;
  - the distal end is disposed in the paranasal sinus with the second end of the internal passage opening in the paranasal sinus; and
  - the conduit is disposed through the fistula.

12. An implantation kit with components for implantation of an implant device to provide an artificial fluid path in fluid communication with the lacrimal apparatus, the implantation kit comprising:
- an implant device, the implant device comprising:
  - a proximal end and a distal end at opposite longitudinal ends of the implant device;
  - a first internal passage extending between the proximal end and the distal end of the implant device and having a first end open at the proximal end of the implant device and a second end open at the distal end of the implant device;
  - a longitudinal length between the proximal end and the distal end of the implant device in a range of from 2 millimeters to 50 millimeters;
  - a width of the first internal passage transverse to the length in a range of from 0.25 millimeter to 5 millimeters; and
  - wherein, the implant device is configured to be implanted with the proximal end disposed in the lacrimal apparatus;
- an implantation tool with a proximal end and a distal end, the implantation tool comprising:
  - a working member extending longitudinally in a direction from the proximal end toward the distal end of the implantation tool; and
  - a hand-manipulable handle connected with the working member and hand graspable proximal of the working member to hand manipulate the implantation tool;
  - wherein, the working member is configured to be slidably inserted through the first internal passage of the implant device to mount the implant device on the working member with the proximal end of the implant device disposed toward the handle and the distal end of the implant device disposed toward the distal end of the implantation tool;
- a sheath tool with a proximal end and a distal end, the sheath tool comprising:
  - a break-away sheath and a second internal passage extending longitudinally through the break-away sheath in a direction from the proximal end toward the distal end of the sheath tool;
  - wherein, the sheath tool is configured to slidably receive at least a portion of the working member in the second internal passage; and
  - wherein, the sheath tool is configured for break-away removal of the break-away sheath from the working member of the implantation tool when a portion of the working member of the implantation tool is disposed in the second internal passage.

13. An implantation kit according to claim 12, wherein the implantation tool and the sheath tool are assemblable in the absence of the implant device in a first tool assembly configuration useful for forming a fistula having a proximal end opening into the lacrimal apparatus; and
- in the first tool assembly configuration the working member is inserted through the second internal passage of the break-away sheath with the proximal end of the sheath tool disposed toward the handle of the implantation tool and with a distal portion of the working member exposed distal of a distal end of the break-away sheath.

14. An implantation kit according to claim 12, wherein the implantation tool, the implantation device and the sheath tool are assemblable in a tool assembly configuration useful for implanting the implant device in a fistula having a proximal end opening into the lacrimal apparatus; and in the tool assembly configuration the working member is inserted through the first internal passage of the implantation device with the proximal end of the implantation device disposed toward the handle of the implantation tool and the working member is inserted through at least a portion of the second internal passage with the proximal end of the sheath tool disposed toward the handle of the working member, wherein at least a portion of the implant device is disposed proximal of the break-away sheath.

15. An implantation kit according to claim 13, comprising a dilator tool including a hollow dilator member, wherein:
the hollow dilator tool is assemblable with the implantation tool and the sheath tool in the first tool assembly configuration with at least a portion of the hollow dilator member disposed annularly between the working member and the break-away sheath and with at least a distal portion of the working member being exposed distal of a distal end of the hollow dilator member; and
in the first tool assembly configuration, the implantation tool and the dilator tool are slidably disengageable from the proximal end of the sheath tool, whereby after the first tool assembly configuration is used to form the fistula, the implantation tool and the dilator tool are retractable to disengage from the sheath tool to leave the sheath tool disposed with at least a portion of the break-away sheath within the fistula.

16. An implantation kit according to claim 15, wherein in the first tool assembly configuration, the distal end of the dilator member is disposed distal of the distal end of the sheath tool and proximal of the distal end of the implantation tool.

17. A method for implanting an implant device to provide an artificial fluid path in fluid communication with the lacrimal apparatus, the method comprising:
positioning an implantation tool assembly in an implantation position relative to a fistula having a proximal end opening into the lacrimal apparatus;
wherein, the implantation tool assembly comprises:
an implantation tool with a proximal end and a distal end, the implantation tool comprising:
a working member extending longitudinally in a direction from the proximal end toward the distal end of the implantation tool assembly; and
a hand-manipulable handle connected with the working member and hand graspable proximal of the working member to hand manipulate the implantation tool;
an implant device, the implant device comprising:
a proximal end and a distal end at opposite longitudinal ends of the implant device;
a first internal passage extending between the proximal end and the distal end of the implant device and having a first end open at the proximal end of the implant device and a second end open at the distal end of the implant device;
wherein, the implant device is configured to be implanted with the proximal end disposed in the lacrimal apparatus; and
wherein, the implant device is slidably mounted on the working member with the working member disposed through the first internal passage and with the proximal end of the implant device disposed toward the handle and the distal end of the implant device disposed toward the distal end of the implantation tool;
a sheath tool with a proximal end and a distal end, the sheath tool comprising:
a break-away sheath and a second internal passage extending longitudinally through the break-away sheath in a direction from the proximal end toward the distal end of the sheath tool;
wherein, at least a portion of the working member distal to the implant device is slidably disposed in the second internal passage;
wherein, when the implantation tool assembly is in the implantation position:
at least a portion of the break-away sheath and at least a portion of the working member disposed within the second internal passage are disposed in the fistula; and
at least a portion of the implant device is disposed proximal of the fistula;
after the positioning the implantation tool assembly in the implantation position, removing the break-away sheath from the working member while maintaining disposed in the fistula at least a portion of the working member distal of the implant device;
after the removing the break-away sheath, positioning the implant device with at least a portion of the implant device disposed in the fistula while maintaining at least a portion of the working member disposed in the fistula; and
after the positioning the implant device, removing the working member from the first internal passage to disengage the implantation tool from the implant device and to leave the implant device in an implanted position with at least a portion of the implant device disposed in the fistula and with the proximal end of the implant device disposed in the lacrimal apparatus.

18. A method according to claim 17, comprising prior to the positioning the implantation tool assembly in the implantation position:
forming the fistula, comprising piercing tissue adjacent the lacrimal apparatus with the working member.

19. A method according to claim 18, wherein during the forming the fistula, the implant device is mounted on the working member with at least a portion of the implant device located proximal of the break-away sheath.

20. A method according to claim 18, wherein during the forming the fistula the implant device is not mounted on the working member, and the method comprises after the forming the fistula and before the positioning the implantation tool assembly in the implantation position:
retracting the working member from the fistula; and
slidably mounting the implant device on the working member.

* * * * *